(12) United States Patent
Prusiner et al.

(10) Patent No.: US 6,719,988 B2
(45) Date of Patent: *Apr. 13, 2004

(54) ANTISEPTIC COMPOSITIONS FOR INACTIVATING PRIONS

(75) Inventors: Stanley B. Prusiner, San Francisco, CA (US); Surachai Supattapone, Hanover, NH (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,178

(22) Filed: Jul. 11, 2001

(65) Prior Publication Data

US 2002/0041859 A1 Apr. 11, 2002

Related U.S. Application Data

(63) Continuation-in-part of application No. 09/699,284, filed on Oct. 26, 2000, which is a continuation-in-part of application No. 09/494,814, filed on Jan. 31, 2000, now Pat. No. 6,322,802, which is a continuation-in-part of application No. 09/447,456, filed on Nov. 22, 1999, now Pat. No. 6,331,296, which is a continuation-in-part of application No. 09/322,903, filed on Jun. 1, 1999, now Pat. No. 6,214,366, application No. 09/904,178, which is a continuation-in-part of application No. 09/235,372, filed on Jan. 20, 1999, now Pat. No. 6,221,614, which is a continuation-in-part of application No. 09/151,057, filed on Sep. 10, 1998, now abandoned, which is a continuation-in-part of application No. 09/026,957, filed on Feb. 20, 1998, now abandoned, which is a continuation-in-part of application No. 08/804,536, filed on Feb. 21, 1997, now Pat. No. 5,891,641.

(51) Int. Cl.[7] .............................................. A01N 25/02
(52) U.S. Cl. .................... 424/405; 424/406; 424/78.07; 424/89; 424/93.1; 424/93.6; 514/553; 514/557; 514/578; 514/709
(58) Field of Search ................................ 424/405, 451, 424/78.08, 406, 78.07; 514/553, 557, 578, 709; 44/93.1, 93.6

(56) References Cited

U.S. PATENT DOCUMENTS

4,300,905 A    11/1981    Bleisteiner et al. ........... 23/230

(List continued on next page.)

FOREIGN PATENT DOCUMENTS

| CA | 1244759 | 11/1988 |
| DE | 3229097 A1 | 2/1984 |

(List continued on next page.)

OTHER PUBLICATIONS

West–Textbook of Biochemistry 4th edition Proteins–pp. 342–346; 328, 1988.*
Dabatase Biosis: (Supattapone et al., "Elimiation of prions by branched polyamines and implications for therapeutics" Database Acession No. PREV200000056439 XP–002191399 Abstract and *Proc. Natl. Acad. Sci. USA* (Dec. 7, 1999) 96(25):14529–14534).

(List continued on next page.)

*Primary Examiner*—Neil S. Levy
(74) *Attorney, Agent, or Firm*—Karl Bozicevic; Bozicevic, Field & Francis LLP

(57) ABSTRACT

An antiseptic composition useful in destroying the infectivity of infectious proteins such as prions is disclosed. The antiseptic composition is preferably maintained at a pH of 4.0 or less which allows for an environment under which the active component destroys infectivity. The composition may be added to blood, blood products, collagen, tissues and organs prior to transplantation. The composition also may be added to livestock feed to denature any prions in the livestock. Methods of denaturing infectious proteins are also disclosed.

3 Claims, 12 Drawing Sheets

U.S. PATENT DOCUMENTS

| | | | |
|---|---|---|---|
| 4,320,086 A | 3/1982 | Reiss | 422/56 |
| 4,587,329 A | 5/1986 | Tomalia et al. | 528/363 |
| 4,806,627 A | 2/1989 | Wisniewski et al. | 530/387 |
| 5,308,611 A | 5/1994 | Thompson | 424/78.07 |
| 5,336,432 A | 8/1994 | Petchul et al. | 252/186.28 |
| 5,499,979 A | 3/1996 | Wong et al. | 604/891.1 |
| 5,521,060 A | 5/1996 | Hoenes et al. | 435/4 |
| 5,547,576 A | 8/1996 | Onishi et al. | 210/500.37 |
| 5,565,186 A | 10/1996 | Prusiner et al. | 424/9 |
| 5,633,349 A | 5/1997 | Reichl | 530/364 |
| 5,757,361 A | 5/1998 | Hirshik | 345/156 |
| 5,780,288 A | 7/1998 | Rohwer | |
| 5,808,011 A | 9/1998 | Gawryl et al. | 530/416 |
| 5,834,020 A | 11/1998 | Margerum et al. | 424/484 |
| 5,846,533 A | 12/1998 | Prusiner et al. | 424/130 |
| 5,858,326 A | 1/1999 | Kisilevsky et al. | 424/9 |
| 5,919,442 A | 7/1999 | Yin et al. | 424/78 |
| 5,977,324 A | 11/1999 | Prusiner et al. | 530/418 |
| 6,025,312 A | 2/2000 | Saito et al. | 510/130 |
| 6,096,216 A | 8/2000 | Shanbrom et al. | 210/638 |
| 6,106,773 A | 8/2000 | Miekka et al. | 422/28 |
| 6,110,908 A | 8/2000 | Guthery | 514/18 |
| 6,127,448 A | 10/2000 | Domb | 523/105 |
| 6,150,172 A | 11/2000 | Schmerr et al. | 435/975 |
| 6,190,650 B1 | 2/2001 | Matthews et al. | 424/78.17 |
| 6,197,207 B1 | 3/2001 | Chapman et al. | 210/767 |
| 6,197,935 B1 | 3/2001 | Doillon et al. | 530/356 |
| 6,322,802 B1 * | 11/2001 | Prusiner et al. | 424/405 |
| 6,331,296 B1 * | 12/2001 | Prusiner et al. | 424/78.08 |

FOREIGN PATENT DOCUMENTS

| | | |
|---|---|---|
| WO | WO 93/10227 | 5/1993 |
| WO | WO 93/23432 | 11/1993 |
| WO | WO 95/31466 | 11/1995 |
| WO | WO 97/43649 | 11/1997 |
| WO | WO 98/15297 | 4/1998 |
| WO | WO 98/32334 | 7/1998 |
| WO | WO 98/37411 A | 8/1998 |
| WO | WO 99/42102 | 8/1999 |
| WO | WO 99/42487 | 8/1999 |
| WO | WO 00/65344 | 11/2000 |
| WO | WO 00/72851 A1 | 12/2000 |

OTHER PUBLICATIONS

Alpatova, N.M., et al., (1994) "Comparison of Electrochemical Behavior of Heteropolyacids in Solution and Immobilized in a Conducting Polymer Film", Chemical Abstracts, vol. 121, No. 16.

Anderson, et al., (1996) "Transmission dynamics and epidemiology of BSE in British cattle," Nature 382: 779–88.

Barry, R.A., et al., (1986) "Monoclonal Antibodies to the Cellular and Scrapie Prion Proteins," Journal of Infectious Diseases 154:518–521.

Basler, et al., (1986) "Scrapie and Cellular PrP Isoforms Are Encoded by the Same Chromosomal Gene," Cell, 46:417–28.

Bendheim, et al., (1984) "Antibodies to a Scrapie Prion Protein," Nature 310:418–421.

Bode, et al., (1985) "Characterization of Antisera Against Scrapie–Associated Fibrils (SAF) from Affected Hamster and Cross–Reactivity with SAF from Scarpie–Affected Mice and from Patients with Creutzfeldt–Jacob Disease," J. Gen. Virol. 66:2471–2478.

Bolton, et al., (1982) "Identification of a Protein That Purifies with the Scrapie Prion," Science 218: 1309–11.

Brown, et al., (1992) "'Friendly Fire' in Medicine: Hormones, Homografts, and Creutzfeldt–Jakob Disease," Lancet 340: 24–27.

Bruce, M.E., et al., (1997) "Transmissions to mice indicate that 'new variant' CJD is caused by the BSE agent," Nature, vol. 389:498–501.

Buchanan, et al., (1991) "Mortality, Neoplasia, and Creutzfeldt–Jakob Disease in Patients Treated with Human Pituitary Growth Hormone in the United Kingdom", BMJ 302:824–828.

Bueler, et al., (1992) "Normal Development and Behavior of Mice Lacking the Neuronal Cell–surface PrP Protein," Nature 356:577–582.

Carter, et al., (1992) "High Level *Escherichia coli* Expression and Production of a Bivalent Humanized Antibody Fragment," Biotechnology 10:163–7.

Cochius, et al., (1990) "Creutzfeldt–Jakob Disease in a Recipient of Human Pituitary–Derived Gonadotrophin," Aust. N.Z. J. Med. 20:592–593.

Cochius, et al., (1992) "Creutzfeldt–Jakob Disease in a Recipient of Human Pituitary–Derived Gonadotrophin: A Second Case," J. Neurol. Neurosurg. Psychiatry 55:1094–1095.

Collinge, et al., (1996) "Prion protein gene analysis in new variant cases of Creutzfeldt–Jakob disease," Lancet 348: 56.

Combs, et al, (1999) "Identification of Microglial Signal Transduction Pathways Mediating a Neurotoxic Response to Amyloidogenic Fragments of .beta.–Amyloid and Prion Proteins," The Journal of Neuroscience, 19(3):928–939.

Cousens, S.N., et al., (1997) "Predicting the CJD epidemic in humans," Nature, vol. 385:197–198.

Gabizon, et al., (1988) "Immunoaffinity purification and neutralization of scrapie prion infectivity," Proc. Natl. Acad. Sci. USA, vol. 85, pp. 6617–6621.

Gajdusek, (1977) "Unconventional Viruses and the Origin and Disappearance of Kuru" Science, 197(4307):943–960.

Gajdusek, D.C., et al., (1966) "Experimental transmission of a kuru–like syndrome to chimpanzees," Nature, vol. 209:794–796.

Gibbs, C.J., Jr., et al., (1968) "Creutzfeldt–Jakob disease (spongiform encephalopathy): transmission to the chimpanzee," Science, vol. 161:388–389.

Gibbs, Jr., et al, (1993) "Creutzfeldt–Jakob Disease Infectivity of Growth Hormone Derived from Human Pituitary Glands," N. Engl. J. Med. 328:358–359.

Gioia et al., (1994) "Conformational Polymorphism of the Amyloidogenic and Neurotoxic Peptide Homologous to Residues 106–126 of the Prion Protein," *Journal of Biological Chemistry*, vol. 269(11):7859–7862.

Glenner, et al., (1989) "Amyloidosis of the nervous system," J. Neurol. Sci., 94:1–28.

Goldfarb, et al., (1992) "Fatal Familial Insomnia and Familial Creutzfeldt–Jakob Disease: Disease Phenotype Determined by a DNA Polymorphism," Science 258:806–808.

Greenberg, et al., (1993) *Neurology*, vol. 43:2073–9.

Haan, et al., (1990) "Amyloid in Central Nervous System Disease," Clin. Neurol Neurosurg. 92(4):305–310.

Hardy, (1997) "Amyloid the Presenilins and Alzheimer's Disease," Trends Neurosci. 20(4):154–159.

Healy, et al., (1993) "Creutzfeldt–Jakob Disease After Pituitary Gonadotrophins: The Prion is the Problem," BMJ 307:517–518.

Hill, A.F., et al, (1997) "The same prion strain causes vCJD and BSE," *Nature*, vol. 389:448–450.

Hsiao, et al., (1994) "Serial transmission in rodents of neurogeneration from transgenic mice expressing mutant rion protein," Proc. National Acad. Sci. USA 91:9126–30.

Ingrosso, L., et al., (1995) "Congo red prolongs the incubation period in scrapie–infected hamsters," *J. Virol.*, vol. 69:506–508.

Itoh et al., (1993) *J. Neurol. Neurosurg.*, vol. 16:135–41.

Kalaria, et al., (1995) "Differential Degeneration of the Cerebral Microvasculature in Alzheimer's Disease," NeuroReport 6:477–480.

Kamada, M., et al., (1993) "Dispersion and Fixation of 12–Tungstrophosphate Anion on a Silica Surface Modified with Silane Agents Having an Amine Group and Their Catalytic Properties," Bull. Chem. Soc. JPN., vol. 66, pp. 3565–3570.

Karlsson, et al., (1991) "Analysis and isolation of human transferrin receptor using the OKT–9 monoclonal antibody covalently crosslinked to magnetic beads," Analytical Biochemistry, vol. 199, pp. 219–222.

Kascsak et al., (1993) "The Role of Antibodies to PRP in the Diagnosis of Transmissible Spongiform Encephalopathies," *Developments in Biological Standardization, Ch, Basel*, vol. 80:141–151.

Kascsak, R.J., et al., (1987) "Mouse Polyclonal and Monoclonal Antibody to Scrapie–Associated Fibril Proteins" Journal of Virology 61:3688–3693.

Kawai, et al., (1993) "Degeneration of Vascular Muscle Cells in Cerebral Amyloid Angiopathy of Alzheimer's Disease." Brain Res. 623:142–146.

Kelly, (1996) "Alternative Conformations of Amyloidogenic Proteins Govern Their Behavior," Current Opinions in Structural Biology, Strut Biol 6(1):11–17.

Kimberlin, R.H., et al., (1986) "Suppression of Scrapie Infection In Mice by Heteropolyanion 23, Dextran Sulfate, and Some Other Polyanions," Antimicrobial Agents and Chemotherapy, vol. 30, No. 3, pp. 409–413.

Korth, et al., (1997) "Prion (PrPsc)–specific epitope defined by a monoclonal antibody," Nature, vol. 390, pp. 74–77.

Ladogana, A., et al., (1992) "Sulphate polyanions prolong the incubation period of scrapie–infected hamsters," *J. Gen. Virol.*, vol. 73:661–665.

Lai, et al., (1996) "The Acid–Mediated Denaturation Pathway of Transthyretin Yields a Conformational Intermediate Than Can Self–Assemble into any Amyloid," Biochemistry, 35(20):6470–6482.

Lasmézas, C.I., et al., (1996) "BSE transmission to macaques," *Nature*, vol. 381;743–744.

Lasmezas, et al., (1993) "Recombinant Human Growth Hormone and Insulin–Like Growth Factor I Induce PRP Gene Expression in PC12 Cell," Biochem. Biophys. Res. Commun. 196:1163–1169.

Lendon, et al., (1997) "Exploring the Etiology of Alzheimer Disease Using Molecular Genetics," J. Am. Med. Assoc., 277(10):825–831.

Levy et al., (1990) *Science*, vol. 248:1124–6.

Mandybur, (1989) "Cerebral Anyloid Angiopathy and Astroc Glisos in Alzheimer's Disease," Acta Neruopath., 78:329–331.

Martin, et al., (1994) "Synaptic Pathology and Glial Responses to Neuronal Injury Precede the Formation of Senile Plaques and Amyloid Deposits in the Aging Cerebral Cortex," Amer. Journal of Pathology, 145(6):1358–1381.

Masliah, et al., (1996) "Comparison of Neurodegenerative Pathology in Transgenic Mice Overexpressing V717F .beta.–Amyloid Precursor Protein and Alzheimer's Disease," Journal of Neuroscience, 16(18):5795–5811.

Masullo, C., et al., (1992) "Failure of ameliorate Creutzfeldt–Jakob disease with amphotericin B therapy," *J. Infect. Dis.*, vol. 165:784–785.

McCutchen et al., (1993) "Intermolecular Disulfide Linkages Are Not Required for Transthyretin Amyloid Fibril Formation in Vitro," Biochem., Biophys, Res. Commun, 197(2) 415–21.

McCutchen, et al., (1993) "Transthyretin Mutation Leu–55–Pro Significantly Alters Tetramer Stability and Increases Amyloidogenicity," Biochemistry, 32(45):12119–12127.

McKinley, et al., (1983) "A Protease–Resistant Protein is a Structural Component of the Scrapie Prion," Cell 35:57–62.

Medori, et al., (1992) "Fatal Familial Insomnia, A Prion Disease With a Mutation at Codon 178 of The Prion Protein Gene," New England Journal of Medicine, 326(7):444–449.

Medori, Tritschler et al, (1992) *N Engl J Med*, vol. 326:444–449.

Mehlhorn, et al., (1996) "High–Level Expression and Characterization of a Purified 142–Residue Polypeptide of the Prion Protein," Biochemistry 35: 5528–37.

Meyer, et al., (1987) "Separation and Properties of Cellular and Scrapie Prion Proteins," USA 83: 2310–2314.

Miroy, (1996) "Inhibiting Transthyretin Amyloid Fibril Formation via Protein Stabilization," Proc. Natl. Acad. Sci. USA, 93(26):15051–15056.

Nguyen et al., (1995) "Prion Protein Peptides Induce Alpha–helix to Beta–Sheet Conformational Transitions," *Biochemistry*, pp. 4186–4192.

Oesch, et al., (1985) "A Cellular Gene Encodes Scrapie PrP 27–30 Protein," Cell 40: 735–46.

Pan, Baldwin et al., (1993) "Conversion of α–Helices β–Sheets Features in the Formation of the scrapie Prion Proteins," *Proc Natl Acad Sci USA*, vol. 90:10962–10966.

Pan, et al., (1992) "Purification and Properties of the Cellular Prion Protein from Syrian Hamster Brain," Protein Sci. 1:1343–1352.

Pan, et al., (1993) "Conversion of .alpha.–Helices into .beta.–Sheets Features in the Formation of the Scrapie Prion Proteins," Proc. Natl. Acad. Sci. USA, 90:10962–10966.

Prusiner et al., (1993) "Immunologic and Molecular Biologic Studies of Prion Proteins in Bovine Spongiform Encephalopathy," *Journal of Infectious Diseases*, vol. 167:602–613.

Prusiner, (1997) "Biology of Prions," The Molecular and Genetic Basis of Neurological Disease, 2nd Edition, Ch. 7., pp. 103–143.

Prusiner, S.B. (1989), "Scrapie prions," *Annu. Rev. Microbiol.*, vol. 43:345–374.

Prusiner, S.B., (1998) "Prions," *Proc. Natl. Acad. Sci. USA*, vol. 95:13363–13383.

Prusiner, S.B., et al., (1983) "Scrapie prions aggregate to form amyloid–like birefringent rods," Cell 35: 349–58.

Rogers, et al., (1991) "Epitope Mapping of the Syrian Hamster Prion Protein Utilizing Chimeric and Mutant Genes in a Vaccinia Virus Expression System," J. Immunol. 147: 3568–74.

Rogers, et al., (1993) "Conversion of truncated and elongated prion proteins into the scrapie isoform in cultured cells," Proc. Natl. Acad. Sci. USA 90:3182–6.

Safar, et al., (1990) "Scrapie–associated precursor proteins: Antigenic relationship between species and immunocytochemical localization in normal, scrapie, and Creutzfeldt–Jakob disease brains," Neurology 40:513–7.

Safar, et al., (1993) "Conformational Transitions, Dissociation, and Unfolding of Scrapie Amyloid (Prion) Protein," Journal of Biol. Chem., 268(27):20276–20284.

Safar, J., et al., (1998) "Eight Prion Strains Have PrP$^{Sc}$ Molecules With Different Conformations," Nature Medicine, vol. 4, No. 10, pp. 1157–1165.

Saidkhanov, S.S., et al., (1983) "Changes in Catalytic Properties of 12–Heteropolyacids in Reaction of Dihydrogen Evolution From Water Induced By Their Immobilization on Anion–Exchange Polymers," Journal of Molecular Catalysis, vol. 21, pp. 365–373.

Schmerr, Mary Jo et al., (1996) "Improvements in a Competition Assay to Detect Scrapie Prion Protein by Capillary Eletrophoresis", Journal of Chromatography B 681:29–35.

Selkoe, (1993) "Physiological Production of the .beta.–Amyloid Protein and the Mechanism of Alzheimer's Disease," Trends in Neurosciences, 16(10):403–409.

Selkoe, (1996) "Amyloid .beta.–Protein and the Genetics of Alzheimer's Disease," Journ. of Biol. Chem., 271(31):18295–8.

Selkoe, et al., (1988) "beta.–Amyloid Precursor Protein of Alzheimer Disease Occurs as 110–to 135–Kilodalton Membranes–Associated Proteins in Neural and Nonneural Tissues," Proc. Natl. Acad. Sci. USA. 85:7341–7345.

Serban, et al, (1990) "Rapid Detection of Creuzfeldt–Jakob Disease and Scrapie Prion Proteins," Neurology 40:110–7.

Setchel, C.H., (1985) "Magnetic separations in biotechnology—a review," J. Chem. Tech. Biotechnol., vol. 35B, pp. 175–182.

Stahl, et al., (1993) "Structural Studies of the Scrapie Prion Protein Using Mass Specrometry and Amino Acid Sequencing," Biochemistry 32: 1991–2002.

Tagliavini, F., et al. (1997) "Effectiveness of anthracycline against experimental prion disease in Syrian hamsters," Science, vol. 276, 1119–1122.

Taraboulos, et al., (1992) "Regional Mapping of Prion Proteins in Brain," Proc. Natl. Acad. Sci. USA 89:7620–7624.

Terry et al., (1994) "Structural alteration in Alzheimer's Disease," In: Alzheimer's Disease (Terry et al. Eds.) pp. 179–196.

Turk, et al., (1988) "Purification and Properties of the Cellular and Scrapie Hamster Prion Proteins," Eur. J. Biochem. 176:21–30.

Vinters, Hary V., (1987) "Cerebral Amyloid Angiopathy A Critical Review," Stroke, vol. 18(2):311–324.

Wilesmith, (1996) "Bovine Spongiform Encephalopathy," Methods in Molecular Medicines: Prion Diseases, pp. 155–73..

Wilesmith, et al., (1991) "Bovine Spongiform Encephalopathy," Current Topics in Microbiology and Immunology. 172:21–38.

Will, R.G., et al. (1996) "A new variant of Creutzfeldt–Jakob disease in the UK." Lancet, vol. 347:921–925.

Will, R.G., et al. (1999) "Deaths from variant Creutzfeldt–Jakob disease," Lancet 353:979.

Williamson, et al., (1996) "Circumventing tolerance to generate autologous monoclonal antibodies to the prion protein," Proc. Natl. Acad. Sci. USA 93: 7279–82.

Yamada, et al., (1993) Journal of Neurology, Neurosurgery and Psychiatry, vol. 56:543–547.

Yankner, (1996) "New Clues to Alzheimer's Disease: Unraveling the Roles of Amyloid and Tau," Nature Medicine, 2(8):850–852.

Yokoyama, Takashi, et al., (1996) "Immunoreactivity of Specific Epitopes of PrP .sup.Sc is Enhanced by Pretreatment in a Hydrated Autoclave," Clinical and Diagnostic Laboratroy Immunology 3(4):470–471.

Antolga et al., "Prion Disease and Medical Devices" ASAIO Journal, pp. S69–S72 (2000).

Darbord, "Inactivation of Prions in daily medical practice" Biomed & Pharmacother. 53:34–38 (1999).

Ernst, "Comparative analysis of scrapie agent inactivation methods" J. Virol. Methods, 41:193–202 (1993).

Taylor "Transmissable Degenerative Encephalopathies: Inactivation of the Unconventional Causal Agents" in Principles and Practice of Disinfection, Preservation and Sterilzation, Oxford, Blackwell Science, 1999 pp. 222–236.

Taylor, "Resistance of the ME7 scrapie agent to peracetic acid," Veterinary Microbiology 27:19–24 (1991).

Taylor et al., "Survival of scrapie agent after exposure to sodium dodecyl sulphate and heat," Veterinary Microbiology 67:13–16 (1999).

* cited by examiner

FIG. 6A

FIG. 6B 2 hr 5 min

US 6,719,988 B2

ANTISEPTIC COMPOSITIONS FOR INACTIVATING PRIONS

CROSS-REFERENCES

This application is a continuation-in-part of U.S. application Ser. No. 09/699,284, filed Oct. 26, 2000, which is a continuation-in-part of U.S. application Ser. No. 09/494,814, filed Jan. 31, 2000 now U.S. Pat. No. 6,322,802, which is a continuation-in-part of U.S. application Ser. No. 09/447,456, filed Nov. 22, 1999 now U.S. Pat. No. 6,331,296, which is a continuation-in-part of U.S. application Ser. No. 09/322,903, filed Jun. 1, 1999, now U.S. Pat. No. 6,214,366 and to which priority is claimed under 35 U.S.C. § 120. This application is also a continuation-in-part of Ser. No. 09/235,372 Jan. 20, 1999, now U.S. Pat. No. 6,221,614, issued Apr. 24, 2001, which is a continuation-in-part of U.S. application Ser. No. 09/151,057, filed on Sep. 10, 1998 now abandoned, which is a continuation-in-part of U.S. application Ser. No. 09/026,957, filed on Feb. 20, 1998 now abandoned, which is a continuation-in-part of U.S. application Ser. No. 08/804,536, filed on Feb. 21, 1997, now U.S. Pat. No. 5,891,641, and to which priority is claimed under 35 U.S.C. § 120.

GOVERNMENT SUPPORT

This work was supported, in part, by grants from the National Institutes of Health NS14069, AG08967, AG02132, AG10770 and K08 NS02048-02. The government may have certain rights in this work.

FIELD OF THE INVENTION

The present invention relates generally to compositions for inactivating infectious prions in a range of different products including, blood, organ and tissue products, food products and livestock feed.

BACKGROUND OF THE INVENTION

Antiseptic compositions have been known for over 100 years. In addition to various compositions there are a range of different methods, which are known to be effective in killing bacteria and inactivating viruses. Such methods include the use of high temperature, alone or in combination with radiation, over sufficient periods of time to kill bacteria or disrupt viruses and thereby inactivate them. These methods are extreme, and can damage sensitive medical equipment, thus decreasing its useful life.

Examples of fast acting topical antiseptic compositions are disclosed n U.S. Pat. No. 6,110,908, issued Aug. 29, 2000. Another antibacterial composition is disclosed in U.S. Pat. No. 6,025,312, issued Feb. 15, 2000. Examples of other antiseptic compositions are taught within U.S. Pat. No. 5,336,432, issued Aug. 9, 1994; U.S. Pat. No. 5,308,611, issued May 3, 1994; U.S. Pat. No. 6,106,773, issued Aug. 22, 2000 and U.S. Pat. No. 6,096,216, issued Aug. 1, 2000.

Conventional antiseptic compositions and antiseptic methodologies are generally insufficient for inactivating infectious proteins such as prions. Although prions can be inactivated by relatively high temperatures over very long periods of time, the temperature ranges and time periods generally used to kill bacteria and inactivate the viruses are insufficient to inactivate prions. One approach to solving this problem is to attempt to remove prions from solutions. A chromographic removal process is disclosed within U.S. Pat. No. 5,808,011. Further, others have attempted to provide compositions and methodologies that are intended to inactivate prions as taught within U.S. Pat. No. 5,633,349.

However, such processes generally take relatively long periods of time (e.g., more than 12 hours) and generally do not provide a solution that could be readily and economically utilized in order to inactivate prions on food products, biological materials, medical equipment, and livestock feed.

The present invention offers antiseptic compositions and methods, which may be utilized under mild conditions, for inactivating prions that will not damage any existing equipment, food, or biological substance, as described below.

BRIEF DESCRIPTION OF THE DRAWINGS

In FIG. 2A, lane 3 shows results where no dendrimers were added and prions remain whereas dendrimers were added in lane 4 showing the removal of $PrP^{Sc}$ present in a cell culture. FIG. 2B shows that the use of dendrimers in compositions of the invention does not effect overall protein expression. FIG. 2C shows that when cells are assayed for prion infectivity by injection into mice showing the use of dendrimers cures cells.

In FIG. 5 there is a showing that the addition of urea enhances the ability of dendrimers to denature and remove prion infectivity.

FIG. 6 includes high-resolution photographs 6A and 6B, which provide a visualization of what happens to prion rods exposed to dendrimers.

SUMMARY OF THE INVENTION

Figure 1:
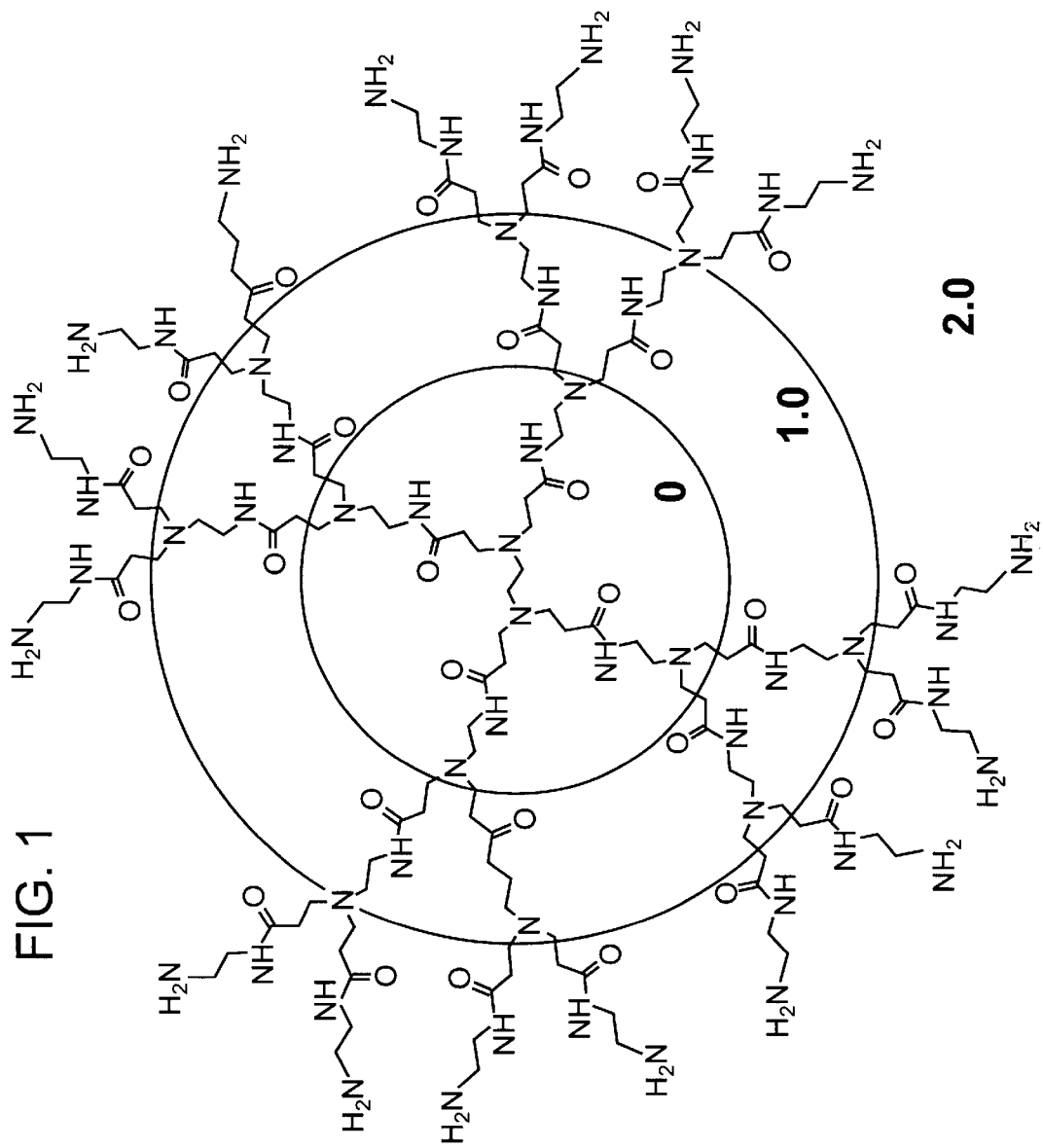
FIG. 1 is a schematic drawing of a dendrimer molecule showing the defined "generations" of homodisperse structure created using a repetitive divergent growth technique. The specific diagram is of PAMAM, generation 2.0 (ethylene diamine core).

An antiseptic composition is disclosed which is comprised of a first agent that maintains the pH of the composition at about 5.0 or less, preferably about 4.0 or less; and a second agent characterized by its ability to destroy prion infectivity in the low pH environment created by the first component. The first agent may be any well known acid present in an aqueous solution at sufficient molarity so as to reduce the pH of the antiseptic composition to about 5.0 or less, and preferably about 4.0 or less and maintain the pH at that low level when the antiseptic composition is applied to an object or mixed with a material to be treated. The second agent or active agent is characterized by its ability to inactivate prions (destroy infectivity) when held in the acid environment for as little as two hours or less. The advantage of the composition is that it will not damage existing equipment or material because it is not applied under harsh conditions.

The composition of the invention will vary due to the large number of different acids and inactivating agents that can be used. As temperature is increased and pH is lowered the inactivation occurs more rapidly. Compositions of the invention preferably inactivate prions in about 2 hours or less at a pH of about 4.0 or less at temperatures of about 4° C. to 40° C. However, low temperatures (e.g., 0° C. or higher) and high temperatures (e.g., 100° C. or less) can be used, as can longer time periods. The inactivation can occur more quickly (e.g., in one minute or less) and can be carried out at lower pH levels (e.g., 3.0 or less) and at higher temperatures (e.g., greater than 40° C.). An aspect of the invention is that the denaturing conditions are very mild compared to the presently used methods to remove prions for example, from reusable medical equipment.

The inactivating component, or active agent, is best described functionally, as those skilled in the art reading this disclosure will contemplate other agents which could be used in a low pH composition to inactivate prions when the basic concepts and specific examples of the invention are described. Some general classes of compounds useful as the active agent include protein denaturants, inorganic salts; organic solvents, detergents and dendrimers.

Compositions are disclosed that, when added to food products, will inactivate any prions present and prevent infection. The compositions may also be used on livestock feed, to disinfect any prions in the livestock.

The antiseptic compositions of the invention can be combined with conventional antibacterial and antiviral agents in aqueous or alcohol solutions to produce disinfecting agents or surgical scrubs. Branched polycations for use in the invention include, but are not limited to, polyamidoamide (PAMAM), polypropyleneimine (PPI), and polyethyleneimine (PEI) dendrimers, poly(4'-aza-4'-methylheptamethylene D-glucaramide), polyamidoamines and suitable fragments and/or variants of these compounds. Although polycationic dendrimers can be used as the active agent in antiseptic formulations of the invention there are other more preferred compounds that inactivate prions in an acid environment. The essence of the invention is that a wide range of different types of compounds will render prions non-infectious in a relatively short period of time (e.g., 2 hours or less) when maintained at a pH of 4.0 or less at moderate temperatures, e.g., 4° C. to 37° C. In some cases, the commercial value of the invention is decreased if the composition does not accomplish its intended purpose in a short time period (e.g., less than 10 minutes at about room temperature (20±5° C.)).

An overall aspect of the invention is an antiseptic composition comprising an aqueous solvent, an acid capable of maintaining the composition at a preferred pH of 4.0 or less and an active component which at a low pH renders infectious prions non-infectious.

Another aspect of the invention is the use of a wide range of protein denaturants at low pH to inactivate prions.

An advantage of the invention is that proteins such as prions can be rendered non-infectious without the need for extreme physical conditions, such as exposure to heat over long periods of time, e.g., without the need for an exposure of 1–10 hours at 100°–200° C.

Another feature of the invention is that compositions can be useful while containing only very low concentrations of the prion-inactivating component such as SDS or polycationic dendrimers, e.g., 1% to 0.001%.

A further advantage of the invention is that conformationally altered protein such as prions can be rendered non-infectious with a method which need only consist of applying an active component such as SDS or a polycationic dendrimer preferably held at a pH of 4.5 or less.

An important aspect of the invention is an assay whereby multiple compounds can be quickly and easily tested for their ability to destroy the infectious character of prions while the compound and the prions are held in a low pH environment.

Another aspect of the invention is the use of the claimed compounds in livestock feed. This can prevent the transmission of prions from livestock to humans by eliminating prions from the livestock before slaughter.

A further aspect of the invention is the use of the claimed compounds to treat organs and tissues prior to transplantation, to eliminate any prions that may be present in the tissue that is to be transplanted.

A further aspect of the invention is the use of the claimed compounds to treat donated blood or blood products before transfusion.

A further aspect of the invention is to pre-treat suture wire with a composition of the invention before using on a patient.

These and other aspects, advantages, and features of the invention will become apparent to those persons skilled in the art upon reading the details of the compounds, and methods more fully described below.

DETAILED DESCRIPTION OF THE PREFERRED EMBODIMENTS

Before the present methods, objects and compositions are described, it is to be understood that this invention is not limited to the particular steps, devices or components described and, as such, may of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

The term "acid" is used to describe any compound or group of compounds that has one or more characteristics of (a) sour taste; (b) turns litmus dye red; (c) reacts with certain metals to form a salt; (d) reacts with certain bases or alkalines to form a salt. An acid comprises hydrogen and in water undergoes ionization so that $H_3O^+$ ions are formed, also written as $H^+$ and referred to as hydronium ions or simply hydrogen ions. Weak acids such as acetic acid or carbonic acid may be used as may strong acids such as hydrochloric acid, nitric acid and sulfuric acid (HCl, $H_2SO_4$, $H_2NO_3$). In compositions of the invention the acid is preferably present in a concentration so as to obtain a pH of about 5 or less, more preferably about 4 or less and still more preferably 3.5±1. The acid component of the antiseptic composition must be present in a concentration (molarity) to keep the composition in the desired pH range. The concentration (molarity) or the acid used will vary somewhat with the particular acid used, the solvent used (water or alcohol) and other factors such as temperature and pressure. The acid component is preferably present in sufficient molarity and is of such type that when the antiseptic composition of the invention is put into use (e.g., mixed with a sample to be disinfected) the composition remains within the preferred pH range. Thus, stronger and/or more concentrated forms of acids are preferred when the composition is to be used on or in a situation where the composition will be significantly diluted and/or contact a high pH (i.e., very basic) component.

The terms "active component," "active agent," "inactivating agent" and the like are used interchangeably herein to describe a compound or group of compounds which when combined in the "acid" component of the invention in the antiseptic composition will render a conformationally altered protein non-infectious. Preferably the active component is within an environment of a pH of about 5 or less, preferably 4 or less and in a low concentration e.g., less than 5% by volume of the composition, and with inactive prions or other conformationally altered proteins in two hours or less, at a temperature of 4° C. to 37° C. Active components can be determined using an assay of the invention whereby different compounds are tested for their ability to destroy infectivity. Preferred compounds that act as an active component for prions include SDS, urea, and a wide range of protein denaturants including guanidine and thiocynate as well as various branched polycations. Some non-limiting examples of compounds which could be used as the active component include the following:

1) Conventional protein denaturants including:
  a) urea;
  b) guanidine;
  c) guanidine hydrochloride;
  d) beta-mercaptoethanol;
  e) dithiothreitol (DTT); and
  f) chaotropes.
2) Inorganic salts including:
  a) lithium bromide;
  b) thiocyanate;
  c) potassium thiocyanate;
  d) sodium iodide;
  e) ammonium chloride, EDTA (metal chelator);
  f) lithium ion and salts thereof; and
  g) formic acid and salts thereof.
3) Organic solvents including:
  a) formamide;
  b) dimethylformamide;
  c) dichloro- and trichloroacetic acids and their salts; and
  d) trifluroethanolamine (TFE).
4) Detergents including:
  a) sodium dodecyl sulfate (SDS) (also known as lauryl sulfate, sodium salt—other salts are also useful including lithium and potassium salts;
  b) sodium cholate;
  c) sodium deoxycholate;
  d) octylglucoside;
  e) dodecyldimethylamine oxide;
  f) 3-[(3-cholamidopropyl)dimethylammonio]-1-propanesulfonate (CHAPS);
  g) dodecyltriethylammonium bromide (DTAB);
  h) cetyltrimethylammonium bromide (CTAB);
  i) polyoxyethylene-p-isooctylphenyl ether (e.g.,Triton X-20, Triton X-100, Triton X-114);
  j) alkyl sulfate; and
  k) alkyl sulfonate.
5) Branched Polycations including:
  a) polyamidoamide (PAMAM) dendrimers;
  b) polypropyleneimine (PPI) dendrimers;
  c) polyethyleneimine (PEI) dendrimers;
  d) poly (4'-aza-4'-methylheptamethylene D-glycaramide);
  e) polyamidoamines; and
  f) fragments and variants of any of a–e.

Further information of compounds and conditions effecting protein conformation can be found in Voet et al., *Biochemistry*, pp. 180–280 (1990); Scopes, R. K., *Protein Purification: Principles and Practice*, pp. 57–71 (1987); and Deutscher, M. P., *Guide to Protein Purification*, pp. 240–241 (1990).

The term "detergent" is used to mean any substance that reduces the surface tension of water. Examples of detergents are provided above as possible active components. The detergent may be a surface active agent which concentrates at oil-water interfaces, exerts emulsifying action and thereby aids in removing soils e.g., common sodium soaps of fatty acids. A detergent may be anionic, cationic, or monionic depending on their mode of chemical action. Detergents include linear alkyl sulfonates (LAS) often aided by "builders." A LAS is preferably an alkyl benzene sulfonate ABS that is readily decomposed by microorganisms (biodegradable). The LAS is generally a straight chain alkyl comprising 10 to 30 carbon atoms. The detergent may be in a liquid or a solid form.

The terms "prion," "prion protein," "infectious protein," "PrP$^{Sc}$ protein" and the like are used interchangeably herein to refer to the infectious PrP$^{Sc}$ form of a PrP protein, and is a contraction of the words "protein" and "infection." Particles are comprised largely, if not exclusively, of PrP$^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease," and feline spongiform encephalopathy of cats. Four prion diseases known to affect humans are: (1) kuru, (2) Creutzfeldt-Jakob Disease (CJD), (3) Gerstmann-Sträussler-Scheinker Disease (GSS), and (4) fatal insomnia (FI). As used herein "prion" includes all forms of prions causing all or any of these diseases or others in any animals used; and in particular in humans and domesticated farm animals.

The term "conformationally altered protein" is used here to describe any protein which has a three dimensional conformation associated with a disease. The conformationally altered protein may cause the disease, be a factor in a symptom of the disease or appear as a result of other factors. The conformationally altered protein appears in another conformation that has the same amino acid sequence. In general, the conformationally altered protein formed is "constricted" in conformation as compared to the other "relaxed" conformation, which is not associated with disease. Those skilled in the art reading this disclosure will recognize the applicability of the antiseptic composition of the invention to other conformationally altered proteins even though the invention is described in general as regards to prions.

The following is a non-limiting list of diseases with associated proteins, which assemble two or more different conformations, wherein at least one conformation is an example of a conformationally altered protein.

| Disease | Insoluble Proteins |
| --- | --- |
| Alzheimer's Disease | APP, Aβ peptide, α1-antichymotrypsin, tau, non-Aβ component, presenillin 1, presenillin 2, apoE |
| Prion diseases, Creutzfeldt-Jakob disease, scrapie and bovine spongiform encephalopathy | PrP$^{Sc}$ |
| ALS | SOD and neurofilament |
| Pick's disease | Pick body |
| Parkinson's disease | α-synuclein in Lewy bodies |
| Frontotemporal dementia | tau in fibrils |
| Diabetes Type II | Amylin |
| Multiple myeloma-plasma cell dyscrasias | IgGL-chain |
| Familial amyloidotic polyneuropathy | Transthyretin |
| Medullary carcinoma of thyroid | Procalcitonin |
| Chronic renal failure | β2-microglobulin |
| Congestive heart failure | Atrial natriuretic factor |

| Disease | Insoluble Proteins |
| --- | --- |
| Senile cardiac and systemic amyloidosis | Transthyretin |
| Chronic inflammation | Serum amyloid A |
| Atherosclerosis | ApoA1 |
| Familial amyloidosis | Gelsolin |
| Huntington's disease | Huntingtin |

The terms "sterilizing," "making sterile" and the like are used here to mean rendering something non-infectious or rendering something incapable of causing a disease. Specifically, it refers to rendering a protein non-infectious or incapable of causing a disease or the symptoms of a disease. Still more specifically, it refers to rendering a conformationally altered protein (e.g., PrP$^{Sc}$ known as prions) incapable of causing a disease or the symptoms of a disease.

By "effective dose" or "amount effective" is meant an amount of a compound sufficient to provide the desired sterilizing result. This will vary depending on factors such as (1) the active agent used, (2) the pH of the antiseptic composition, (3) the type of object or material being sterilized, and (4) the amount or concentration of infectious proteins which might be present. Polycations of the invention or more specifically polycationic dendrimer compounds of the invention could be mixed with a material in an amount in a range 1 to 500 µg of dendrimer per ml or mg of material being sterilized. The concentration is sufficient if the resulting composition is effective in decreasing (preferably eliminating) the infectivity of conformationally altered proteins such that the treated material over time would not result in infection. Because (1) some materials will have higher concentrations of altered protein than others; (2) some materials are contacted more frequently than others; and (3) individual proteins have different degrees of infectivity, the effective dose or concentration range needed to sterilize can vary considerably. It is also pointed out that the dose needed to treat an amount of material may vary somewhat based on the pH the treatment is carried out at and the amount of time the compound is maintained in contact with the material at the desired low pH (e.g., 4.5 or less) level and the surrounding temperature and pressure.

The term "LD$_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "amine-terminated" includes primary, secondary and tertiary amines.

The terms "PrP protein," "PrP" and like are used interchangeably herein and shall mean both the infectious particle form PrP$^{SC}$ known to cause diseases (spongiform encephalopathies) in humans and animals and the noninfectious form PrP$^{C}$ which, under appropriate conditions is converted to the infectious PrP$^{Sc}$ form.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) and U.S. Pat. No. 5,565,186, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^C$ (non-disease) or $PrP^{Sc}$ (disease) form.

The terms "standardized prion preparation," "prion preparation," "preparation" and the like are used interchangeably herein to describe a composition (e.g., brain homogenate) obtained from the brain tissue of mammals that exhibit signs of prion disease: the mammal may: (1) include a transgene as described herein; (2) have and ablated endogenous prion protein gene; (3) have a high number of prion protein gene from a genetically diverse species; and/or (4) be a hybrid with an ablated endogenous prion protein gene and a prion protein gene from a genetically diverse species. Different combinations of 1–4 are possible, e.g., (1) and (2). The mammals from which standardized prion preparations are obtained exhibit clinical signs of CNS dysfunction as a result of inoculation with prions and/or due to developing the disease of their genetically modified make up, e.g., high copy number of prion protein genes. Standardized prion preparations and methods of making such are described and disclosed in U.S. Pat. No. 5,908,969 issued Jun. 1, 1999 and application Ser. No. 09/199,523 filed Nov. 25, 1998.

By "organ" is meant a differentiated structure consisting of cells and tissues and performing some specific function in an animal.

By "tissue" is meant a group of cells similar to each other, along with their associated intercellular substances, which perform the same function within a multicellular organism. Major tissue types include epithelial, connective, skeletal, muscular, glandular, and nervous tissues.

The term "blood product" includes the red blood cells, white blood cells, serum or plasma separated from the blood.

The term "bodily fluid" encompasses blood, blood products, lymph, saliva, spinal fluid, semen, or any other fluid that originates in the body.

Abbreviations used herein include:

CNS for central nervous system;

BSE for bovine spongiform encephalopathy;

CJD for Creutzfeldt-Jakob Disease;

FFI for fatal familial insomnia;

GSS for Gerstmann-Sträussler-Scheinker Disease;

AD for Alzheimer's disease;

CAA for cerebral amyloid angiopathy;

Hu for human;

HuPrP for human prion protein;

Mo for mouse;

MoPrP for mouse prion protein;

SHa for a Syrian hamster;

SHaPrP for a Syrian hamster prion protein;

PAMAM for polyamidoamide dendrimers;

PEI for polyethyleneimine;

PK for proteinase K;

PPI for polypropyleneimine;

$PrP^{Sc}$ for the scrapie isoform of the prion protein;

$PrP^{C}$ for the cellular contained common, normal isoform of the prion protein;

PrP 27–30 or $PrP^{Sc}$ 27–30 for the treatment or protease resistant form of $PrP^{Sc}$;

$MoPrP^{Sc}$ for the scrapie isoform of the mouse prion protein;

N2a for an established neuroblastoma cell line used in the present studies;

ScN2a for a chronically scrapie-infected neuroblastoma cell line;

ALS for amyotrophic lateral sclerosis;

HD for Huntington's disease;

FTD for frontotemporal dementia;

SDS for sodium dodecyl sulfate; and

SOD for superoxide dismutase.

General Aspects of the Invention

The invention encompasses a range of antiseptic compositions, methods of rendering conformationally altered proteins non-infectious, and assays for determining compounds, which may be used as active agents. The composition is comprised of an acid component and an active component, although a single compound could serve the function of both components. The composition preferably comprises a solvent carrier component that is generally alcohol or aqueous based. The acid component is characterized by maintaining the pH of the composition at 5.0 or less and preferably at 4.0 or less when in use. The active component is characterized by rendering infectious proteins non-infectious. Preferably, the active component in the low pH environment of the composition renders infectious proteins non-infectious in two hours or less at a temperature of 40° C. or less.

Suitable acid components include a non-toxic weak acid such as acetic acid having dissolved therein an active component such as a branched polycation. Compositions of the invention may be in the form of aqueous or alcohol solutions, which are comprised of a branched polycation, an antibacterial, an antifungal and an antiviral compound. The antiseptic compositions are coated on, mixed with, injected into or otherwise brought into contact with a material to be sterilized. The composition is applied in a manner so that the branched polycation is maintained at a low pH (e.g., 5 or less, and preferably 3.5±1) in an amount of 1 $\mu$g or more polycation per ml or mg of material to be sterilized. The composition is maintained in the desired pH range at a temperature of 4° C. to 37° C., for a sufficient period of time (e.g., preferably about 2 hours or less) to cause conformationally altered protein present on or in the material to be destroyed (e.g., hydrolyzed) or rendered non-infective. Preferred compositions of the invention are useful in cleaning and sterilizing and may be comprised of an active agent such as SDS or polycationic dendrimers, a detergent, and an acid component providing a pH less than 3.5.

Dendrimer Compounds that Clear Prions

Dendrimers are branched compounds also known as "starburst" or "star" polymers due to a characteristic star-like structure (see FIG. 1). Dendrimers of the invention are polymers with structures built from $AB_n$ monomers, with n 2 and preferably n=2 or 3. Such dendrimers are highly branched and have three distinct structural features: 1) a core, 2) multiple peripheral end-groups, and 3) branching units that link the two. Dendrimers may be cationic (fill generation dendrimers) or anionic (half-generation dendrimers). For a review on the general synthesis, physical properties, and applications of dendrimers, see, e.g., Tomalia et al., Angew *Chem. Int. Ed. Engl.* 29:138–175, (1990); and Y. Kim and C. Zimmerman, *Curr. Opin. Chem. Biol.* 2:733–7421 (1997).

In a preferred embodiment, sterilizing compositions of the invention comprise a cationic dendrimer preferably dissolved in a low pH solvent such as acetic acid. Examples of suitable dendrimers are disclosed in U.S. Pat. Nos. 4,507, 466, 4,558,120, 4,568,737, 4,587,329, 4,631,337, 4,694,064, 4,713,975, 4,737,550, 4,871,779, and 4,857,599. Dendrimers typically have tertiary amines that have a pKa of 5.7. The dendrimers can optionally be chemically or heat treated to remove some of the tertiary amines. Other suitable cations include polypropylene imine, polyethyleneimine (PEI), which has tertiary amines with a pKa of 5.9, and poly(4'-aza-4'-methylheptamethylene D-glucaramide), which has tertiary amines with a pKa of 6.0. The cationic dendrimer is preferably dissolved in the low pH solvent such as vinegar in a concentration of 0.0001% or more, preferably 0.01% or more preferably about 1%.

Preferably, the dendrimers for use in the invention are polyamidoamines (hereinafter "PAMAM"). PAMAM dendrimers are particularly biocompatible, since polyamidoamine groups resemble peptide bonds of proteins.

Dendrimers are prepared in tiers called generations (see, generations 0, 1 and 2 in FIG. 1) and therefore have specific molecular weights. The fall generation PAMAM dendrimers have amine terminal groups, and are cationic, whereas the half-generation dendrimers are carboxyl terminated. Full generation PAMAM dendrimers are thus preferred for use in the present invention. PAMAM dendrimers may be prepared having different molecular weights and have specific values as described in Table 1 below for generations 0 through 10.

TABLE 1

PAMAM Dendrimers And Their Molecular Weights
(Ethylene Diamine core, amine terminated)

| Generation | Terminal Groups | Mol. Wt. g/mol |
|---|---|---|
| 0 | 4 | 517 |
| 1 | 8 | 1430 |
| 2 | 216 | 3256 |
| 3 | 32 | 6909 |
| 4 | 64 | 14,215 |
| 5 | 128 | 28,795 |
| 6 | 256 | 58,048 |
| 7 | 512 | 116,493 |
| 8 | 1024 | 233,383 |
| 9 | 2048 | 467,162 |
| 10 | 4096 | 934,720 |

Table 1 shows the number of terminal amine groups for PAMAM dendrimers, generations 0 through 10, range from 4 to 4,096, with molecular weights of from 517 to 934,720. PAMAM dendrimers are available commercially from Aldrich or Dendritech. Polyethyleneimine or polypropylene dendrimers or quaternized forms of amine-terminated dendrimers may be prepared as described by Tomalia et al., *Angew Chem. Int. Ed. Engl.* 29:138–175 (1990).

Sterilizing Compositions

Examples provided herein show that various active compounds such as SDS or highly-branched polycations, e.g., dendrimer compounds, at a pH of 4.0 or less affect the extent and distribution of PrP$^{Sc}$ protein deposits in scrapie-infected cells. The presence of these active compounds in a low pH environment and at relatively low, non-cytotoxic levels results in a significant reduction in detectable PrP$^{Sc}$ in cells and brain homogenates. Thus, the present invention encompasses compositions for reducing, inhibiting, or otherwise mitigating the degree of infectivity of a protein. A composition of the invention is comprised of any compound capable of destroying conformationally altered proteins when in a low pH environment (e.g., a detergent such as SDS or a polycationic dendrimer) in solution, suspension or mixture.

Sterilizing Formulations

Sterilizing compositions of the invention preferably contain the active component in a concentration from 0.0001 to 10% of the formulation. The following methods and excipients are merely exemplary and are in no way limiting.

In addition to including the active compound in the formulation it is important to maintain that compound in a low pH environment. Any number of known acids or mixtures of acids could be used with the invention. Non-limiting examples of commercially available products, which could be supplemented with the cationic compounds, are described below. In these formulations, the percentage amount of each ingredient can vary. In general, a solvent ingredient (e.g., water or alcohol) is present in amounts of 40% to 100%. The other ingredients are present in an amount in a range of 1% to 60% and more generally 5% to 20%. In each case the polycationic compounds of the invention are added in amounts of about 0.01% to 5% and preferably 0.1% to 2% and more preferably about 1%. The amount added is an amount needed to obtain the desired effect.

| Component | wt % |
|---|---|
| FORMULATION 1 | |
| Acid | 90–99.99 |
| Active component | 0.01–10 |
| FORMULATION 2 | |
| Acid | 90–99.99 |
| Protein denaturant | 0.01–10 |
| FORMULATION 3 | |
| Acid | 90–99.99 |
| Inorganic salt | 0.01–10 |
| FORMULATION 4 | |
| Acid | 90–99.99 |
| Organic solvent | 0.01–10 |
| FORMULATION 5 | |
| Acid | 90–99.99 |
| Detergent | 0.01–10 |
| FORMULATION 6 | |
| Water | 10–99 |
| Acid | 1–20 |
| Active component of any of 1–5 | 0.01–10 |
| FORMULATION 7 | |
| Water | 10–98 |
| Acid | 1–20 |
| Detergent | 1–20 |
| Polycationic dendrimer | 0.01–5 |
| FORMULATION 8 | |
| Water | 10–98 |
| Acetic acid | 1–20 |
| Linear alkyl sulfonate | 1–20 |
| Polycationic dendrimer | 0.01–5 |
| FORMULATION 9 | |
| Water | 10–99 |
| Acetic acid | 1–20 |
| SDS | 0.01–10 |
| FORMULATION 10 | |
| Water | 1–98 |
| Alcohol | 0–98 |
| Acid | 1–20 |
| Detergent | 1–20 |
| Polycationic dendrimer | 0.1–5 |

-continued

| Component | wt % |
|---|---|
| FORMULATION 11 | |
| Water | 1–99 |
| Acid | 1–20 |
| Antibacterial | 0.1–5 |
| Detergent | 1–20 |
| Polycationic dendrimer | 0.1–5 |
| FORMULATION 12 | |
| Water | 3–98.889 |
| Antimicrobial active agent | 0.001–5 |
| Anionic surfactant | 1–80 |
| Proton ($H^+$) donating agent | 0.1–12 |
| Polycationic dendrimer | 0.01–5 |
| FORMULATION 13 | |
| Polycationic dendrimer | 0.5 |
| Ethanol | 74.0 |
| Benzalkonium chloride | 0.2 |
| CAE | 0.02 |
| Glycerine | 1.0 |
| Chain silicone | 0.5 |
| Triglyceride | 0.5 |
| Lactic acid | 10.0 |
| Purified water | 13.28 |
| FORMULATION 14 | |
| Polycationic dendrimer | 1.0 |
| Ethanol | 75.0 |
| Benzalkonium chloride | 0.2 |
| CAE | 0.02 |
| Glycerine | 1.0 |
| Cyclic silicone | 0.2 |
| Triglyceride | 0.3 |
| Acetic Acid | 20.0 |
| Purified water | 2.28 |
| FORMULATION 15 | |
| Polycationic dendrimer | 0.25 |
| Ethanol | 74.0 |
| Chlorhexedine gluconate | 0.75 |
| Benzalkonium chloride | 0.2 |
| CAE | 0.02 |
| Glycerine | 2.0 |
| Chain silicone | 0.2 |
| Cyclic silicone | 0.2 |
| Triglyceride | 0.3 |
| Acetic Acid | 20.0 |
| Purified water | 2.08 |
| FORMULATION 16 | |
| Polycationic dendrimer | 0.1 |
| Ethanol | 75.0 |
| Chlorhexedine gluconate | 0.9 |
| Benzalkonium chloride | 0.2 |
| CAE | 0.02 |
| Glycerine | 1.0 |
| Chain silicone | 0.5 |
| Cyclic silicone | 0.5 |
| Triglyceride | 0.3 |
| Lactic acid | 14.0 |
| Purified water | 7.98 |
| FORMULATION 17 | |
| Polycationic dendrimer | 0.01 |
| Ethanol | 75.0 |
| Benzalkonium chloride | 0.2 |
| CAE | 0.02 |
| Glycerine | 2.0 |
| Chain silicone | 0.99 |
| Cyclic silicone | 2.0 |
| Triglyceride | 3.0 |
| Lactic acid | 9 |
| Purified water | 7.78 |
| FORMULATION 18 | |
| Polycationic dendrimer | 1 |
| Ethanol | 75.0 |
| Chlorhexedine gluconate | 0.2 |
| Benzalkonium chloride | 0.2 |
| CAE | 0.02 |
| Glycerine | 0.8 |
| Chain silicone | 0.2 |
| Cyclic silicone | 0.2 |
| Triglyceride | .38 |
| Acetic acid | 10 |
| Purified water | 12 |
| FORMULATION 19 | |
| Polycationic dendrimer | 0.001 |
| Ethanol | 75.99 |
| Chlorhexedine gluconate | 0.2 |
| CAE | 0.02 |
| Glycerine | 1.0 |
| Chain silicone | 0.2 |
| Triglyceride | 0.3 |
| Lactic acid | 14 |
| Purified water | 8.28 |
| FORMULATION 20 | |
| Polycationic dendrimer | 1 |
| Ethanol | 75.0 |
| Benzalkonium chloride | 0.2 |
| CAE | 0.02 |
| 1,3-butylene glycol | 1.0 |
| Metylphenyl polysiloxane | 0.2 |
| Isopropyl myristate (IPM) | 0.3 |
| Purified water | 22.28 |
| FORMULATION 21 | |
| Water | 1–98 |
| Alcohol | 0–98 |
| Acid | 1–20 |
| SDS | 1–20 |
| FORMULATION 22 | |
| Water | 1–99 |
| Acid | 1–20 |
| Antibacterial agent | 0.1–5 |
| Detergent | 1–20 |
| FORMULATION 23 | |
| Water | 3–98.889 |
| Antimicrobial active agent | 0.001–5 |
| Anionic surfactant | 1–80 |

| Component | wt % |
|---|---|
| Proton (H⁺) donating agent | 0.1–12 |
| SDS | 0.01–5 |

FORMULATION 24

| Component | wt % |
|---|---|
| SDS | 0.5 |
| Ethanol | 74.0 |
| Benzalkonium chloride | 0.2 |
| CAE | 0.02 |
| Glycerine | 1.0 |
| Chain silicone | 0.5 |
| Triglyceride | 0.5 |
| Lactic acid | 10.0 |
| Purified water | 13.28 |

FORMULATION 25

| Component | wt % |
|---|---|
| Urea | 1.0 |
| Ethanol | 75.0 |
| Benzalkonium chloride | 0.2 |
| CAE | 0.02 |
| Glycerine | 1.0 |
| Cyclic silicone | 0.2 |
| Triglyceride | 0.3 |
| Acetic Acid | 20.0 |
| Purified water | 2.28 |

FORMULATION 26

| Component | wt % |
|---|---|
| Guanidine hydrochloride | 0.25 |
| Ethanol | 74.0 |
| Chlorhexedine gluconate | 0.75 |
| Benzalkonium chloride | 0.2 |
| CAE | 0.02 |
| Glycerine | 2.0 |
| Chain silicone | 0.2 |
| Cyclic silicone | 0.2 |
| Triglyceride | 0.3 |
| Acetic Acid | 20.0 |
| Purified water | 2.08 |

FORMULATION 27

| Component | wt % |
|---|---|
| Thiocynate | 0.1 |
| Ethanol | 75.0 |
| Chlorhexedine gluconate | 0.9 |
| Benzalkonium chloride | 0.2 |
| CAE | 0.02 |
| Glycerine | 1.0 |
| Chain silicone | 0.5 |
| Cyclic silicone | 0.5 |
| Triglyceride | 0.3 |
| Lactic acid | 14.0 |
| Purified water | 7.98 |

FORMULATION 28

| Component | wt % |
|---|---|
| Sodium deoxycholate | 0.01 |
| Ethanol | 75.0 |
| Benzalkonium chloride | 0.2 |
| CAE | 0.02 |
| Glycerine | 2.0 |
| Chain silicone | 0.99 |
| Cyclic silicone | 2.0 |
| Triglyceride | 3.0 |
| Lactic acid | 9 |
| Purified water | 7.78 |

FORMULATION 29

| Component | wt % |
|---|---|
| SDS | 1 |
| Ethanol | 75.0 |
| Chlorhexedine gluconate | 0.2 |
| Benzalkonium chloride | 0.2 |
| CAE | 0.02 |
| Glycerine | 0.8 |
| Chain silicone | 0.2 |
| Cyclic silicone | 0.2 |
| Triglyceride | .38 |
| Acetic acid | 10 |
| Purified water | 12 |

FORMULATION 30

| Component | wt % |
|---|---|
| SDS | 0.001 |
| Ethanol | 75.99 |
| Chlorhexedine gluconate | 0.2 |
| CAE | 0.02 |
| Glycerine | 1.0 |
| Chain silicone | 0.2 |
| Triglyceride | 0.3 |
| Lactic acid | 14 |
| Purified water | 8.28 |

FORMULATION 31

| Component | wt % |
|---|---|
| Sodium Acetate pH 4.0 ± 1 | 10% |
| SDS | 4% |
| Water | 86% |

FORMULATION 32

| Component | wt % |
|---|---|
| SDS | 4% |
| Peracetic acid | 0.1–10% |
| Water | 86–95.9% |

FORMULATION 33

| Component | wt % |
|---|---|
| SDS | 4% |
| Glycerine | 10% |
| Water | 86% |

FORMULATION 34

| Component | wt % |
|---|---|
| SDS | 1–20% |
| Acid pH 4.0 ± 1 | 1–20% |
| Water | 60–98% |

FORMULATION 35

| Component | wt % |
|---|---|
| SDS | 1–20% |
| Base pH 10.0 ± 1 | 1–20% |
| Water | 60–98% |

FORMULATION 36

| Component | wt % |
|---|---|
| SDS | 1 |
| Ethanol | 75.0 |
| Benzalkonium chloride | 0.2 |
| CAE | 0.02 |
| 1,3-butylene glycol | 1.0 |
| Metylphenyl polysiloxane | 0.2 |
| Isopropyl Myristate (IPM) | 0.3 |
| Purified water | 22.28 |

By using the disclosure provided here and other information such as taught in U.S. Pat. Nos. 5,767,054; 6,007,831; 5,830,488; 5,968,539; 5,416,075; 5,296,158; and patents and publications cited therein, those skilled in the art can produce countless other formulations of the invention. Further, the formulations are preferably adjusted to have a pH of less than 4.0, and such formulations can be used as described in such publications and can be packaged in any suitable container or dispenser device, e.g., taught in U.S. Pat. No. 5,992,698. The pH can be lowered with any acid, e.g., HCl, $H_2SO_4$, $H_2NO_3$ peracetic acid, etc., and can be used as the acid component in the formulae provided above.

Example 17, discussed below, shows that compounds such as SDS are effective in denaturing $PrP^{Sc}$ not only at a low pH (e.g., 5 or less) but also are effective at a high pH (e.g., 9 or more), while generally not effective at a pH of about 7.0±1. The pH of the formulation can be adjusted to obtain desired results in each particular use. For example, a very high or very low pH may be best for inactivating $PrP^{Sc}$; these extreme pH's may be undesirable in some situations due to their corrosive effects. Thus, a preferred pH is one that inactivates $PrP^{Sc}$ and has the least possible adverse effects for the intended use. In many situations a preferred pH for an SDS formulation is about 4.0±1 or about 10.0±1.

Formulations of the invention used with a cell culture have the advantage that they are non-toxic. For example, parenteral administration of a solution of the formulations of the invention is preferably nontoxic at a dosage of 0.1 mg/mouse, which is an $LD_{50}$ of less than one at 40 mg/kg. Various nutrient formulations and/or injectable formulations of the type known to those skilled in the art can be used to prepare formulations for treating cell cultures.

Those skilled in the art will understand that in some situations it may be desirable to further reduce the pH environment to obtain the desired results. This can be accomplished by adding any desired acid. If desired, the pH can be raised to a normal level after treatment is complete, i.e., after a sufficient amount of any conformationally altered protein present is destroyed.

Compounds effective in sterilizing compositions containing conformationally altered proteins are determined via a cell culture assay and an organ homogenate assay each of which is described below in detail.

Livestock Feed

An important application of the invention is a composition that renders prions non-infectious and/or prevents prion formation and/or aids in the denaturation of prions from a mammal when combined with a livestock feed. In particular, a composition of the invention is combined with a livestock feed, which is derived from an animal source such as meat or bone meal and more particularly animal material, which includes ground material from the central nervous system from another animal. However, the compounds of the invention can be combined with plant-derived materials used in livestock feed in order to render prions non-infectious and/or prevent or treat prion infections in the animal eating the feed. More particularly, the compounds of the present invention can be added to livestock feed or feedstuffs used to feed any type of livestock. The feedstuff compositions disclosed herein are intended to provide nutritional requirements of a variety of animals, including cattle, poultry, swine, sheep, goats, other monogastric or ruminant livestock. The composition generally varies according to the type of animals to which the feedstuff will be given.

Examples of various animal feedstuff components can be found in U.S. Pat. Nos. 6,207,217, 6,203,843, 5,786,007, 4,225,621, 4,161,543 and 4,062,988, the disclosures of which are herein incorporated by reference.

Generally, when the term "feedstuff" is used with respect to the present invention, the term comprises all types of plant and animal components. Specifically, "feedstuff" includes organic components such as proteins, crude fiber, acid detergent fiber, neutral detergent fiber, vitamins and minerals. Typical compositions of feedstuffs for livestock include, but are not limited to, the following components: alfalfas, ammonium sulfate, barleys, beet pulps, blood meal, bluestem grass, brewers grains and yeast, brome grass, calcium carbonate, canary grass, carrot pulp, roots and tops, cattle manure, cheatgrass, clovers, coffee grounds, corn and corn plants, cottonseed, defluorinated phosphate, diammonium phosphate, dicalcium phosphate, distillers grain barley, distillers grain corn, feathermeal hydrolyzed, garbage (municipal), grain screenings and grain dust, grape pomace, grass silage, hominy feed, hop leaves, vines and spent hops, limestone, linseed meal, all types of hay including meadow hay, meat and bone meal (MBM), milo grain, mint slug silage, molasses beet, cane, citrus and wood, monoammonium phosphate, mono-dicalcium phosphate, navy beans, all types of oats including oat hay, oat silage, oat straw, oat grain, groats, oat meal, oat mill byproducts and oat hull, orange pulp, orchard grass, pea vines, peanut hulls, skins and meal, potato vine, potatoes and potato waste, poultry fat and poultry litter and manure, prairie hay, rapemeal solvent, rye straw and grain, safflower meal, sagebrush, sorghum stover and silage, soybeans and soybean hull, sudangrass hay and silage, sunflower meal and hulls, timothy hay and silage, tomatoes, triticale silage, urea, wheat bran, wheat grass, wheat grain, wheat shorts and wheat straw.

Further, the above feedstuff components are set forth above, serve merely as examples and are not intended to be comprehensive or limiting. As such, suitable feedstuffs for the present invention may comprise additional components not provided in the list above.

Of the above listed feed components, meat and bone meal (MBM) stands out as one the richest sources of energy and minerals. Typically, the crude protein content of MBM is about 50%. Hamilton, C. R., "Meat and Bone Meal," Esteem Products. Vol. 1(1). MBM is thus one of the most efficient feed components. MBM is produced as a by-product from the removal of fat from animal tissues through rendering. The rendering process produces a finely ground, dry residue of animal by-products pressure cooked and stabilized by high temperature steam in closed tanks. The fat can be skimmed off and the solid residue is pressed to remove as much of the fat and water as possible. As defined and regulated by the Association of American Feed Control Officials (AAFCO), MBM is the rendered product from mammal tissues, including bone, exclusive of any added blood, hair, hoof, horn, hide trimmings, manure, stomach and rumen contents, except in such amounts as may occur unavoidably in good processing practices. As such, neuronal tissues are included in MBM products. (See, "The BSE Inquiry" § 9.15 at http://www.bse.org.uk/report/volume7/chapteh2.htm).

The invention comprises feedstuff as defined herein, in combination with a composition that inhibits prion formation. A composition of the invention is added to feedstuff and fed to an animal, and in particular to domesticated livestock farm animals such as cows, pigs, sheep, goats, horses, chickens etc. The active component is added in an amount sufficient to "treat" the animal. The amount will vary based on factors such as the type of animal and its size. In general, dosing is such that the animal will receive about 10 mg to about 10,000 mg/day/kg of weight of the animal.

Blood and Blood Products

A further aspect of the invention is the use of the claimed compounds and methods to treat blood and blood products prior to transfer to a recipient. Application of the composition of the invention renders prions non-infectious and/or prevents prion formation and/or aids in the denaturation of prions from blood and blood products. Approximately 14 million blood donations occur every year in the United States. About 12 million units of whole blood are transfused annually. There have been chronic shortages of blood, partly because of increased demand from modern surgical techniques. For example, people who are undergoing aggressive cancer chemotherapy treatments require blood transfusions because their own body's ability to make blood cells diminishes. Premature infants may require blood transfusions to carry oxygen throughout their bodies. Medical treatments, such as organ transplants and cardiac bypass surgery, that require a large amount of blood, were uncommon 20 years ago, yet today are routine. And the aging of the population means that more people live longer and are more likely to need medical treatments that require safe blood and blood products. Last year the American Red Cross, which provides one-half of the nation's blood supply to patients throughout the country, collected more than 6.3 million volunteer blood donations. However, the demand for blood has been increasing even faster than the supply.

Compounding the problem of low blood supply is the emergence of Creutzfeldt-Jakob Disease. Many potential blood donors are now excluded from donating because of the risk of prior exposure to the disease. There is some evidence to date that CJD can be transmitted through blood transfusions, however no cases have been found in the United States. The evidence is not definitive, however, and questions remain as to whether or not there are prions in the U.S. blood supply. In response to this threat, the U.S. Food and Drug Administration is implementing a ban on donations from people who have spent more than ten years in France, Portugal, or Ireland since 1980. People who have spent more than six months in Great Britain from 1980–1996 are already forbidden from giving blood in the United States, Canada, New Zealand, and Australia. At present, there is no commercial diagnostic test for detecting prions in the blood of humans or other animals. Humans may be infected with prions for five to twenty years before symptoms appear, which means that the U.S. blood supply could already be tainted with prions.

Further restrictions on donors will exacerbate an already critical shortage of donated blood in the United States. Because of the possibility of transferring prions via blood and plasma transfusions, the instant invention is useful in preventing the transfer of prions in the blood supply by disinfecting the existing supply of blood and blood products. This would decontaminate any prions in the existing blood supply, and would also allow more people to donate blood who are unable to do so at the present time because of the current restrictions.

Suitable procedures for removing prions from blood may be found in Pruisner et al., U.S. Pat. No. 6,221,614. The procedure generally encompasses exposure of the blood or blood product to a complexing agent that usually is immobilized on a solid surface. Prions present in the blood or blood product will complex to the complexing agent, which is then removed from the sample, and the filtered blood or blood product is then free of any prion infection.

The blood should be treated preferably at room temperature (15° C. to 30° C.). The solution should have a pH of about 6.4 to 8.4, preferably 7.4, and should not contain excess magnesium or calcium. A sample is then exposed to a complexing agent, which is immobilized on a solid surface or otherwise provided in a manner allowing separation of the prion-bound complexing agent from the sample. The complexing agent forms a complex with, or somehow binds preferentially with, or exclusively to any constricted form (generally a pathogenic PrP$^{Sc}$ form) of the protein present in the sample, thus effectively immobilizing any PrP$^{Sc}$ present in the sample to the solid surface upon exposure of the sample to the immobilized complexing agent.

In one embodiment, a chemical agent such as a heteropoly acid (e.g. PTA), or preferably a metallic salt thereof (NaPTA) is immobilized to a solid surface such as a membrane filter, a magnetic bead, and the like. The sample is subjected to a complexing agent over a period of time sufficient to allow substantially all the PrP$^{Sc}$ in the sample to complex with the PTA. For example, the sample could be incubated at about 30° C. to 45° C. (preferably 37° C.) over a period of from about 1 to 16 hours. The complexing agent forms a complex with the PrP$^{Sc}$. What is important is that complex formed can be separated away from the rest of the sample by some means, e.g., filtration, use of magnetic field, sedimentation and the like.

The present invention may be used to treat a biological sample wherein the PrP$^{Sc}$ or other pathogenic protein is substantially removed from the sample, and preferably to levels at which the PrP$^{Sc}$ is undetectable by conventional means. Methods of removal of the PrP$^{Sc}$ will aid in preventing transmission of PrP$^{Sc}$-mediated disorders by providing biological samples that are substantially free from infectious levels of prions, i.e., "prion free." Further, any prions not removed from the sample after treatment with a composition of the invention are rendered non-infectious.

It is not possible to precisely determine the conditions under which the infectivity of an infectious protein such as a prion can be eliminated or the conditions under which the pathogenic proteins being treated will be denatured. Such will vary depending on the particular active component being utilized. However, an important aspect of the invention is that the active component be able to eliminate infectivity or denature an infectious protein such as prions under relatively mild conditions. In general, these conditions include a pH of about 5 or less at a temperature above 4° C. for a period of time of about 2 hours or more. However, it is not necessary generally to raise the temperature above 100° C. and it is generally possible to inactivate infectivity or denatured proteins in a range of 20 to 100° C. or more preferably 37° C. to 80° C. or still more preferably in a range of about 10° C. to 60° C. at a pH in a range of about 3 to 5 over a period of about 2 hours or less and more preferably 1 hour or less.

Complexing Agents

Compounds that are useful as complexing agents in the present invention include antibodies, enzymes, peptides, chemical species, binding molecules, etc. These complexing agents are used in a manner that allows binding and removal of prions from a biological solution, while maintaining the essential elements of the biological material intact, e.g. retention of cellular morphology and protein integrity. Such complexing agents may be used in whole blood, in blood components such as plasma and platelets, and in other biological fluids, as will be apparent to one skilled in the art.

Chemical Agents

In one embodiment of the prion removal pre-treatment step of the invention, the compound for removal of prions from a biological material is a chemical agent that precipitates PrP$^{Sc}$. One preferred class of chemical agents for use as complexing agents in the present invention are heteropoly acids and salts thereof. Heteropoly acids are fully or partially protonated forms of oxyanions having at least one central element and at least one coordinating element. Heteropoly acids may have the Keggin or Dawson structures.

A particular class of heteropoly acids is the protonated form of heteropolymolybdates. These anions contain from 2 to 18 hexavalent molybdenum atoms around one or more central atoms. About 36 different elements have been identified as central atoms of these heteropolymolybdates. These anions are all highly oxygenated. Examples of heteropolymolybdates include $[PMo_{12}O_{40}]^{3-}$, $[As_2Mo_{18}O_{62}]^{6-}$, and $[TeMo_6O_{24}]^{6-}$, where the central atoms are $P^{5+}$, $As^{5+}$, and $Te^{6+}$, respectively. A more detailed discussion of heteropolymolybdates is provided in the Kirk-Othmer Encyclopedia of Chemical Technology, 3rd ed., 15, pp. 688–689 (1981).

Another class of heteropoly acids, which is analogous to the protonated form of heteropolymolybdates, is the protonated form of heteropolytungstates. In heteropolytungstates, the coordinating element is tungsten instead of molybdenum. See, U.S. Pat. No. 4,376,219. The central elements of these heteropoly acids may be selected from the group consisting of P, Si, B, Ge, As, Se, Ti, Zr, Mn, F, V, Ce, and Th. The coordinating elements of these heteropoly acids include Mo and/or W. Optional coordinating elements include V, Mn, Co, In, Cub, An, and Fe. The ratio of the number of the coordinating elements to the number of central elements may be from 2.5 to 12, preferably from 9 to 12. Particular heteropoly acids, which are exemplified in U.S. Pat. No. 4,376,219, include phosphotungstic acid, silicotungstic acid, 10-tungsto-2-vanadophosphoric acid, 6-tungsto-6-molybdophosphoric acid, phosphomolybdic acid, silicomolybdic acid, germanotungstic acid, tungstofluoric acid, and 18-tungsto-2-phosphoric acid, as well as salts of all or any of these acids, e.g., metal salts such as Na, K, Mg, and Ca salts. A particular heteropoly acid for use in the present invention is phosphotungstic acid, i.e., $H_3PW_{12}O_{40}$ and its metal salts particularly Na salts. Such complexing agents effectively bind to $PrP^{Sc}$.

Such chemical agents may be used alone, in combination, or with other non-bioactive chemicals such as buffers and inert binding chemicals. Heteropoly acids of the invention (e.g., PTA) are preferably, although not exclusively, used in a metallic salt form. The metallic salt includes, but is not limited to, sodium, potassium, calcium and the like.

The amount of heteropoly acid or salt thereof which is combined and/or coated onto a support material is an amount sufficient to significantly remove $PrP^{Sc}$ from the a biological fluid, and preferably in an amount sufficient to remove $PrP^{Sc}$ to undetectable levels or at least non-infectious levels. The weight ratio of heteropoly acid to support material may be, for example, from about 1:20 to about 1:1. The heteropoly acid may be combined with the support material in any manner, which provides adequate dispersion of the heteropoly acid, thereby increasing the effective surface area of the heteropoly acid. A preferred technique for combining these components is by impregnation of the support material with the heteropoly acid. The heteropoly acid may also be combined with the support material by an ion exchange technique. The impregnation technique may involve sorbing an aqueous solution of the heteropoly acid into the porous region of the support material followed by drying to remove water and to leave behind supported heteropoly acid. Other methods of immobilizing heteropoly acids or salts thereof may be used to immobilize these complexing agents, as will be apparent to one skilled in the art upon reading this disclosure.

Biological Agents

In another embodiment, the complexing agent is a protein, peptide, or other biological moiety that selectively binds to $PrP^{Sc}$.

In one embodiment, the complexing agents are peptides or other small molecules designed to selectively bind to prions. Preferably, the peptides or small molecules are designed to preferentially bind to $PrP^{Sc}$. By "preferentially bind" is meant that the peptide is designed to be at least 20 times or more, more preferably 50 times or more, more preferably 100 times or more, and even more preferably 1000 times or more likely to bind to $PrP^{Sc}$ than to other proteins in the biological solution. Peptides of the invention are preferably designed to bind to the native form of $PrP^{Sc}$, as opposed to the denatured form, since the biological fluids generally contain $PrP^{Sc}$ in native form. Peptides may be designed to maximize binding to $PrP^{Sc}$ by designing the peptides to areas of $PrP^{Sc}$ that are more accessible to binding, as can be predicted by one skilled in the art. Useful antibodies that bind $PrP^{Sc}$ are disclosed and described in U.S. Pat. No. 5,846,533. Portions of these antibodies, which bind to $PrP^{Sc}$ are peptides which can be bound to a support surface and used in the present invention.

Alternatively, peptides may be designed to bind selectively to $PrP^C$ or to both $PrP^{Sc}$ and $PrP^C$. Although the $PrP^{Sc}$ form of the PrP protein is the infectious form, removal of the normal cellular prion proteins can also effectively halt or slow the progression of a prion-mediated disorder.

The complexing agent of the invention may also be an antibody selective for prions. This antibody may be directly immobilized or may be bound to another component (e.g., a high density metal). That antibody may bind to $PrP^{Sc}$, e.g., the antibody disclosed in U.S. Pat. No. 5,846,533. To remove $PrP^C$ present in the sample, an antibody that binds selectively or exclusively to $PrP^C$ may be used. Such an antibody is disclosed in U.S. Pat. No. 4,806,627, issued Feb. 21, 1989, disclosing monoclonal antibody 263K 3F4, produced by cell line ATCC HB9222 deposited on Oct. 8, 1986. The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies that bind to either $PrP^C$ or $PrP^{Sc}$ are disclosed in U.S. Pat. No. 5,846,533. Any antibody binding to $PrP^C$ and not to $PrP^{Sc}$ can be used, and those skilled in the art can generate such using known procedures, e.g., see methods of producing phage display antibody libraries in U.S. Pat. No. 5,223,409. Polyclonal anti-PrP antibodies have though been raised in rabbits following immunization with large amounts of formic acid or SDS-denatured SHaPrP 27–30. The antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP (Rogers et al. (1993) *Proc. Natl. Acad. Sci. USA* 90:3182–3186).

It is not entirely clear why many antibodies of the type described in the above cited publications will bind to $PrP^C$ and treated or denatured $PrP^{Sc}$ but not to native $PrP^{Sc}$. Without being bound to any particular theory, it is believed that such may take place because epitopes that are exposed when the protein is in the $PrP^C$ conformation are unexposed or partially hidden in the $PrP^{Sc}$ configuration—where the protein is relatively insoluble and more compactly folded together.

For purposes of the invention, an indication that no binding occurs means that the equilibrium or affinity constant $K_a$ is $10^6$ 1/mole or less. Further, binding will be recognized as existing when the $K_a$ is at $10^7$ 1/mole or greater, preferably $10^8$ 1/mole or greater. The binding affinity of $10^7$ 1/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four-fold differential in binding affinity may be accomplished by using several different antibodies as per (1)–(3) above and as such some of the antibodies in a mixture could have less than a four-fold difference.

A variety of different methods may be used with one or more different antibodies. Those of skill in the art will recognize that antibodies may be labeled with known labels and used with currently available robotics, sandwich assays, electronic detectors, flow cytometry, and the like. Further, the antibodies may be bound to denser components directly or via other intermediates such as anti-antibodies.

Methods of Purification

The complexing agent used in an initial clean-up or pre-treatment step of the invention, may be used in a variety of purification procedures to effectively remove prions from a biological material. A number of methods for use in the present invention are summarized as follows.

Affinity Chromatography

Affinity chromatography (AC) relies on the interaction of the protein with an immobilized ligand. AC is predicated, in part, on the interaction of ligands attached to chromatographic supports. A hydrophobic ligand coupled to a matrix is variously referred to herein as an AC support, AC gel or AC column. It is further appreciated that the strength of the interaction between the protein and the AC support is not only a function of the proportion of non-polar to polar surfaces on the protein but by the distribution of the non-polar surfaces as well.

A number of matrices may be employed in the preparation of AC columns. Preferably, such matrices are beads, and more preferably spherical beads, which serve as a support surface for the complexing agent of the invention. Suggested materials for the matrices include agarose, cross-linked dextran, polyhydroxyl ethyl methacrylate, polyacrylamide, cellulose, and derivatives or combinations thereof, preferably in the form of porous spheres. Cellulose acetate has previously been successfully used in devices for purification of biological fluids, e.g., extracorporeal blood purification devices. Polyurethane is particularly blood compatible. Silica and its derivatives are also especially useful as support material for use with heteropoly acids. See U.S. Pat. Nos. 5,475,178 and 5,366,945.

The preferred material for use in the methods of the present invention is agarose, a naturally occurring hydrophilic polymer. A beaded gel with a porosity of from 90–96% is formed by varying the percentage of agarose. The molecular weight of the gel ranges from 0.5 million for 10% agarose to 20 million for 4% agarose. Particle diameters ranging from 20 to 200 microns are commercially available. The mechanical strength of agarose beads can be increased by either increasing the percentage of agarose or crosslinking the beads with epichlorohydrin or 2,3 dibromopropanol, using the method of J. Porath et al., *J. Chromat.* 60:167 (1971). This allows a corresponding increase in the maximum operating pressure (a fifty percent increase in agarose leads to a two to four fold increase in the maximum operating pressure).

The criteria to determine the appropriate coupling method are: minimization of leakage of the complexing agent from the support, maintenance of the thermal stability of the compound, and retention of the optimum amount of complexing agent. The technique must also not cause deterioration in the support material or the production of reactive groups on the support that would bind blood components in vivo. The complexing agent must also retain its activity over time.

Further factors which must be considered in optimizing the affinity chromatography coupling method are: the extent of distribution of the coupling agent within the particles and/or columns; pH; temperature; the flow speed of the biological sample through the column; the size of the bound complexing agent; and/or the diameter and pore size of the particular support. Each of these conditions can be optimized for a particular procedure, biological sample, and complexing agent as will be apparent to one skilled in the art.

The AC composition of the present invention can be contained within a filtration cartridge for easy use of the composition in a biological fluid purification process. When the column composition is contained within a single cartridge, it can easily and conveniently be replaced when the purifying capacity of the composition becomes exhausted. Alternatively, the cartridge may be an integral part of a purifying device, in which case the entire device is replaced once the filtration composition has exhausted its efficacy. The support particles with the complexing agent are placed within the cartridge, and the solution to be reacted with the complexing agent is then circulated through the cartridge. Commercially available units for dialysis, blood exchange or oxygenation can be adapted for use as the purifying device.

Filtration Methods

Another method that may be used to remove prions from a biological sample involves filtration through a membrane. The membrane may have the prion complexing agent conjugated directly to the membrane, either on the side facing the biological fluid or more preferably on the side away from the biological fluid. Alternatively, the complexing agent may be compartmentalized in an area behind the membrane, which is inaccessible to the larger components of the biological materials, e.g., blood cells. In the latter example, the complexing agent can be bound to an insoluble matrix behind the membrane. The membrane for use in the present invention may be in planar form, in the form of one or more hollow fibers, and/or in the form of flat foils. See U.S. Pat. No. 4,361,484.

Suitable materials for the membrane include regenerated cellulose, cellulose acetate, non-woven acrylic copolymer, polysulphone, polyether sulphone, polyacrylonitrile, polyamide and the like. The biologically active material is immobilized in the pores and/or on the surface of the side of the membrane that faces away from the biological fluid. Thereby the components, such as blood corpuscles, are prevented from contacting the active material. The pores of the membrane are usually of the magnitude of order of 0.01 to 0.8 microns, preferably 0.15 to 0.45 microns. The polymer support must be stable under the conditions of its planned use, i.e., it should not be chemically or enzymatically degraded by blood. The support and immobilized complexing agent must be blood compatible, and the support should have good flow characteristics and low compressibility under clinical flow rates in the range of 150–250 ml/min.

Through the above construction of the microporous membrane, i.e., asymmetric immobilizing of the prion complexing agent, the biological fluid need not be exposed to any following filtering for removing possible remaining harmful residues. The separation as the removal of the substances can thereby be performed in one and the same step.

The microporous semipermeable membrane can be in the form of individual fibers, which are bundled and encapsulated within one and the same casing, with an inlet and outlet for the biological fluid. The ends of the fibers are glued by means of a suitable binder to retain the individual fibers essentially parallel within the casing. One end of the fibers or bundles of fibers is provided in communication with the inlet, while the opposite end is provided in communication with the outlet.

The biological material is pumped into the casing through the inlet and through the longitudinal void of the fibers and out of the casing through the outlet. During the passage through the casing the fluid is exposed to the pressure variations, such that only a penetrating fraction is caused to flow in an alternating path through the fiber walls in each direction for contacting with the prion complexing material. The means for the realization of the pressure variations may again be made up of an expansion chamber in communication with the space between the individual fibers and bundles of fibers, respectively. Any subsequent filtering of the biological material for the removal of possible harmful residues is not needed, since the filtering is automatically achieved through the passage of the fluid through the fiber walls.

The pressure variations may vary from −200 to +200 mmHg, preferably from −100 to +100 mmHg. The longer the diffusion distance for the blood, for example if the prion complexing agent is bound to an unsoluble matrix behind the membrane, the higher compensating pressure variations are required to achieve the desired separation effect. In a corresponding way the frequency of the pressure variations may vary from about 0.05 up to about 10 Hz, preferably 0.5 to 1 Hz. After the passage through the treating unit the biological material, e.g., whole blood, may reinserted in the patient directly, or may be stored for future use. Treated blood may be stored whole, or may be stored in its various components, e.g., plasma, platelets, erythrocytes, etc. Alternatively, the blood may be separated into its components prior to removal of prions.

When the complexing agent is an antibody, it is often desirable to have a molecular spacer segment forming means for spacing the antibody from the wall of the exterior porous side of the hollow fiber membrane. This general arrangement is preferred when the molecular weight of the antigen is large, e.g., 100,000 Daltons or higher in molecular weight. For example, a six or eight carbon methylene group is convenient as a spacer or "handle" between antibody and membrane surface. When an antigen is readily absorbed by albumin or more readily chemically reacted with albumin than with the material of the filter membrane surface, the spacer molecule may be a protein such a albumin. The outer surface of a membrane can be considered a relatively porous material compared to that of the interior surface, which is normally the effective filter surface of an ultrafilter membrane of the asymmetric, sometimes called anisotropic, type. Thus, for example, the exterior, porous side of a membrane may be treated with a 17% human albumin solution in saline. The albumin will coat the surfaces within the porous zone of the membrane structure (i.e., the zone that underlies the barrier layer of the membrane) and, thereafter, a solution of protein (e.g., a $PrP^{Sc}$ antibody) can be deposited upon the albumin. Often it is desirable to cross-link the protein somewhat (as with a dilute glutaraldehyde solution or some other such mild cross-link-inducing agent); this aids in anchoring the material in place on the membrane surface.

One approach to preparing a cartridge that is capable of removing pathogenic factors from blood is an extracorporeal circulation system with fiber membranes having sufficient permeability for the pathogenic blood factor to be removed through the membrane and into a soluble, immobilized antibody sequestered in the extrafiber space. This involves the formation of a high molecular weight polymeric conjugate of the $PrP^{Sc}$ antibody and $PrP^{Sc}$ that cannot cross the filtration side of the membrane into the remainder of the biological sample, i.e., where the cells are maintained.

In order to form a soluble, immobilized complexing agent, the molecular weight of the immunoreactive complexing agent may be increased to such a size that it will not diffuse, from the exterior, porous portion of the fiber and into the blood to be purified. This can be done by chemically reacting the complexing agent with a high molecular weight, water-soluble substance such as silica gel or dextran or by polymerizing the immunoreactive complexing agent. The use of such macromolecular-borne antibodies is advantageous for high rate of antigen absorption, due to enhanced rate of polarization effects on mass transfer and binding kinetics.

Alternatively, the membrane may be composed of two membrane halves, which are mechanically generally identical to each other but which chemically may be built up of different material. In this case, it is enough if only the membrane half that faces away from the biological material is able to bind to the prion complexing agent. For example, the membrane halves may be provided in an abutting relationship to each other, wherein the $PrP^{Sc}$ complexing agent preferably is bound in the pores and on both surfaces of the membrane half that faces away from the biological material.

The complexing agent (e.g., NaPTA or anti-$PrP^{Sc}$ antibodies) can also be immobilized in the membrane so that the surface that faces towards the biological material is free of the contacting reagent. This is to avoid contact between blood corpuscles and the reagent and thereby pyrogen and/or anaphylactic reactions. Thus it is a form of a symmetric immobilization, where on one surface of the membrane (as well as in the pores) the prion complexing agent is immobilized. The advantage of immobilizing within the pores of the membrane is that the active microscopic surface may be manifolded (>1000) compared to the macroscopic surface. Since the complexing agent is immobilized in the part of membrane that faces away from the biological material the biological material will not come into contact with the material. Consequently, any separate filtering of the biological material is not necessary.

Alternatively, the prion complexing agent may be bound to an insoluble matrix behind the membrane. The treating process is yet similar, but since the necessary diffusion distance is about 10 times longer, it may be necessary to arrange a somewhat more real flow through the membrane.

Irrespective of whether the prion complexing agent is immobilized in the pores or immobilized to an insoluble matrix behind the membrane, the immobilizing procedure is preferably performed such that the complex of prions and the complexing agent remains bound and immobilized, i.e., it is not present in the blood following the purification technique. Generally, covalent coupling is the safest immobilization. The nature of covalent coupling used depends on the choice of membrane material and the nature of the complexing agent.

Magnetic Particles

Prions can also be removed from biological materials using magnetic particles comprised of prion complexing agent. The principle components of the magnetic particles of the present invention are a magnetic core. The core consists of particles of iron oxide or other magnetic materials. The PrPSc binding agent of the invention can be incorporated directly on the magnetic core, or indirectly incorporated onto the magnetic core, e.g., through the use of a fibrous material and a binding agent. The fibrous material may comprise an organic polymer in the form of fibers, such as carbohydrate polymers, urea formaldehyde or polynonamethylene urea, and, in particular, cellulose fibers. The binding agent is a material which is introduced between the magnetic core and the fiber strands as a liquid, or in solution, and is solidified during the production process of freezing, polymerization or evaporation of a solvent. Examples of suitable binding agents are agar, gelatin, epoxy resin or urea formaldehyde furfuryl alcohol.

Magnetic microparticles useful in the present method can be a variety of shapes, which can be regular or irregular; preferably the shape maximizes the surface areas of the microparticles. The magnetic microparticles should be of such a size that its separation from solution, for example by filtration or magnetic separation, is not difficult. In addition, the magnetic microparticles should not be so large that surface area is minimized or that they are not suitable for microscale operations. Suitable sizes range from about 0.1 .mu. mean diameter to about 100 .mu. mean diameter. A preferred size is about 1.0 .mu. mean diameter. Suitable magnetic microparticles are commercially available from PerSeptive Diagnostics and are referred to as BioMag COOH (Catalog Number 8-4125).

The coated magnetic particles of the present invention can be produced by stirring or mixing the core particles in a suspension comprising a fibrous material, a prion complexing agent, and a binding agent. The fibers attach to the core particles and the binding agent fills the interstices. The binding agent is then solidified by one of the means as discussed above, in such a manner that the prion complexing agent is accessible on the outer surface. An example of such a system, which uses iron oxide as the core particles, cellulose fibers as the fibrous material and agar as the binding agent is described in U.S. Pat. No. 5,705,628.

The present invention also includes within its scope a composite magnetic resin that comprises magnetic particles embedded in a organic polymer matrix, which either contains, or has attached thereto, sites which are selective for prions.

The composite may thus comprise magnetic particles embedded in a polymeric resin which contains active sites or chemicals intended to selectively absorb to prions. For example, the polymeric resin has small particles of selective absorbers bound thereto. The selective absorbers may be, for example, a metal salt of phosphotungtic acid.

The composite magnetic particles of the present invention may be used in a method for the removal of prions from any flowable biological sample. Removal of prions from the human product is by contacting the solution to be treated with particles of a composite magnetic resin with immobilized complexing agent and separating by magnetic filtration the composite magnetic resin particles from the solution. These magnetic particles may be used once and discarded, or recycled for use in purifying other blood products. Particles can be recycled by subjecting the separated composite magnetic resin particles to regeneration using an appropriate regenerant solution, separating the regenerated composite magnetic resin particles from the regenerant solution.

The composite magnetic resin particles with bound prions are then selectively removed from the solution by magnetic filtration using techniques known in the art. The composite magnetic resin particles are then recovered from the filter and the prions removed therefrom using an appropriate regenerant solution, for example an acidic solution. The cleaned composite magnetic resin particles can then be recovered from the regenerant solution by magnetic filtration and the clean particles recycled for additional use.

Purification of biological material from a patient may be through an extracorporal treatment unit, and following treatment the purified fluid may either be stored or may be reintroduced to the patient. The biological material is pumped from, for example, a patient into a treating unit comprising a microporous semi-permeable membrane having pores of 0.01–0.8 microns, preferably 0.15–0.45 microns. During the passage through the treating unit the biological material is exposed to pressure variations (for example from −200 to +200 mmHg, preferably from −100 to +100 mmHg), whereby a penetrating fraction of the biological material, e.g., the plasma, is caused to flow in an alternating path through the membrane wall in each direction for contacting the complexing agent.

Organs and Tissues for Transplantation

Organ, tissue and corneal transplantation are routine surgeries in the United States. As with the blood supply, demand is far ahead of supply. More than 57,000 people are waiting for organ transplants. Many people who need transplants cannot get them because of the shortages; and some of them will die while waiting for a heart, liver or kidney. An estimated 15,000 brain deaths occur in the United States each year, but only about 30 percent donate their organs. It is possible to transplant 25 different kinds of organs and tissues, including corneas, heart, heart valves, liver, kidneys, bone and cartilage, bone marrow, skin, pancreas, lungs, intestine, etc. In 1996, 4,058 livers were transplanted in the United States, compared with 164 in 1983. At least 9,000 Americans, however, are still waiting for liver transplants. There were 44,000 corneal transplants performed in the United States last year. The number of Americans on waiting lists for corneas averages 5,000 at any given time. There were 6,500 skin grafts performed in 1996–1997. Transplanted skin is used an estimated 100,000 times per year as replacement tissue for severe burns. Another 500,000 patients could have their wound-healing time shortened if enough skin were available. 700,000 bone grafts were done in 1996. Transplanted bone tissue can replace bone destroyed by tumors, trauma, and infection, healing limbs that would otherwise have been amputated. Due to advances in medical technology and improved preservation techniques, vital organs may be transported thousands of miles to a recipient. At the present time, an organ donor in Great Britain introduces a potential risk of transmitting CJD to a transplant recipient.

Use of the present invention to treat organs and tissues prior to transplantation would increase the available pool of potential donated organs and tissues available for those in need, and would also denature prions in any existing organs prior to transplantation.

A further aspect of the invention is to treat collagen before it is injected into a patient. Injectable collagen is a naturally produced protein, derived from purified bovine collagen. It is used most frequently in cosmetic surgery, to minimize the appearance of wrinkles and scars, and to enlarge the lips. Injectable collagen is also used to treat stress incontinence in women by injecting it on either side of the urethra. For all of these procedures, the collagen is injected with a fine-gauge needle under the skin where it is incorporated into the body's own network of collagen fibers. The injections have to be repeated every 3–6 months to maintain the effect. Use of the claimed compositions and methods to treat the collagen before it is injected into a patient would remove any possibility of transferring prions from an infected cow to a human.

The instant invention is not limited to human tissues and organs for transplantation. Xenografts are also encompassed by the current invention. Suitable organs for transplant into humans may be found in baboons, chimpanzees, pigs, sheep, etc. Although xenografts are still experimental, pig heart valves have been used for years as replacements for human heart valves. Clinical studies are ongoing with pig neural cells being transplanted into Parkinson's disease patients. The continuing progress in this area shows that the present invention may be suitable for application to animal tissues and organs before transplant into a human recipient.

In summary, the invention comprises a composition that inhibits prion formation or denatures existing prions in blood, blood products, organs and tissues. Blood, blood products, tissue or organs may be pre-treated to remove prions to the extent possible. Thereafter, a composition of the invention is added to render any remaining prions non-infectious. The active component is added in an amount sufficient to denature any prions present in the blood, blood product, tissue or organ to be transplanted. The amount will vary based on factors such as the type of organ/tissue and its size. Generally, the organ or tissue will be treated in a low pH (less than 5.0) solution, where the active ingredient is present in an amount about 0.1 to 1.0 µg per ml or mg of material to be treated. The treatment is for 2 hours or less, at a temperature of between 4° C. and 37° C.

ScN2a Cell-Based Assay

Another aspect of the invention is to assay compounds to determine whether the compounds have the ability to denature infectious proteins. On reading this disclosure, and in particular the description provided herein for particular assays, other assays will be apparent to those skilled in the art. The basic concept is: (1) providing an acid component in an aqueous and/or alcohol carrier, (2) adding the component (not known to be active), and (3) contacting the test composition with a sample known to contain an infectious protein. After allowing time to pass (e.g., 5 minutes to 2 hours) procedures described here are used to (4) determine if the component is "active" i.e., renders the protein non-infectious. Multiple compounds can be added to the composition and tested simultaneously. If no effect is found, then all of the compounds are not active. If a sterilizing effect is found, the group of compounds tested can be divided in two and retested until an active compound is specifically identified. Dividing the originally tested group in any manner and retesting can be carried out any number of times.

The active component can be checked against one prion strain at a time or against multiple strains simultaneously. Some active components such as SDS will inactivate all known strains of prion, while some polycationic dendrimers will inactivate only specific strains. When the active component inactivates all strains it is useful as an antiseptic and/or therapeutic. When it inactivates only a specific strain it can be used to determine the strain of infectious prion in a sample.

Efforts were made to optimize the transfection of ScN2a cells with pSPOX expression plasmids (Scott, M. R. et al., *Protein Sci.* 1:986–997 (1992)). In connection with those effects, an evaluation was made of a transfection protocol that used SuperFect™ reagent (QIAGEN®). It was found that epitope-tagged (MHM2) PrP$^{Sc}$ (Scott, M. R. et al., *Protein Sci.* 1:986–997 (1992)) could not be detected in ScN2a cells following SuperFect-mediated transfection, whereas MHM2 PrP$^{Sc}$ was efficiently formed when a cationic liposome method for DNA delivery was used. Close scrutiny revealed that, prior to protease digestion, SuperFect-transfected samples expressed MHM2 bands, which are not seen in the background pattern of an untransfected sample. The 3F4 monoclonal antibody does not react with MoPrP but does exhibit high background staining on Western blots of mouse ScN2a cells. Increased immunostaining in the 20–30 kDa region was observed compared to the non-transfected sample. These observations led us to conclude that MHM2 PrP was successfully expressed using SuperFect™ transfection reagent, but that conversion of MHM2 PrP$^C$ to protease-resistant MHM2 PrP$^{Sc}$ was inhibited by SuperFect™.

To investigate this apparent inhibition, a Western blot was reprobed with RO73 polyclonal antiserum to detect endogenous MoPrP$^{Sc}$, the presence of which is diagnostic for prion infection in ScN2a cells (Butler, D. A. et al., *J. Virol.* 62:1558–1564 (1988)). Surprisingly, it was found that the SuperFect-treated ScN2a cells no longer contained detectable quantities of MoPrP$^{Sc}$. This result was also confirmed in Western blots. To investigate the mechanism by which SuperFect™ reduced the level of pre-existing PrP$^{Sc}$ in chronically infected ScN2a cells, measurements were made of endogenous PrP$^{Sc}$ in ScN2a cells exposed to various concentrations of SuperFect™ in the absence of plasmid DNA. The results showed that treatment with SuperFect™ (a branched polycation) caused the disappearance of PrP$^{Sc}$ from ScN2a cells in a dose-dependent manner. The concentration of SuperFect™ required to eliminate >95% of pre-existing PrP$^{Sc}$ with a three hour exposure was found to be about 150 µg/ml. Duration of treatment also influenced the ability of SuperFect™ to remove PrP$^{Sc}$ from ScN2a cells: exposure to 150 µg/ml SuperFect™ for 10 min did not affect PrP$^{Sc}$ levels, whereas 7.5 µg/ml SuperFect™ eliminated all detectable PrP$^{Sc}$ with a t1/2=8 h.

SuperFect™ is a mixture of branched polyamines derived from heat-induced degradation of a PAMAM dendrimer (Tang, M. X. et al., *Bioconjug. Chem.* 7:703–714 (1996)). Knowing this structure the ability of several other branched and unbranched polymers to eliminate PrP$^{Sc}$ from ScN2a cells were tested (see Table 2, below). The branched polymers investigated include various preparations of PEI, as well as intact PAMAM and PPI dendrimers. Dendrimers are manufactured by a repetitive divergent growth technique, allowing the synthesis of successive, well-defined "generations" of homodisperse structures (FIG. 1). The potency of both PAMAM and PPI dendrimers in eliminating PrP$^{Sc}$ from ScN2a cells increased as the generation level increased. The most potent compounds with respect to eliminating PrP$^{Sc}$ were PAMAM generation 4.0 and PPI generation 4.0, whereas PAMAM generation 1.0 showed very little ability to eliminate PrP$^{Sc}$ (see Table 2). Similarly, a high MW fraction of PEI was more potent than low MW PEI.

From the foregoing data, it is clear that for all three branched polyamines tested, increasing molecular size corresponded to an increased potency for eliminating PrP$^{Sc}$. To determine whether this trend was directly attributable to increased surface density of amino groups on the larger molecules, PAMAM-OH generation 4.0 was tested. This is a dendrimer that resembles PAMAM generation 4.0 except that hydroxyls replace amino groups on its surface. Unlike PAMAM generation 4.0, PAMAM-OH generation 4.0 did not cause a reduction of PrP$^{Sc}$ levels even at the highest concentration tested (10 mg/ml), establishing that the amino groups are required for the elimination of PrP$^{Sc}$ by PAMAM (Table 2).

In an effort to assess the contribution of the branched architecture to the clearing ability of polyamines for PrP$^{Sc}$, the linear molecules poly-(L)lysine and linear PEI were also tested. Both of these linear compounds were less potent than a preparation of branched PEI with similar average molecular weight (Table 2), establishing that a branched molecular architecture optimizes the ability of polyamines to eliminate PrP$^{Sc}$, presumably because the branched structures achieve a higher density of surface amino groups.

Kinetics of PrP$^{Sc}$ Elimination by Polyamines

The preceding results demonstrate the potent ability of branched polyamines to clear PrP$^{Sc}$ from ScN2a cells within a few hours of treatment. The utility of these compounds to act as therapeutics for treatment of prion disease was tested by determining whether they were cytotoxic for ScN2a cells, using as criteria cell growth, morphology, and viability as measured by trypan blue staining. None of the compounds was cytotoxic to ScN2a cells after exposure for one week at concentrations up to 7.5 μg/ml. To determine whether branched polyamines can cure ScN2a cells of scrapie infection without affecting cell viability, the kinetics of prion clearance was examined in the presence of a non-cytotoxic concentration (7.5 μg/ml) of three different branched polyamines. ScN2a cells were exposed to SuperFect™, PEI, or PAMAM generation 4.0 for varying periods of time. The kinetics of PrP$^{Sc}$ elimination was assessed by Western blotting. All three compounds caused a substantial reduction in PrP$^{Sc}$ levels after 8–16 h of treatment, and of the three compounds, PEI appeared to remove PrP$^{Sc}$ most quickly, with a t1/2=4 h.

Curing Neuroblastoma Cells of Scrapie Infection

The above results show that it is possible to reverse the accumulation of PrP$^{Sc}$ in ScN2a cells under non-cytotoxic conditions. It was also found that extended exposure to even lower levels of the branched polyamines (1.5 μg/ml) was sufficient to eliminate PrP$^{Sc}$. Based on these findings, this protocol was used to determine whether the severe reduction in PrP$^{Sc}$ levels following exposure to branched polyamines would persist after removal of the compounds. Following the exposure of ScN2a cells to a 1.5 μg/ml SuperFect™ for 1 week, PrP$^{Sc}$ was reduced to <1% of the baseline level, but then increased back to ~5% of the baseline level after 3 additional weeks in culture in the absence of polyamine. In contrast, following exposure to 1.5 μg/ml of either PEI or PAMAM generation 4.0 for 1 week, PrP$^{Sc}$ was completely eliminated and did not return even after 3 weeks in culture without polyamines. A more intensive course of treatment with 1.8 μg/ml SuperFect™ for 9 d also cured ScN2a cells of scrapie infection fully, manifested by the absence of PrP$^{Sc}$ 1 month after removal of SuperFect™.

Evidence for Polyamines Acting within An Acidic Compartment

The above results showed the potent activity of branched polyamines in rapidly clearing scrapie prions from cultured ScN2a cells. Based on these results, the mechanism by which these compounds act was investigated. All of the compounds which effect removal of PrP$^{Sc}$ from ScN2a cells are known to traffic through endosomes (Boussif, O. et al., *Proc. Natl. Acad. Sci. USA* 92:7297–7301 (1995); and Haensler, J. & Szoka, F. C. J., *Bioconjug. Chem.* 4:372–379 (1993)). Since PrP$^{C}$ is converted into PrP$^{Sc}$ in caveolae-like domains (CLDs) or rafts (Gorodinsky, A. & Harris, D. A., *J. Cell Biol.* 129:619–627 (1995); Taraboulos, A. et al., *J. Cell Biol.* 129:121–132 (1995); Vey, M. et al., *Proc. Natl. Acad. Sci. USA* 93:14945–14949 (1996); and Kaneko, K. et al., *Proc. Natl. Acad. Sci. USA* 94:2333–2338 (1997)) and is then internalized through the endocytic pathway (Caughey, B. et al., *J. Virol.* 65:6597–6603 (1991); and Borchelt, D. R. et al., *J. Biol. Chem.* 267:16188–16199 (1992)), it was deduced that polyamines act upon PrP$^{Sc}$ in endosomes or lysosomes. This deduction was investigated by determining the effect of pretreatment with the lysosomotropic agents chloroquine and NH$_4$Cl on the ability of polyamines to eliminate PrP$^{Sc}$. These lysosomotropic agents alkalinize endosomes and have no effect on PrP$^{Sc}$ levels when administered to ScN2a cells (Taraboulos, A. et al., *Mol. Biol. Cell* 3:851–863 (1992)). Experimental results obtained show that 100 μM chloroquine, but not 30 μM NH$_4$Cl, blocked the ability of PEI to eliminate PrP$^{Sc}$. Similar results were obtained with SuperFect™ and PAMAM, generation 4.0. Although the failure of NH$_4$Cl to affect PrP$^{Sc}$ levels is not easily explained, the ability of chloroquine to attenuate the ability of branched polyamines to remove PrP$^{Sc}$ is consistent with the notion that these agents act in endosomes or lysosomes.

Organ Homogenate Assay

The above results with cell cultures prompted investigating the possibility that in an acidic environment branched polyamines, either by indirectly interacting with PrP$^{Sc}$ or with another cellular component, could cause PrP$^{Sc}$ to become susceptible to hydrolases present in the endosome/lysozome. An in vitro degradation assay was developed to evaluate the effect of pH on the ability of polyamines to render PrP$^{Sc}$ sensitive to protease. Crude homogenates of scrapie-infected mouse brain were exposed to a broad range of pH values in the presence or absence of SuperFect™ and then treated with proteinase K prior to Western blotting. Whereas PrP$^{Sc}$ remained resistant to protease hydrolysis throughout the pH range (3.6–9.6) in the absence of SuperFect™, addition of the branched polyamine at pH 4.0 or below caused PrP$^{Sc}$ to become almost completely degraded by protease.

Polyamine addition showed a dramatic effect on clearance in vitro which was optimized at pH 4 or less. These results show that polyamines act on PrP$^{Sc}$ in an acidic compartment. To establish that the in vitro degradation assay is a valid approximation of the mechanism by which branched polyamines enhance the clearance of PrP$^{Sc}$ from cultured cells, a structure activity analysis was performed with several of the compounds tested in culture cells. An excellent correlation was found between the clearance of PrP$^{Sc}$ in cultured ScN2a cells (Table 2) and the ability to render PrP$^{Sc}$ susceptible to protease at acidic pH in vitro. Notably, PAMAM-OH generation 4.0 failed to render PrP$^{Sc}$ susceptible to protease, whereas PAMAM generation 4.0 and PPI, generation 4.0 exhibited an even stronger activity than SuperFect™ in vitro, as expected from their observed potency in cultured ScN2a cells (Table 2).

Mechanism of Action

When a pH of 4.0 or less was maintained the results show that certain branched polyamines cause the rapid elimination of PrP$^{Sc}$ from ScN2a cells in a dose- and time-dependent manner. These compounds demonstrate a potent ability to remove prions from cultured cells at concentrations that are completely non-cytotoxic. The cells may be maintained indefinitely in culture in the presence of therapeutic levels of branched polyamines. Furthermore, when ScN2a cells were exposed to these compounds for ~1 week, PrP$^{Sc}$ was reduced to undetectable levels and remained so for at least one month after removal of the polyamine.

Clarification of the exact mechanism of PrP$^{Sc}$ elimination by branched polyamines is an important objective. Although a number of possible scenarios exist, several possibilities may be excluded already. One possibility that was eliminated was that polyamines act by induction of chaperones such as heat shock proteins that mediate prion protein refolding because the above results show that it was possible to reproduce the phenomenon in vitro. Furthermore, polyamines seem to offer advantages over other putative therapeutics that would seek to promote refolding: at very high concentrations, dimethyl sulfoxide (DMSO) and glycerol act as direct "chemical chaperones" and inhibit the formation of new PrP$^{Sc}$ (Tatzelt, J. et al., *EMBO J.* 15:6363–6373 (1996)), but these compounds cannot reduce pre-existing PrP$^{Sc}$ levels. Furthermore, polyamines inhibit PrP$^{Sc}$ formation at much lower concentrations than these agents. The ability of polyamines to effect the rapid clearance of PrP$^{Sc}$ also contrasts with the activity of other potential prion therapeutics. Sulfated polyanions may inhibit PrP$^{Sc}$ accumulation in ScN2a cells by directly binding to PrP$^{C}$ (Gabizon, R. et al., *J. Cell. Physiol.* 157 (1993); Caughey, B. et al., *J. Virol.* 68:2135–2141 (1994)), but because branched polyamines are able to clear pre-existing PrP$^{Sc}$, their mechanism of action cannot simply involve binding to PrP$^{C}$ and inhibiting de novo synthesis.

Another possible mechanism which can be excluded is endosomal rupture. The branched polyamines which were effective in clearing PrP$^{Sc}$ from ScN2a cells in our experiments, PEI, SuperFect™ and PAMAM, are also potent lysosomotropic, osmotic agents which can swell in acidic environments and rupture endosomes (Boussif, O. et al., *Proc. Natl. Acad. Sci. USA* 92:7297–7301 (1995); Haensler, J. & Szoka, F. C. J., *Bioconjug. Chem.* 4:372–379 (1993)). This might suggest that branched polyamines clear PrP$^{Sc}$ from ScN2a cells by rupturing endosomes and exposing PrP$^{Sc}$ to cytosolic degradation processes. However, it is known that the lysosomotropic, endosome-rupturing agents NH$_4$Cl, chloroquine, and monensin do not interfere with the formation of PrP$^{Sc}$ in ScN2a cells (Taraboulos, A. et al., *Mol. Biol. Cell* 3:851–863 (1992)). Furthermore, the results also show that chloroquine interferes with the ability of branched polyamines to clear PrP$^{Sc}$ and that polyamines can clear PrP$^{Sc}$ in vitro at acidic pH in the absence of cell membranes. Together, these observations rule out endosome rupture as the mechanism by which branched polyamines remove PrP$^{Sc}$.

Without committing to any particular mechanism of action it appears likely that branched polyamines require the acidic environment of intact endosomes or lyzosomes to destroy PrP$^{Sc}$. The structure-activity profile of polymers tested reveals that the most active compounds possess densely packed, regularly-spaced amino groups, suggesting that these compounds may bind to a ligand which has periodically-spaced negative charges. Several scenarios remain possible: (1) Branched polyamines may bind directly to PrP$^{Sc}$ arranged as an amyloid with exposed negatively-charged moieties and induce a conformational change under acidic conditions; (2) Treatment of PrP 27–30 with acid decreases turbidity and increases α-helical content, suggesting that such conditions might dissociate PrP$^{Sc}$ into monomers (Safar, J., Roller, P. P., Gajdusek, D. C. & Gibbs, C. J., Jr. Scrapie amyloid (prion) protein has the conformational characteristics of an aggregated molten globule folding intermediate). It is therefore possible that polyamines bind to an equilibrium unfolding intermediate of PrP$^{Sc}$ present under acidic conditions. (3) Alternatively, polyamines might sequester a cryptic, negatively charged component bound to PrP$^{Sc}$ that is essential for protease resistance, but which is only released when PrP$^{Sc}$ undergoes an acid-induced conformational change. Such a component might act as a chaperone for PrP$^{Sc}$ inside endosomes or lysosomes. (4) Finally, another possibility is that polyamines activate an endosomal or lysosomal factor which can induce a conformational change in PrPS$^{Sc}$. Clearly, more work will be required to determine the precise mechanism by which branched polyamines destroy PrP$^{Sc}$.

General Applicability of Assay

The in vitro assay described here is generally applicable in the search for compounds that effectively clear conformationally altered proteins present in food thereby preventing a number of degenerative diseases, where the accumulation of proteins seems to mediate the pathogenesis of these illnesses. By simulating lysosomes, where proteases hydrolyze proteins under acidic conditions, the in vitro brain homogenate assay is able to rapidly evaluate the efficacy of a variety of polyamines to induce degradation of PrP$^{Sc}$.

The in vitro assay which used scrapie infected brain homogenate to test for compounds which clear PrP$^{Sc}$ could be modified to assay for compounds which would clear any conformationally altered protein. The assay is carried out by homogenizing the organ or tissue where the conformationally altered protein is present in the highest concentration. The pH of the homogenate is then reduced to less than 5.0 and preferably 4.0 or less. For example, pancreatic tissue can be homogenized to produce an assay to test for compounds that clear amylin, which is associated with type II Diabetes. Homogenized kidney could be used to test for compounds which clear β$_2$-microglobulin and homogenized heart or vascular tissue used to test for compounds which clear atrial natriuretic factor. Those skilled in the art will recognize other organs and tissue types that can be homogenized to test for other compounds that clear other conformationally altered proteins.

Besides using the in vitro assay to screen for potential drugs, the compounds found via the assay such as branched polyamines provide a new tool for exploring the conversion of a protein to conformationally altered protein, e.g., PrP$^{C}$ into PrP$^{Sc}$. The mechanism by which branched polyamines render PrP$^{Sc}$ susceptible to proteolysis, remains to be established. Whether the interaction of branched polyamines with PrP$^{Sc}$ is reversible is unknown. In addition, it is not known whether branched polyamines are able to solubilize PrP$^{Sc}$ without irreversibly denaturing the protein. Whatever the mechanism by which branched polyamines interact with PrP$^{Sc}$, it is likely to be different from that found with chaotropes as well as denaturing detergents and solvents (Prusiner, S. B. et al., *Proc. Natl. Acad. Sci. USA* 90:2793–2797 (1993)).

Using the assays described and disclosed here certain specific branched polyamines have been found which mediate the clearance of PrP$^{Sc}$ from cultured cells under non-cytotoxic conditions. These compounds offer the possibility of being added to a wide range of low pH food products to neutralize conformational altered proteins present. Since the compounds act by stimulating normal cellular pathways of protein degradation to destroy PrP$^{Sc}$, this class of compounds would also likely be of value in the treatment of other degenerative and hereditary disorders where abnormally folded, wild-type or mutant proteins accumulate. Such an approach may find merit in developing an effective therapeutics for one or more of the common, degenerative illnesses including Alzheimer's disease, Parkinson's disease, amyotrophic lateral sclerosis, frontotemporal dementia, adult onset diabetes mellitus and the amyloidoses (Beyreuther, K. & Masters, C. L., *Nature Medicine* 3:723–725 (1997); Masters, C. L. & Beyreuther, K., *BMJ* 316:446–448 (1998); Selkoe, D. J., *Trends in Cell Biol.* 8:447–453 (1998); Selkoe, D. J., *Nature* 399:A23–31 (1999); Wong, P. C. et al., *Neuron* 14:1105–1116 (1995); Spillantini, M. G. et al., *Proc. Natl. Acad. Sci. USA* 95:6469–6473 (1998); Hutton, M., et al., *Nature* 393:702–705 (1998); and Stone, M. J., *Blood* 75:531–545 (1990)). Whether branched polyamines might also prove efficacious in a variety of inherited disorders where the accumulation of abnormal proteins is a hallmark of the illness remains to be established; these genetic maladies include heritable forms of prion disease, Alzheimer's disease, Parkinson's disease, amyotrophic lateral sclerosis, frontotemporal dementia, Pick's disease and amyloidosis, as well as the triplet repeat diseases including Huntington's disease, spinal cerebellar ataxias and myotonic dystrophy (Fu, Y. -H. et al., Science 255:1256–1259 (1992); and Group, T., Cell 72:971–983 (1993)). Compounds identified via assays of the invention such as branched polyamines will find utility in preventing or delaying the onset of these genetic diseases where carriers can often be identified decades in advance of detectable neurologic or systemic dysfunction.

The invention is based on the discovery that several dendritic polycations, including the starburst dendrimers SuperFect™ (QIAGEN®, Valencia, Calif.), polyamidoamide (PAMAM), and the hyperbranched polycation polyethyleneimine (PEI), were surprisingly found to eliminate $PrP^{Sc}$ from cultured scrapie-infected neuroblastoma cells. These highly-branched, polycationic compounds provide a novel class of therapeutic agents to combat prion diseases and other degenerative disease including the amyloidoses. The removal of $PrP^{Sc}$ is dependent on both the concentration of dendritic polymer and length of exposure. Dendritic polymers were able to clear $PrP^{Sc}$ at concentrations which were not cytotoxic. Repeated exposures to heat-degraded starburst PAMAM dendrimer or PEI caused a dramatic reduction in $PrP^{Sc}$ levels, which persisted for a month even after removal of the compound. Dendritic polycations did not appear to destroy purified $PrP^{Sc}$ in vitro, and therefore may act through a generalized mechanism. Dendritic polycations represent a class of compounds which can be used as therapeutic agents in prion diseases and other disorders involving insoluble protein deposits, such as the amyloidoses.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

Chemicals. High molecular weight PEI was purchased from Fluka. DOTAP cationic lipid was purchased from Boehringer Mannheim and SuperFect™ transfection reagent was purchased from QIAGEN®. All other compounds were purchased from Sigmna-Aldrich. All test compounds were dissolved in water at stock concentration of 3 mg/ml and filtered through a Millipore 0.22 mm filter.

Cultured cells. Stock cultures of ScN2a cells were maintained in MEM with 10% FBS, 10% Glutamax (Gibco BRL), 100 U penicillin, and 100 mg/ml streptomycin (supplemented DME). Immediately prior to addition of test compounds, the dishes were washed twice with fresh supplemented DME media. After exposure to test compounds, dishes were drained of media and cells were harvested by lysis in 0.25–1 ml 20 mM Tris pH 8.0 containing 100 mM NaCl, 0.5% NP-40, and 0.5% sodium deoxycholate to obtain a total protein concentration of 1 mg/ml measured by the BCA assay. Nuclei were removed from the lysate by centrifugation at 2000 rpm for 5 min. For samples not treated with proteinase K, 40 µl of whole lysate (representing 40 µg total protein) was mixed with an equal volume of 2×SDS reducing sample buffer. For proteinase K digestion, 20 µg/ml proteinase K (Boehringer Mannheim) (total protein:enzyme ratio 50:1) was added, and the sample was incubated for 1 h at 37° C. Proteolytic digestion was terminated by the addition of Pefabloc to a final concentration of 5 mM. One ml samples were centrifuged at 100,000×g for 1 h at 4° C., the supernatants were discarded, and the pellets were resuspended in 80 µl of reducing SDS sample buffer for SDS-PAGE.

Brain homogenates. Brain homogenates from RML scrapie-affected CD-1 mice (10% (w/v) in sterile water) were prepared by repeated extrusion through syringe needles of successively smaller size, from 18 to 22 gauge. Nuclei and debris were removed by centrifugation at 1000×g for 5 min. The bicinchnoninic acid (BCA) protein assay (Pierce) was used to determine protein concentration. Homogenates were adjusted to 1 mg/ml protein in 1% NP-40. For reactions, 0.5 ml homogenate was incubated with 25 ml 1.0 M buffer (sodium acetate for pH 3–6 and Tris acetate for pH 7–10) plus or minus 10 ml of polyamine stock solution (3 mg/ml) for 2 h at 37° C. with constant shaking. The final pH value of each sample was measured directly with a calibrated pH electrode (Radiometer Copenhagen). Following incubation, each sample was neutralized with an equal volume 0.2 M HEPES pH 7.5 containing 0.3 M NaCl and 4% Sarkosyl. Proteinase K was added to achieve a final concentration of 20 µg/ml, and samples were incubated for 1 h at 37° C. Proteolytic digestion was terminated by the addition of Pefabloc to a final concentration of 5 µM. Ten µl of digested brain homogenate was mixed with equal volume 2×SDS sample buffer and analyzed by SDS-PAGE followed by Western blotting.

Western blotting. Following electrophoresis, Western blotting was performed as previously described (Scott, M. et al., Cell 59:847–857 (1989)). Samples were boiled for 5 min and cleared by centrifugation for 1 min at 14,000 rpm in aBeckman ultrafuge. SDS-PAGE was carried out in 1.5 mm, 12% polyacrylamide gels (Laemmli, U. K., Nature 227:680–685 (1970)). Membranes were blocked with 5% non-fat milk protein in PBST (calcium- and magnesium-free PBS plus 0.1% Tween 20) for 1 h at room temperature. Blocked membranes were incubated with primary RO73 polyclonal antibody (to detect MoPrP) (Serban, D. et al., Neurology 40:110–117 (1990)) or 3F4 monoclonal antibody (to detect MHM2 PrP) (Kascsak, R. J. et al., J. Virol. 61:3688–3693 (1987)) at 1:5000 dilution in PBST overnight at 4° C. Following incubation with primary antibody, membranes were washed 3×10 min in PBST, incubated with horseradish peroxidase-labeled secondary antibody (Amersham Life Sciences) diluted 1:5000 in PBST for 30 to 60 min at 4° C. and washed again for 3×10 min in PBST. After chemiluminescent development with ECL reagent (Amersham) for 1 min, blots were sealed in plastic covers and exposed to ECL Hypermax film (Amersham). Films were processed automatically in a Konica film processor.

Example 1A

Branched Polyamines Inhibit Formation of Nascent $PrP^{Sc}$ and Induce Clearance of Pre-existing $PrP^{Sc}$ Western blots were probed with 3F4 monoclonal antibody which recognizes newly expressed MHM2 PrP. ScN2a cells were exposed to SuperFect™ for 3 h and harvested 3 d after removal of SuperFect™. Gels were run on both undigested, control sample and a sample subjected to limited proteolysis. The samples were run in separate lanes 1–6 with a control and limited proteolysis sample for each of the 6 lanes as follows: Lane 1: DOTAP-mediated transfection. Lane 2: 30 μg/ml SuperFect™, 5 μg pSPOX MHM2. Lane 3: 75 μg/ml SuperFect™, 5 μg pSPOX MHM2. Lane 4: 150 μg/ml SuperFect™, 5 μg pSOX MHM2. Lane 5: 150 μg/ml SuperFect™, 10 μg pSPOX MHM2. Lane 6: No addition of either transfection reagent or DNA. Forty μl of undigested brain homogenate was used in these studies while those samples subjected to limited digestion with proteinase K were concentrated 25-fold prior to SDS-PAGE. One ml of the digest were centrifuged at 100,000×g for 1 h at 4° C. and the pellets suspended in 80 μl of SDS sample buffer prior to SDS-PAGE followed by Western blotting. Apparent molecular weights based on migration of protein standards are 34.2, 28.3, and 19.9 kDa.

All of the control lanes 1–6 show multiple bands as expected. However, of the samples subjected to limited proteolytic only lane 1 shows bands. Unexpectedly, all of the partially digested sample lanes 2–5 show no bands and as expected no bands in the partially digested lane 6. These results show the effect of using SuperFect™ in clearing PrP$^{Sc}$.

Example 1B

The blot described above was stripped of antibody, exposed to labeled R073 and redeveloped. The antibody 3F4 used in Example 1 binds to PrP$^C$ but not to PrP$^{Sc}$. However, R073 binds to PrP$^{Sc}$ and PrP$^C$. Lanes 1, 2 and 3 show decreasing amounts of PrP$^{Sc}$ and lanes 4 and 5 show no detectable PrP$^{Sc}$.

Example 2A

Gels were run on undigested controls 1–4 and as above, samples subjected to limited proteolysis. The lanes were as follows: Lane 1: No SuperFect™. Lane 2: 30 μg/ml SuperFect™. Lane 3: 75 μg/ml SuperFect. Lane 4: 150 μg/ml SuperFect. ScN2a cells were exposed to SuperFect™ for 3 h and harvested 3 d after removal of SuperFect™. Apparent molecular weights based on migration of protein standards are 33.9, 28.8, and 20.5 kDa. In that each sample was tested after the same time period the results show the dose-dependent effect of SuperFect™ on PrP$^{Sc}$ removal. Lanes 1, 2 and 3 show decreasing amounts of PrP$^{Sc}$ and lane 4 shows no detectable PrP$^{Sc}$.

Example 2B

To determine the time-dependent effect of SuperFect™ three different panels with four lanes each were prepared and run as follows: ScN2a cells were exposed to 7.5 μg/ml: SuperFect™ (lanes 1–4), PEI (average molecular weight ~60,000) (lanes 5–8), or PAMAM, generation 4.0 (lanes 9–12). Time of exposure times for each polyamine: 0 hours (lanes 1, 5, and 9), 4 hours (lanes 2, 6, and 10), 8 hours (lanes 3, 7, and 11), 16 hours (lanes 4, 8, and 12). All samples were subjected to limited proteolysis to measure PrP$^{Sc}$. Apparent molecular weights based on migration of protein standards are 38, 26, and 15 kDa. Lanes of each of the three panels show decreasing amounts of PrP$^{Sc}$.

Example 3

In this example four panels A,B, C and D were created with panels having three double (control and test) lanes each. ScN2a cells were exposed to 1.5 μg/ml: (A) SuperFect™, (B) PEI (average molecular weight ~60,000), (C) PAMAM, generation 4.0, or (D) no addition. Cells were harvested: Lane 1, before addition; Lane 2, immediately following 1 week continuous exposure to test compounds; and Lane 3, three weeks after removal of test compounds. Minus (−) symbol denotes undigested, control sample and plus (+) symbol designates sample subjected to limited proteolysis. Apparent molecular weights based on migration of protein standards are 33.9, 28.8, and 20.5 kDa. Test lanes 3 in panel A showed slight PrP$^{Sc}$ after three weeks and test lanes 3 in panels B and C showed no detectable PrP$^{Sc}$ whereas PrP$^{Sc}$ was present in all lanes in panel D.

Example 4A

Four separate gels were run to demonstrate the effect of adding chloroquine would have on PrP$^{Sc}$ levels. The lanes 1 control and 3 where chloroquine was added show clear bands for PrP$^{Sc}$ whereas lanes 2 and 4 with no chloroquine show barely detectable amounts of PrP$^{Sc}$. The four lanes were prepared as follows: ScN2a cells were treated Lane 1: Control media. Lane 2: 7.5 μg/ml PEI (average molecular weight ~60,000). Lane 3: PEI plus 100 μM chloroquine. Lane 4: PEI plus 30 μM NH$_4$Cl. Chloroquine and NH$_4$Cl were added 1 h prior to addition of PEI. Cells were harvested 16 hours after addition of PEI. All samples shown were subjected to limited proteolysis to measure PrP$^{Sc}$. Apparent molecular weights based on migration of protein standards are 38, 26, and 15 kDa.

Example 4B

Eight lanes with SuperFect™ (+SF) and eight lanes without SuperFect™ (−SF) were prepared. Lanes 1–8 of each group had an adjusted pH of 3.6, 4, 5, 6, 7, 8, 9 and 9.6. In vitro mixture of crude mouse brain homogenates with SuperFect™ under a range of pH conditions was performed as described in methods (measured final pH of each sample denoted above the lanes). Addition of 60 μg/ml SuperFect™ denoted as "+SF" and control with no addition as "−SF." All samples shown were subjected to limited proteolysis to measure PrP$^{Sc}$. Apparent molecular weights based on migration of protein standards are 30 and 27 kDa. All lanes of the −SF group showed PrP$^{Sc}$ present. Lanes 3–8 of the +SF group showed PrP$^{Sc}$. However, lanes 1 and 2 with respective pH levels of 3.6 and 4.0 showed very slight detectable PrP$^{Sc}$. The results show that the ability of a blanched polycation such as SuperFect™ to clear PrP$^{Sc}$ is pH dependent.

Example 5

Sixteen different lanes were prepared as described. Lanes 1 and 2 were control lanes and each of lanes 3–16 contained a different compound as tested in Table 2. The test compounds were all polyamines. Thus, the results show removal of PrP$^{Sc}$ from brain homogenate in vitro by various polyamines. Samples were incubated with polyamines at pH 3.6 and processed as described in Methods. Each polyamine was tested at 60 μg/ml concentration. Lanes 1 and 2: control. Lane 3: poly-(L)lysine. Lane 4: PAMAM, generation 0.0. Lane 5: PAMAM, generation 1.0. Lane 6: PAMAM, generation 2.0. Lane 7: PAMAM, generation 3.0. Lane 8: PAMAM, generation 4.0. Lane 9: PAMAM-OH, generation 4.0. Lane 10: PPI, generation 2.0. Lane 11: PPI, generation 4.0. Lane 12: linear PEI. Lane 13: high MW PEI. Lane 14: low MW PEI. Lane 15: average MW PEI. Lane 16: SuperFect. All samples shown were subjected to limited proteolysis to measure PrP$^{Sc}$. Apparent molecular weights based on migration of protein standards are 30 and 27 kDa. Table 2. Removal of PrP$^{Sc}$ by polymer compounds. IC$_{50}$= approximate concentration of polymer required to reduce PrP$^{Sc}$ to 50% of control levels in ScN2a cells after exposure for 16 hours. All compounds were tested at 5 different concentrations. PrP$^{Sc}$ levels were measured by densitometry of Western blot signals.

TABLE 2

(includes information on the characteristics of compounds used but does not correspond directly to lanes 1–16)

| Compound | Mol. Wt. | Primary NH$_2$ groups | IC$_{50}$ (ng/ml) |
| --- | --- | --- | --- |
| PAMAM generation 0.0 | 517 | 4 | >10,000 |
| PAMAM generation 1.0 | 1,430 | 8 | >10,000 |
| PAMAM generation 2.0 | 3,526 | 16 | 2,000 |
| PAMAM generation 3.0 | 6,909 | 32 | 400 |
| PAMAM generation 4.0 | 14,215 | 64 | 80 |
| PAMAM-OH generation | 14,279 | 0 | >10,000 |
| PPI generation 2.0 | 773 | 8 | 2,000 |
| PPI generation 4.0 | 3,514 | 32 | 80 |
| Low MW PEI | ~25,000 | | 2,000 |
| Average MW PEI | ~60,000 | | 400 |
| High MW PEI | ~800,000 | | 80 |
| Linear PEI | ~60,000 | | 2,000 |
| poly-(L)lysine | ~60,000 | >500 | 10,000 |
| SuperFect™ | | | 400 |

Lanes 7, 8, 11 and 13 showed the best results, i.e., best ability to clear PrP$^{Sc}$ under these conditions. Specifically, PAMAM generation 4.0 in lane 8 showed the best ability to clear PrP$^{Sc}$ under these conditions whereas PAMAM-OH generation 4.0 showed almost no detectable ability to clear PrP$^{Sc}$ and was comparable to the control.

Example 6
Transfection of PrP$^{Sc}$ Expressing Cells with Dendrimer Compounds

Cells of neuronal origin expressing PrP$^{Sc}$ were examined for the ability of compounds to suppress PrP$^{Sc}$ formation. Stock cultures of N2a and ScN2a cells were maintained in MEM with 10% FBS, 10% Glutamax (Gibco BRL), 100 U penicillin, and 100 μg/ml streptomycin. Cells from a single confluent 100 mm dish were trypsinized and split into 10 separate 60 mm dishes containing DME plus 10% FBS, 10% Glutamax, 100 U penicillin, and 100 μg/ml streptomycin (supplemented DME) one day prior to transfection. Immediately prior to transfection, the dishes were washed twice with 4 ml supplemented DME media and then drained.

For DOTAP-mediated transfection, 15 μg pSPOX MHM2 was resuspended in 150 μl sterile Hepes Buffered Saline (HBS) on the day of transfection. The DNA solution was then mixed with an equal volume of 333 μg/ml DOTAP (Boehringer Mannheim) in HBS in Falcon 2059 tubes and incubated at room temperature for 10 minutes to allow formation of DNA/lipid complexes. Supplemented DME (2.5 ml) was added to the mixture, and this was then pipetted onto drained cell monolayers. The following day, the medium containing DNA/lipid was removed and replaced with fresh supplemented DME. Cells were harvested three days later.

For SuperFect™-mediated transfections/exposures, SuperFect™ with or without DNA was added to 1 ml supplemented DME in a Falcon 2059 tube to achieve the specific concentrations needed for each experiment. This mixture was pipetted up and down twice and then onto drained cell monolayers. After exposure for the indicated times, the medium containing SuperFect™ was removed and replaced with fresh supplemented DME. Cells were harvested at specified times after removal of SuperFect™.

Exposures to PPI (DAB-Am-8, Polypropylenimine octaamine Dendrimer, Generation 2.0 Aldrich 46,072-9), Intact PAMAM (Starburst (PAMAM) Dendrimer, Generation 4.

Aldrich 41,244-9, PEI (Sigma), poly-(L)lysine (Sigma), and poly-(D) lysine (Sigma) were performed as described above for SuperFect™.

Isolation of Protein from Treated Cells

Cells were harvested by lysis in 1.2 ml of 20 mM Tris pH 8.0 containing 100 mM NaCl, 0.5% NP-40, and 0.5% sodium deoxycholate. Nuclei were removed from the lysate by centrifugation at 2000 rpm for 5 min. This lysate typically had a protein concentration of 0.5 mg/ml measured by the BCA assay. For samples not treated with proteinase K, 40 μl of whole lysate (representing 20 μg total protein) was mixed with 40 μl of 2×SDS sample buffer. For proteinase K digestion, 1 ml of lysate was incubated with 20 μg/ml proteinase K (total protein:enzyme ratio 25:1) for 1 hr at 37° C. Proteolytic digestion was terminated by the addition of 8 μl of 0.5M PMSF in absolute ethanol. Samples were then centrifuged for 75 min in a Beckman TLA-45 rotor at 100,000×g at 4° C. The pellet was resuspended by repeated pipetting in 80 μl of 1×SDS sample buffer. The entire sample (representing 0.5 mg total protein before digestion) was loaded for SDS-PAGE.

Western Blot Analysis

Immunoreactive PrP bands from the DOTAP-mediated transfection were detected before and after digestion with proteinase K with monoclonal antibody 3F4. The construct used to express $PrP^{Sc}$ in the ScN2a cells is MHM2 a chimeric construct that differs from wild-type (wt) MoPrP at positions 108 and 111 (Scott et al. *Protein Sci.* 1:986–997 (1992)). Substitution at these positions with the corresponding residues (109 and 112 respectively) from the Syrian hamster (SHa) PrP sequence creates an epitope for 3F4 (Kascsak et al. *J. Virol.* 61:3688–3693 (1987)), which does not recognize endogenous wt MoPrP in ScN2a cells and hence facilitates specific detection of the transgene by Western blot.

Following electrophoresis, Western blotting was performed as previously described (Scott et al. *Cell* 59:847–857 (1989)). Samples were boiled for 5 minutes and cleared by centrifugation for 1 minute at 14,000 rpm in a Beckman ultrafuge. SDS-PAGE was carried out in 1.5 mm, 12% polyacrylamide gels (Laemmli (1970) *Nature* 227:661–665). Membranes were blocked with 5% nonfat milk protein in PBST (calcium- and magnesium-free PBS plus 0.1% Tween 20) for 1 hour at room temperature. Blocked membranes were incubated with primary RO73 polyclonal or 3F4 monoclonal antibody at a 1:5000 dilution in PBST overnight at 4° C.

Following incubation with primary antibody, membranes were washed 3×10 minutes in PBST, incubated with horseradish peroxidase-labeled secondary antibody (Amersham Life Sciences) diluted 1:5000 in PBST for 25 minutes at room temperature and washed again for 3×10 minutes in PBST. After chemiluminescent development with ECL reagent (Amersham) for 1 minute, blots were sealed in plastic covers and exposed to ECL Hypermax film (Amersham). Films were processed automatically in a Konica film processor.

In contrast to DOTAP-transfected cells, ScN2a cells transfected with varying concentrations of SuperFect™ and DNA did not appear to contain protease-resistant MHM2. Close scrutiny revealed that, prior to protease digestion, SuperFect™—transfected samples express MHM2 bands, which are not seen in the background pattern of the control sample. These observations indicate that MHM2 PrP was successfully expressed using SuperFect™ transfection reagent, but conversion of MHM2 PrP$^C$ to protease-resistant MHM2 PrP$^{Sc}$ was inhibited by SuperFect™.

To examine whether SuperFect™ had affected levels of preexisting PrP$^{Sc}$ in ScN2a cells, the Western blot probed with 3F4 antibody was reprobed with polyclonal antibody RO73, which is able to recognize endogenous MoPrP. Remarkably, SuperFect™ caused the disappearance of preexisting MoPrP$^{Sc}$ from ScN2a cells in a dose-dependent manner. After treatment with SuperFect™, PrP$^{Sc}$ could not be detected in the nuclear fraction, pellet, supernatant, or media. The concentration of SuperFect™ required to fully remove preexisting PrP$^{Sc}$ with a three-hour exposure was 300 μg/ml, whereas 30 μg/ml was sufficient to interfere with the formation of new MHM2 PrP$^{Sc}$ within the same time frame.

Length of exposure dramatically influenced the ability of SuperFect™ to remove PrP$^{Sc}$ from ScN2a cells. Whereas a three-hour exposure to 150 μg/ml SuperFect™ significantly lowered PrP$^{Sc}$ levels in ScN2a cells, exposure for 10 min to the same dose of SuperFect™ did not affect PrP$^{Sc}$ levels. When ScN2a cells were exposed to 2 μg/ml SuperFect™ continuously for 1 week, PrP$^{Sc}$ disappeared completely.

The conditions tested did not appear to be toxic for the cells. Neither 150 μg/ml SuperFect™ for 3 hrs nor 2 μg/ml SuperFect™ continuously for 1 week caused any obvious changes in cell morphology, viability, or growth as judged by phase contrast microscopy.

Example 7
Elimination of PrP$^{Sc}$ by Repeated Exposures to SuperFect™

The duration in the reduction in PrP$^{Sc}$ levels after exposure to SuperFect™ was examined, and it was shown that this reduction could persist for extended periods after removal of SuperFect™. Following the exposure of ScN2a cells to a single dose of 150 μg/ml SuperFect™ for 3 hrs, PrP$^{Sc}$ levels remained low for one week, but returned to near baseline levels after 3 weeks in culture without SuperFect™.

In contrast, when ScN2a cells were exposed to 4 separate doses of SuperFect™ over the course of 16 days, very little PrP$^{Sc}$ could be detected 4 weeks after the final exposure to SuperFect™. This result offers hope that prolonged exposure to SuperFect™ may lead to long term cure of scrapie infection in cultured cells.

Example 8
SuperFect™ does not Destroy PrP$^{Sc}$ Directly

The dendrimer SuperFect™ was used to determine if it could exert a similar inhibitory effect on PrP$^{Sc}$ in either crude brain homogenates or purified PrP 27–30 rods. Brain homogenates from normal and scrapie-affected Syrian hamsters (10% (w/v) in sterile PBS) were prepared by repeated extrusion through syringe needles of successively smaller size, from 18 to 22 gauge. Nuclei and debris were removed by centrifugation at 1000×g for 10 min. The bicinchoninic acid (BCA) protein assay (Pierce) was used to determine protein concentration. Homogenates were adjusted to 10 mg/ml protein with PBS and 50 μl was added to 450 μl of lysis buffer containing 100 mM NaCl, 1 mM EDTA, 0.55% sodium deoxycholate, 0.55% Triton X-100, and 50 mM Tris-HCl pH 7.5. This mixture was then incubated with 0–300 μg/ml SuperFect™ for 3 hrs at 37° C. and then centrifuged for 10 min at 14,000 rpm in a Beckman Ultrafuge. The pellet was resuspended in 450 μl lysis buffer without SuperFect™. Proteinase K (Boehringer Mannheim) was added to achieve a final concentration of 20 μg/ml, and thus the ratio of total protein/enzyme was 50:1. Samples were incubated for 1 h at 37° C. Proteolytic digestion was terminated by the addition of 8 μl of 0.5 M PMSF in ethanol. Samples were then centrifuged for 75 min in a Beckman TLA–45 rotor at 100,000×g at 4° C. Undigested samples (10 μl) were mixed with an equal volume of 2×SDS sample buffer. For digested samples, the pellet was resuspended by repeated pipetting in 100 μl 1×SDS sample buffer. Twenty μl (equivalent to 100 μg of total protein prior to proteinase K digestion) of each sample was loaded for SDS-PAGE.

PrP 27–30 rods were purified from scrapie-affected Syrian hamster brains and previously described (Prusiner et al. *Cell* 35:349–358 (1983)). Purified rods (3.5 μg/ml) were incubated with or without 900 μg/ml SuperFect™ in 100 μl supplemented DME. After 16 hrs at 37° C., the suspension was centrifuged at 100,000×g at 4° C. The pellet was resuspended in 500 μl of buffer containing 1 mg/ml BSA, 100 mM NaCl, 1 mM EDTA, 0.55% sodium deoxycholate, 0.55% Triton X-100, and 50 mM Tris-HCl pH 7.5. Proteinase K was added to achieve a final concentration of 20 μg/ml. Samples were incubated for 1 h at 37° C. Proteolytic digestion was terminated by the addition of 8 μl of 0.5 M Pefabloc (Boehringer Mannheim). Samples were then centrifuged for 75 min at 100,000×g at 4° C. Undigested samples (50 μl) were mixed with an equal volume of 2×SDS sample buffer. For digested samples, the pellet was resuspended by repeated pipetting in 100 μl 1×SDS sample buffer. Forty μl of each sample was loaded for SDS-PAGE.

When SuperFect™ was mixed with either crude homogenates of scrapie-affected Syrian hamsters or with purified Syrian hamster PrP 27–30, there was no significant change in the level of proteinase K-resistant PrP$^{Sc}$. These results suggest that the removal of PrP$^{Sc}$ from ScN2a cells by SuperFect™ depends on the presence of intact cellular machinery.

Example 9
Clearance of PrP$^{Sc}$ Levels by other Dendritic Polycations

The SuperFect™ compound is a high molecular weight component of heat-degraded PAMAM Starburst dendrimers, which is a cationic, highly-branched, monodisperse polymers (Tang et al., *Bioconjugate Chem.* 7:703–714 (1996)). To identify other potentially useful anti-prion therapeutic agents, three other dendritic polycations and two linear cationic polymers were screened for their ability to clear PrP$^{Sc}$ from ScN2a cells. Among the dendritic macromolecules tested, polyetheleneimine (PEI) was the most potent, removing the majority of PrP$^{Sc}$ from ScN2a cells after 3 hrs when used at a concentration of 10 μg/ml. Intact PAMAM displayed a potency comparable to SuperFect™, removing approximately half of the detectable PrP$^{Sc}$ when used at a concentration of 50 μg/ml. In contrast, the dendrimer polypropyleneimine (PPI), poly-(L)lysine, and the linear polycation poly-(D)lysine failed to reduce PrP$^{Sc}$ levels at concentrations between 10–50 μg/ml. These results demonstrate that a branched polymeric architecture is required to clear PrP$^{Sc}$. Furthermore, exposure of ScN2a cells to either PEI or intact PAMAM for one week at a concentration of 1.5 μg/ml completely removes PrP$^{Sc}$, effectively curing the cells of scrapie infection.

Example 10
Branched Polyamines Cure Prion-Infected Neuroblastoma Cells

The above Examples show that branched polyamines purged scrapie-infected neuroblastoma (ScN2a) cells of PrP$^{Sc}$, the protease-resistant isoform of the prion protein. The ability of these compounds to eliminate PrP$^{Sc}$ from ScN2a cells depended upon certain molecular characteristics. In particular, active compounds were highly branched and possessed a high surface density of primary amino groups. The most potent compounds identified were generation 4.0 polyamidoamide (PAMAM) and polypropyleneimine (PPI) dendrimers. Dendrimers are branched polyamines manufactured by a repetitive divergent growth technique, allowing the synthesis of successive, well-defined "generations" of homodisperse structures. The following experimental results demonstrate that branched polyamines cure prion-infected cells. The site and mechanism of action for these compounds was also determined.

Materials and Methods

Chemical compounds. High molecular weight PEI was purchased from Fluka. SuperFect™ transfection reagent was purchased from QIAGEN®. All other polyamines were purchased from Sigma-Aldrich. Fluorescein-labeled PPI was synthesized as follows: 30 mg fluorescein isothiocyanate (FITC) was mixed with 1 mg PPI generation 4.0 in 2 ml absolute ethanol overnight at 4° C. A 3:1 excess of PPI-to-FITC equivalent groups was set up to minimize the production of multiple FITC conjugates per PPI. Labeled PPI was separated from residual, unreacted FITC using a 12 mm×37 cm Sephadex P-2 column equilibrated in 0.15 mM NaCl buffer. Fractions were collected and analyzed by thin layer chromatography for single spots of fluorescence and amine content. Fluorescence was detected using a long wave UV lamp, and primary amines were detected by ninhydrin assay. Appropriate fractions were combined and lyophilized. The dry powder was brought up in sterile water, titrated to pH 7.0, diluted in 5% glucose, 5 mM HEPES pH 7.4, and filtered through a 0.2 Fm polycarbonate membrane. FITC concentration of this stock solution was 44.1 FM, as measured by UV spectroscopy with an absorbance maxima at 489 nm. Final PPI concentration was 50 FM.

Cultured Cells

Cultures of ScN2a cells were maintained in DME pH 7.4 with 10% FBS, 10% Glutamax (Gibco BRL), 100 U/ml penicillin, and 100 Fg/ml streptomycin (supplemented DME). Cultures were split 1:10 weekly, and fed fresh medium twice weekly. Cytotoxicity after treatment with polyamines was assessed in ScN2a cells by four methods: (1) examination of morphology under phase contrast microscopy, (2) observation of growth curves and cell counts for three weeks after treatment, (3) vital staining of living cells with 0.4% trypan blue (Sigma-Aldrich), and (4) assay of dehyrogenase enzymes with 93-[4,5-Dimethylthiazol-2-yl]-2,5-diphenyltetrazolium bromide (MTT). For the dehyrogenase assay, cells in 96-well plates were incubated with 0.5 mg/ml MTT (Sigma-Aldrich) in supplemented DME for 4 hrs. Media was then aspirated and cells were dissolved in isopropanol containing 50 mM HCl. Converted MTT was measured by absorbance at 570 nm. For ScN2a cells treated with either PAMAM or PPI generation 4.0 continuously for 1 week, $LD_{50}$~50 Fg/ml.

To prepare samples for infectivity assays, 100 mm plates (Falcon) of confluent cells were washed with 3×5 ml PBS, scraped into 2 ml PBS, and homogenized by repeated extrusion through a 26 gauge needle. Prion infectivity was determined by intracerebral inoculation of 30 Fl cell homogenate into Tg(MoPrP)4053 mice. Mice were observed for clinical signs of scrapie, and a subset of diagnoses were confirmed by neuropathological examination.

To prepare samples for SDS-PAGE, plates were drained of media and adherent cells were lysed in 1 ml 20 mM Tris pH 8.0, 100 mM NaCl, 0.5% NP-40, 0.5% sodium deoxycholate. Samples were adjusted to obtain a total protein concentration of 1 mg/ml measured by the bicinchnoninic (BCA) assay (Pierce). Nuclei were removed from the lysate by centrifugation at 2000 rpm for 5 min. For samples not treated with proteinase K, 10 Fl of lysate was mixed with an equal volume of 2×SDS reducing sample buffer. For proteinase K digestion, 20 Fg/ml proteinase K (Boehringer Mannheim) (total protein:enzyme ratio 50:1) was incubated with 1 ml lysate for 1 hr at 37° C. Proteolytic digestion was terminated by the addition Pefabloc (Boehringer Mannheim) to a final concentration of 5 mM. Samples were then centrifuged at 100,000×g for 1 hr at 4° C. and the pellet fractions were resuspended in 80 Fl of reducing SDS sample buffer. Twenty microliter samples were loaded per lane on 1 mm 12% Tris glycine SDS-PAGE gels (Novex).

Mixture of brain homogenates and purified prions with polyamines in vitro. Brain homogenates from scrapie-infected rodents (10% (w/v) in sterile water) were prepared by repeated extrusion through syringe needles of successively smaller size, from 18 to 22 gauge. Nuclei and debris were removed by centrifugation at 1000×g for 5 min. Homogenates were adjusted to 1 mg/ml protein in 1% NP-40. For incubations with PPI, 50 Fl 1 mg/ml brain homogenate was mixed with 450 Fl 1% NP40, 50 mM sodium acetate pH 3.0 (final measured pH=3.6) plus or minus 60 Fg/ml PPI generation 4.0 and shaken constantly for various periods at 37° C.

Purified prions were prepared as described previously, utilizing both proteinase K digestion and sucrose gradient sedimentation, and resuspended in 1% NP-40, 1 mg/ml BSA. For pH studies, 475 Fl of 0.5 Fg/ml purified RML PrP27–30 in 1% NP-40, 1 mg/ml BSA was mixed with 25 Fl 1M buffers from pH 3–8 (sodium acetate for pH 3–6 and Tris acetate for pH 7–8) plus or minus 60 Fg/ml PPI generation 4.0 for 2 hrs at 37° C. with constant shaking. The final pH value of each sample was measured directly with a calibrated pH electrode (Radiometer Copenhagen). For compound screening, 475 Fl of 0.5 Fg/ml purified RML PrP27–30 in 1% NP-40, 1 mg/ml BSA was mixed with 25 Fl 1M sodium acetate pH 3.0 plus 60 Fg/ml polyamine for 2 hrs at 37° C. with constant shaking.

Following incubations, each sample was neutralized with an equal volume 0.2 M HEPES pH 7.5 containing 0.3 M NaCl and 4% Sarkosyl. Samples not treated with proteinase K were mixed with equal volume 2×SDS sample buffer. For proteinase K digestion, samples were incubated with 20 Fg/ml proteinase K (Boehringer Mannheim) (total protein:enzyme ratio 25:1) for 1 hr at 37° C. Proteolytic digestion was terminated by the addition of 8 $\mu$l of 0.5M PMSF in absolute ethanol. Digested samples were then mixed with equal volumes 2×SDS sample buffer. All samples were boiled for 5 min prior to electrophoresis. SDS-PAGE was performed on 1.5 mm 12% polyacrylamide gels.

Western blotting. Following electrophoresis, Western blotting was performed as previously described. Membranes were blocked with 5% non-fat milk protein in PBST (calcium- and magnesium-free PBS plus 0.1% Tween 20) for 1 hr at room temperature. Blocked membranes were incubated with 1 Fg/ml recombinant, humanized Fab d13 in PBST for 1 hr at 4° C. Following incubation with primary Fab d13, membranes were washed 3×10 min in PBST, incubated with horseradish peroxidase-labeled anti-human Fab secondary antibody (ICN) diluted 1:5000 in PBST for 45 min at room temperature and washed again for 4×10 min in PBST. After chemiluminescent development with ECL reagent (Amersham) for 1–5 min, blots were sealed in plastic covers and exposed to ECL Hypermax film (Amersham). Films were processed automatically in a Konica film processor.

Negative stain electron microscopy. Sample preparation was done on carbon-coated 600 mesh copper grids that were glow-discharged for 30 sec prior to staining. Five microliter samples were adsorbed to grids for 30–60 sec, washed with 2 drops of 0.1 M and 0.01 M ammonium acetate each, and stained with 2 drops of freshly filtered 2% ammonium molybdate or uranyl acetate. After drying, samples were viewed in a Jeol JEM 100CX II electron microscope at 80 kV at a standard magnification of 40,000. The magnification was calibrated using negatively-stained catalase crystals.

Confocal microscopy. Confocal images were obtained using a BioRad laser scanning confocal microscope (MRC-1024, Hercules, Calif.), outfitted with a Nikon Diaphot 200 microscope and a Helium/Neon laser. A 60X Nikon planAPO lens was used, with an additional software zoom function. Laser power was set at 10%, and scanned with a slow speed across the sample. Individual laser lines confirmed the lack of "bleed through" between detection channels. The images were averaged with a Kalman filter (n=4).

Figure 2A:
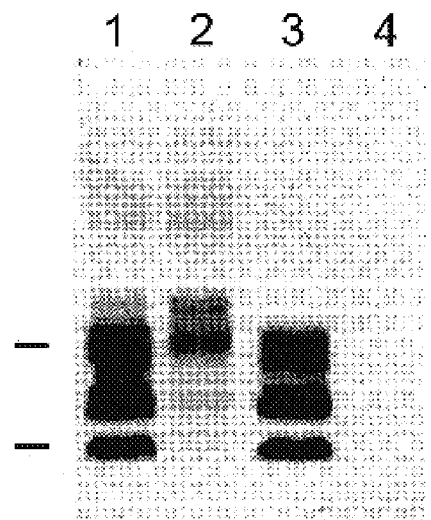
FIG. 2A and FIG. 2B are photographs of gels.

ScN2a cells were incubated with 3 Fg/ml PPI in supplemented DME for 4 weeks, and then cultured for an additional 2 weeks in polyamine-free medium. This transient exposure to PPI was not cytotoxic (see Methods) and completely purged the cells of protease-resistant $PrP^{Sc}$ (FIG. 2A, lanes 2 and 4). In contrast, protease-sensitive $PrP^{C}$ bands migrating between 32–38 kDa appear unaltered by PPI treatment (lanes 1 and 3).

Figure 2B:
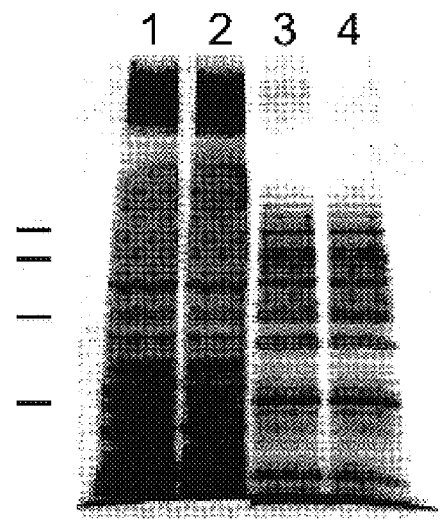
Figure 2C:
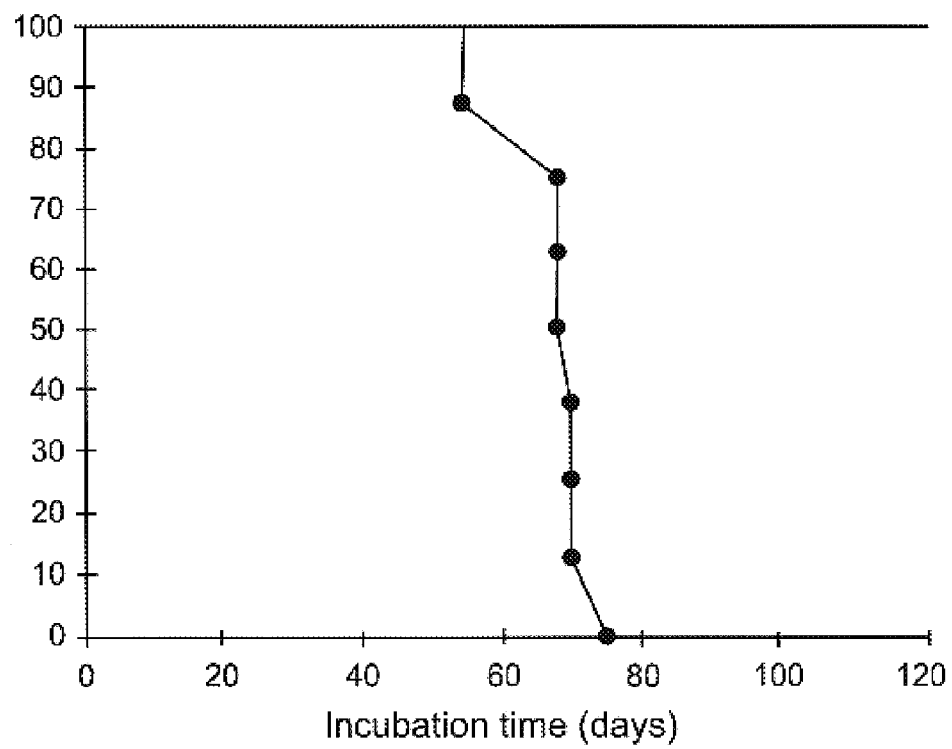
FIG. 2C is a graph of data plotted to indicate survival rates.

Elimination of $PrP^{Sc}$ appeared to be relatively specific since the steady-state levels of proteins in PPI-treated cells was similar to those in control ScN2a cells (FIG. 2B). To assess the effect of PPI treatment on prion infectivity, homogenates prepared from polyamine-treated and control ScN2a cells were inoculated into Tg(MoPrP)4053 mice. The average scrapie incubation time was 67+2 days for mice inoculated with control ScN2a cells and>120 days for mice inoculated with ScN2a cells treated with PPI ($n/n_0$=0/10) (FIG. 2C). These incubation times indicate that the titer of infectious prions in ScN2a cells was reduced from ~$10^7$ $LD_{50}$ units/100 mm plate to <1 $LD_{50}$ unit/plate by PPI treatment. Thus, exposure to PPI completely eliminates prion infectivity from ScN2a cells.

Treatment of scrapie-infected neuroblastoma cells with polyamidoamide dendrimer. ScN2a cells were treated with 3 Fg/ml PPI generation 4.0 in supplemented DME or control media for 4 weeks. After 2 additional weeks of culture in compound-free media, cells were harvested for analysis. (FIG. 2A) PrP immunostain with recombinant Fab d13 was performed as described in the Methods section. Apparent molecular weights based on migration of protein standards are 30 and 27 kDa. (FIG. 2B) Silver stain was performed as previously described. Apparent molecular weights based on migration of protein standards are 49, 36, 25, and 19 kDa. (FIGS. 2A and 2B) Samples subjected to SDS-PAGE were assigned lanes as follows: (FIG. 2A, lanes 1 and 3) control cells, (FIG. 2A, lanes 2 and 4) PPI-treated cells. Lanes (1) and (2) contain undigested lysates, and lanes (3) and (4) contain lysates subjected to limited proteolysis with proteinase K. FIG. 2C is an infectivity bioassay of cell homogenates in Tg(MoPrP)4053 indicator mice: (Filled circles) control cells, (Open squares) PPI-treated cells.

Example 11

Branched Polyamines Act Directly on Purified RML Prions

Because branched polyamines reduce prion infectivity, the next step was to determine the mechanism by which these compounds eliminate $PrP^{Sc}$. An initial objective was to determine the molecular target of branched polyamines. A previously described in vitro assay was used to show that these compounds could render $PrP^{Sc}$ protease-susceptible when mixed directly with crude brain homogenates. A similar assay was carried out with purified RML PrP27–30 prions to determine whether or not the molecular target of branched polyamines was present in this highly purified preparation. $PrP^{Sc}$ in purified preparations of RML PrP27–30 were rendered protease-sensitive by branched polyamines with a similar acidic pH optimum (FIG. 3A) and structure-activity profile (FIG. 3B) as previously obtained in crude brain homogenates. These results indicate that the molecular target of branched polyamines must either be: (1) $PrP^{Sc}$ itself, (2) an acid-induced unfolding intermediate of $PrP^{Sc}$; or (3) a very tightly bound, cryptic molecule which copurifies with $PrP^{Sc}$.

FIGS. 3A and B show a mixture of purified prions with branched polyamines in vitro. FIG. 3A shows samples containing 0.5 Fg/ml purified mouse RML PrP27–30 in 1 mg/ml BSA incubated for 2 hrs at 37° C. with 60 Fg/ml PPI generation 4.0 or control buffer at different pH values as indicated. FIG. 3B shows samples containing 0.5 Fg/ml purified mouse RML PrP27–30 in 1 mg/ml BSA incubated for 2 hrs at 37° C. with various polyamines: (lanes 1–2) control, (lane 3) poly-(L)lysine, (lane 4) PAMAM 0.0, (lane 5) PAMAM 1.0, (lane 6) PAMAM 2.0, (lane 7) PAMAM 3.0, (lane 8) PAMAM 4.0, (lane 9) PAMAM-OH 4.0, (lane 10) PPI 2.0, (lane 11) PPI 4.0, (lane 12) linear PEI, (lane 13) high MW PEI, (lane 14) low MW PEI, (lane 15) average MW PEI, (lane 16) Qiagen SuperFect. All compounds were tested at a concentration of 60 Fg/ml. Western immunoblotting was performed with recombinant Fab d13 for both FIGS. 3A and 3B. Apparent molecular weights based on migration of protein standards are 30 and 27 kDa.

Example 12

$PrP^{Sc}$ Susceptibility to PPI-induced Conformational Change is Sequence- and Strain-specific Although the PrP sequence is well conserved among mammals, a small number of amino acid substitutions appear to hinder prion transmission across species. Furthermore, prions can exist as different phenotypic strains that yield distinct incubation times, neuropathology, and distribution of $PrP^{Sc}$ upon infection of susceptible hosts. In certain cases, these phenotypic differences can be correlated with differences in the conformation of $PrP^{Sc}$. An effort was made to determine whether different species and strains of rodent prions, which presumably contain different conformations of $PrP^{Sc}$, vary in their susceptibility to branched polyamines. Homogenates were prepared from the brains of rodents infected with one of several Syrian hamster (SHa), mouse (Mo), or artificial prion strains. Individual samples were mixed with 60 Fg/ml PPI generation 4.0 in vitro for 2 h at 37° C., neutralized, and subjected to limited proteolysis. The results indicate that susceptibility to PPI dendrimer is dependent on both prion strain and PrP sequence (FIG. 4A).

The varying susceptibility of different strains is most clearly illustrated by the 6 mouse strains analyzed (paired lanes 7–12). Mo(RML), Mo(22a), and Mo(139A) were susceptible to PPI-induced conformational change (paired lanes 7, 9, and 11, respectively). In contrast, Mo(Me7) and Mo(87V) were resistant (paired lanes 8 and 10, respectively); and Mo(C506) was marginally susceptible to PPI-induced conformational change (paired lane 12).

The effect of PrP sequence can be seen by comparing the relative susceptibilities of SHa(RML), MH2M(RML), and Mo(RML). Whereas Mo(RML) was susceptible to PPI-induced conformational change (paired lane 7), SHa(RML) was resistant (paired lane 4). MHM2(RML) displayed an intermediate level of susceptibility to PPI (paired lane 5);

MHM2 is a chimeric PrP molecule in which amino acids 94 to 188 of the mouse sequence have been replaced by the corresponding SHa residues. Thus, SHaPrP$^{Sc}$ appears to be more resistant to PPI-induced conformational change than MoPrP$^{Sc}$.

The varying susceptibilities to PPI displayed by different strains and species of prions, which might be caused by kinetic differences, was investigated. To test this possibility, samples of each prion isolate were incubated with PPI generation 4.0 for varying periods of time. Even after incubation with PPI for 3 days, PrP$^{Sc}$ in samples of resistant isolates did not become more susceptible to protease digestion (for example, FIG. 4B). Thus, the differences in susceptibilities of different prion strains and sequences are not caused simply by differences in the kinetics of PrP$^{Sc}$ unfolding.

Figure 4A:
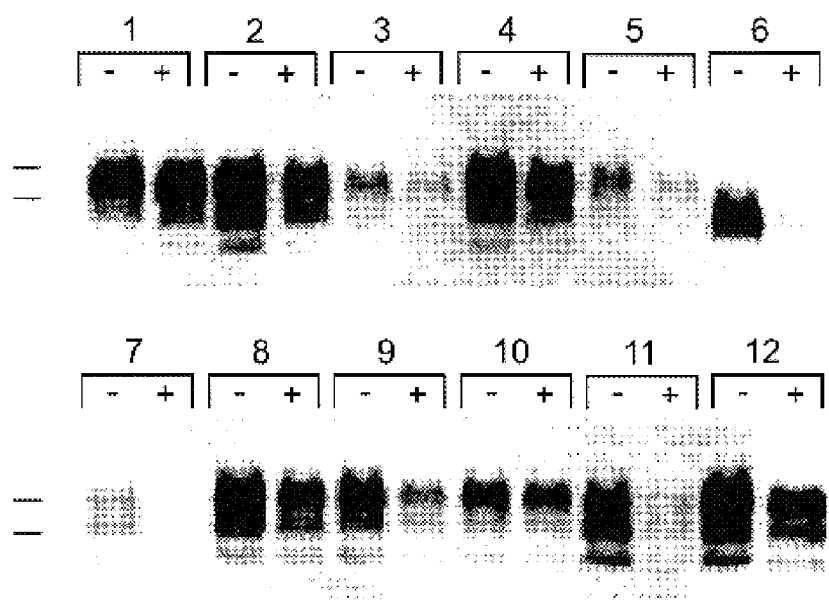
FIG. 4 includes double gel panel 4A and double gel panel 4B. Within the upper panel 4A there is a showing that different strains of prions have different susceptibility to dendrimers indicating that specific dendrimers could be used to determine the type of infectivity (prion strain) in a sample with similar results shown in FIG. 4A.

The results shown in FIG. 4 show the treatment of different prion strains with polypropyleneimine in vitro (FIG. 4A). Samples containing 1% (w/v) various brain homogenates were incubated for 2 hrs at 37° C. with 60 Fg/ml PPI generation 4.0. Paired lanes are designated as follows: (lane 1) SHa(Sc237), (lane 2) SHa(139H), (lane 3) SHa(drowsy), (lane 4) SHa(RML), (lane 5) Tg(MH2M) Prnp$^{0/0}$(RML), (lane 6) Tg(PrP106) Prnp$^{0/0}$(RML), (lane 7) mouse(RML), (lane 8) mouse(Me7), (lane 9) mouse(22a), (lane 10) mouse(87V), (lane 11) mouse(139A), (lane 12) mouse(C506). Minus (−) symbol denotes undigested, control sample and plus (+) symbol designates sample subjected to limited proteolysis by proteinase K.

Figure 4B:
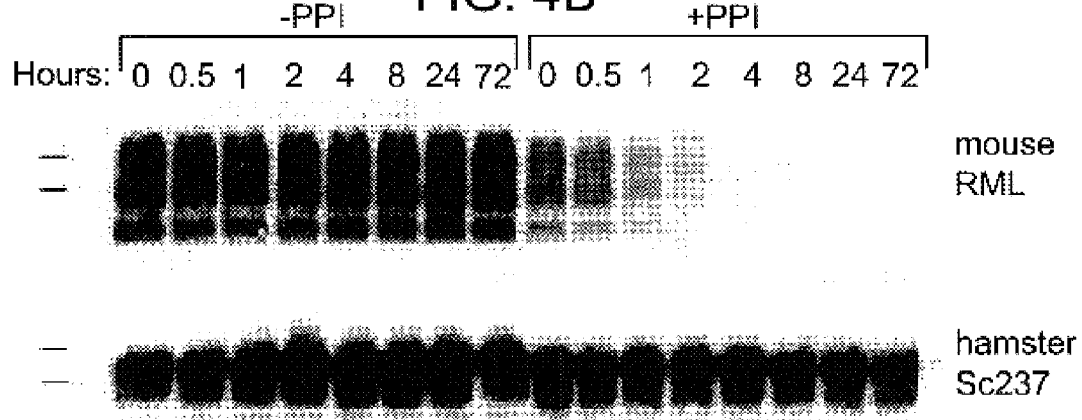

FIG. 4B shows samples containing 1% (w/v) mouse (RML) or SHa(Sc237) incubated at 37° C. with 60 Fg/ml PPI generation 4.0 or control buffer for the time periods indicated. Western immunoblotting was performed with recombinant Fab d13 for both FIGS. 4A and 4B. Apparent molecular weights based on migration of protein standards are 30 and 27 kDa. Prion strains were obtained from the following sources: SHa(Sc237), Mo(139A), and Mo(Me7) from R. Kimberlin; SHa(139H) from R. Carp; SHa(drowsy) from R. Marsh; Mo(RML) from W. Hadlow; Mo(22a) and Mo(87V) from A. Dickenson; Mo(C506) from J. Gibbs. SHa(RML) was obtained by passaging Mo(RML) directly into Syrian hamsters. The passage histories of other strains have been reviewed (Ridley, 1996).

Example 13
Branched Polyamines Assist PrP$^{Sc}$ Disaggregation

Figure 5A:
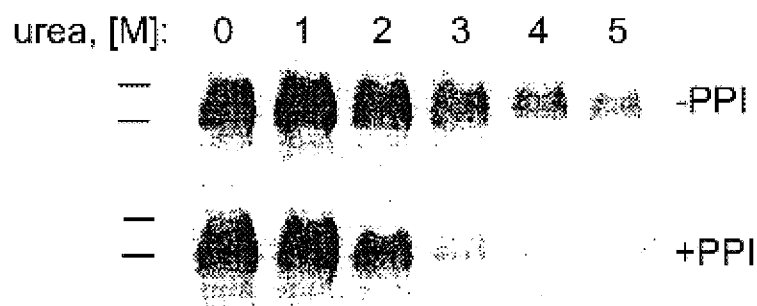
FIG. 5 includes gel panels A, B, C and D.
FIG. 5B indicates that the particular dendrimers tested are most effective at approximately 37 C.
FIGS. 5C and 5D show that dendrimer induced inactivation of prions is irreversible.
Figure 5B:
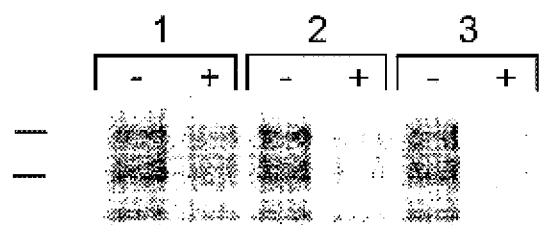

The existence of prion strains resistant to branched polyamines suggests that PrP$^{Sc}$ molecules in these strains might exist in conformations which are more resistant to denaturation than PrP$^{Sc}$ molecules in polyamine-susceptible strains. To test this hypothesis, an examination was made of the effect of adding urea to SHa(Sc237) brain homogenate treated with and without PPI generation 4.0. In the presence of urea, PrP$^{Sc}$ was more susceptible to protease digestion in samples treated with PPI, whereas no difference in protease-resistance could be detected in the absence of urea (FIG. 5A). Thus, additional denaturation enables PrP$^{Sc}$ molecules in a resistant strain to become susceptible to branched polyamines. This result suggests that the general mechanism of action of branched polyamines might be to assist PrP$^{Sc}$ denaturation. Consistent with this concept, branched polyamines render PrP$^{Sc}$ protease-sensitive more efficiently at lower pH values (FIG. 4A) and higher temperatures (FIG. 5B). Furthermore, polyamine-treated PrP$^{Sc}$ did not regain protease-resistance after prolonged neutralization (FIG. 5C) or dialysis (data not shown). Finally, the possibility was excluded that acidification might be required only to activate the dendrimer. It was demonstrated that pre-acidified PPI generation 4.0 could not render PrP$^{Sc}$ protease-sensitive at neutral pH (FIG. 5D).

Figures 6A, 6B:
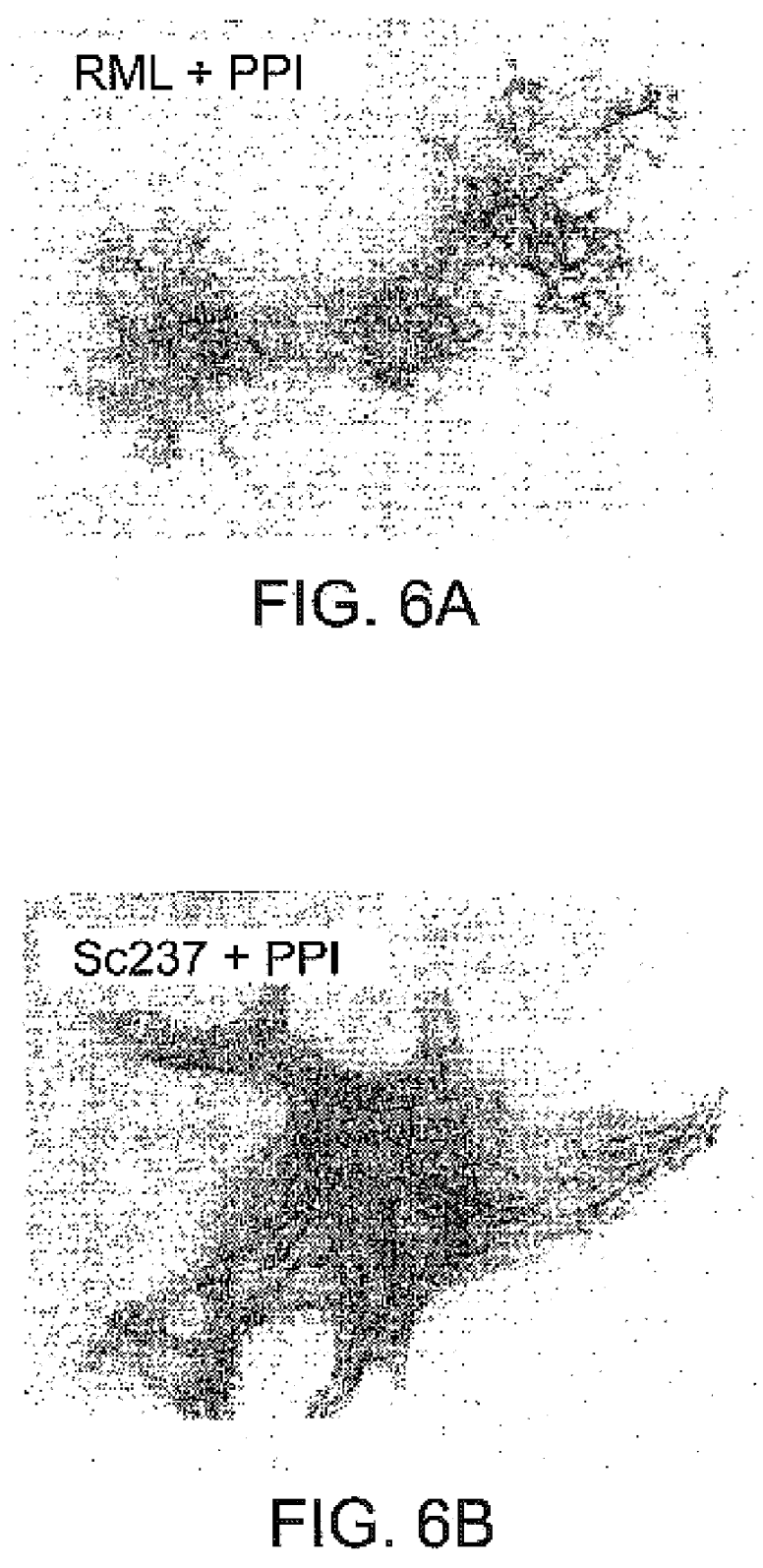

To visualize the effect of branched polyamines on prions, the ultrastructure of purified prion rods treated in vitro with PPI generation 4.0 was examined. By electron microscopy, Mo(RML) PrP27–30 rods were disaggregated after incubation for 2 hrs at 37° C. with PPI (FIG. 6B). In contrast, SHa(237) PrP27–30 rods remained intact after treatment with PPI (FIG. 6D).

To investigate further the mechanism of polyamine-induced disaggregation of PrP$^{Sc}$, a kinetic study in vitro was performed using purified RML PrP27–30 and various concentrations of PPI. The results indicate that polyamine-induced PrP$^{Sc}$ disaggregation is not a catalytic process, and requires a stoichiometry of approximately 1 PPI molecule per 5 RML PrP27–30 molecules in purified prion preparations.

Denaturation of PrP$^{Sc}$ is enhanced by polypropyleneimine, as shown in FIG. 5A. Samples containing 1% (w/v) SHa(Sc237) brain homogenates were incubated for 2 hrs at 37° C. with 60 Fg/ml PPI generation 4.0 or control buffer, plus various concentrations of urea as indicated. All samples were subjected to limited proteolysis. FIG. 5B shows samples containing 0.5 Fg/ml purified mouse RML PrP27–30 in 1 mg/ml BSA incubated for 2 hrs at various temperatures with 60 Fg/ml PPI generation 4.0. Paired lanes are designated as follows: (lane 1) 4° C. (lane 2) 20° C., (lane 3) 37° C. Minus (−) symbol denotes undigested, control sample and plus (+) symbol designates sample subjected to limited proteolysis.

Figure 5C:
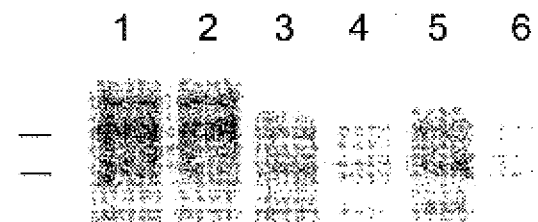
Figure 5D:

FIG. 5C shows samples containing 1% mouse(RML) brain homogenate in 1% NP40, 50 mM sodium acetate pH 3.6 incubated at 37° C. for 2 hrs with either: (odd lanes) no addition or (even lanes) 60 Fg/ml PPI. All samples were neutralized with an equal volume 0.2 M HEPES pH 7.5 containing 0.3 M NaCl and 4% Sarkosyl. Lanes 1 and 2 samples not subjected to protease digestion, lanes 3 and 4 samples immediately subjected to limited proteinase K digestion, lanes 5 and 6 samples incubated at pH 7.5 for an additional 16 hrs at 37° C. before proteinase K digestion.

FIG. 5D shows samples containing 1% mouse(RML) brain homogenate treated in the following manner: (lane 1) control sample at pH 3.6, (lane 2) mixed with 60 Fg/ml PPI at pH 3.6 for 2 hrs, (lane 3) mixed with 60 Fg/ml PPI at pH 7.0 for 2 hrs, (lane 4) incubated alone at pH 3.6 for 2 hrs and then mixed with 60 Fg/ml PPI (pre-titrated to pH 7.0) for 10 min, (lane 5) incubated alone at pH 7.0 for 2 hrs and then mixed with 60 Fg/ml PPI (pre-titrated to pH 3.0) for 10 min. All incubations were carried out at 37° C. Minus (−) symbol denotes undigested, control sample and plus (+) symbol designates sample subjected to limited proteolysis by proteinase K. Western immunoblotting was performed with recombinant Fab d13 for FIGS. 5A–D. Apparent molecular weights based on migration of protein standards are 30 and 27 kDa.

FIG. 6 shows the ultrastructure of purified prion rods treated with polyproplyeneimine in vitro. Samples of purified 100 Fg/ml PrP27–30 in 0.1% NP40, 50 mM sodium acetate pH 3.0 buffer were shaken continuously for 2 hrs at 37° C. Samples were then prepared for negative stain electron microscopy as described in Methods. FIG. 6A is mouse(RML) plus 60 Fg/ml PPI generation 4.0, and FIG. 6B is SHa(Sc237) plus 60 Fg/ml PPI generation 4.0. Negative stain used was 2% uranyl acetate; scale bar=100 nm.

Example 14
PPI Accumulates in Lysosomes

Figure 3A:
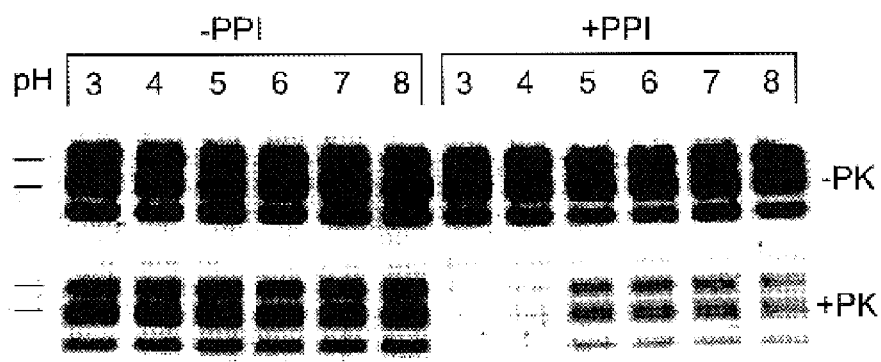
FIG. 3 includes gel panels 3A and 3B and within FIG. 3A columns 3 and 4 labeled +PK (proteinase K) show that dendrimers are effective in removing prions best at a pH of less than 4.
FIG. 3B shows that several different types of dendrimers are effective in inactivating prion infectivity.
Figures 7A, 7B, 7C:
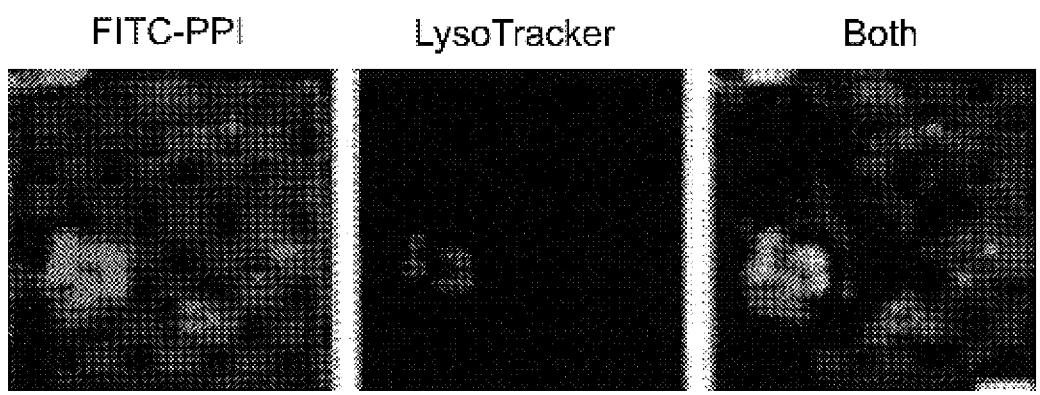
FIG. 7 includes photographs of 7A, 7B and 7C using a fluorescein-labeled PPI which demonstrates that dendrimers are effective inside lysosomes.
Figure 8A:
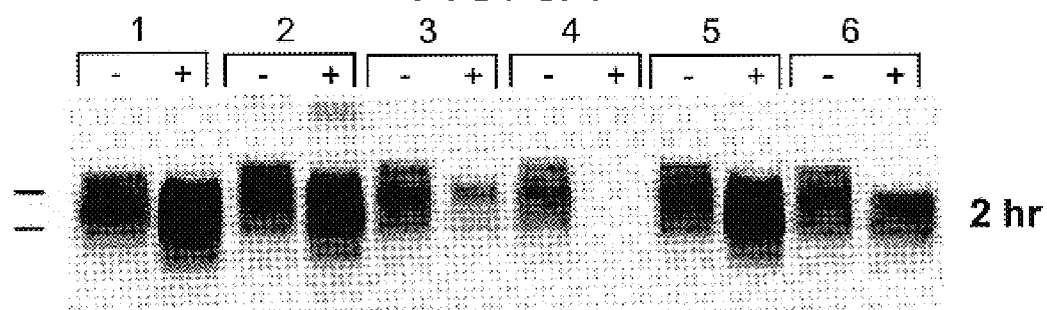
FIG. 8 includes gel panels 8A (2 hours) and 8B (5 minutes). Within FIG. 8A column 4 (+) shows that SDS at a pH of about 3.3 completely eliminates $PrP^{C}$ whereas 1% SDS at a pH of 7.0 is not effective.
FIG. 8B within column 4 shows that 1% SDS at a pH of 3.3 is effective in inactivating prions after only five minutes of exposure.
Figure 8B:
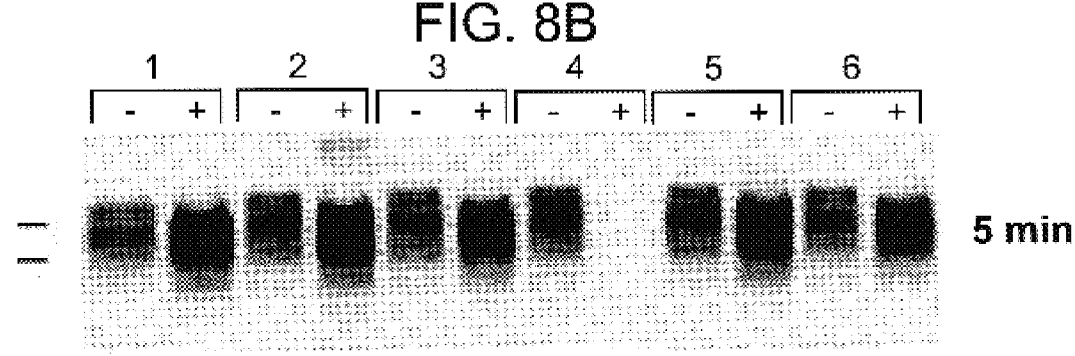
Figure 9:
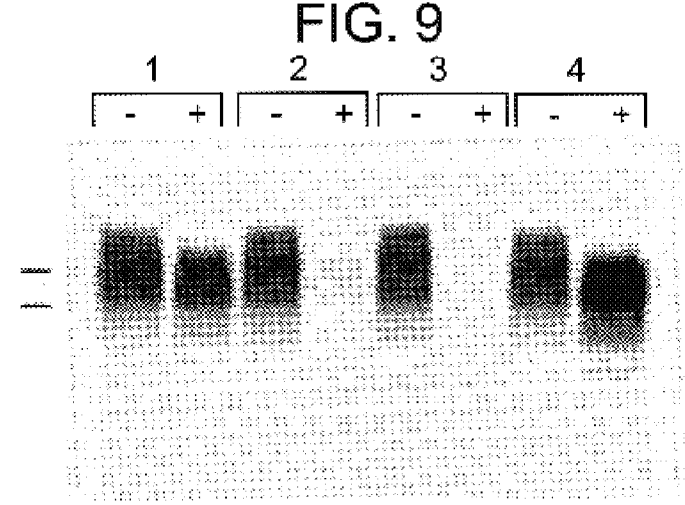
FIG. 9 includes a gel panel wherein columns show results carried out at different temperatures indicating that the optimal temperature for using acetic SDS to eliminate prions is greater than 20° C.
Figure 10:
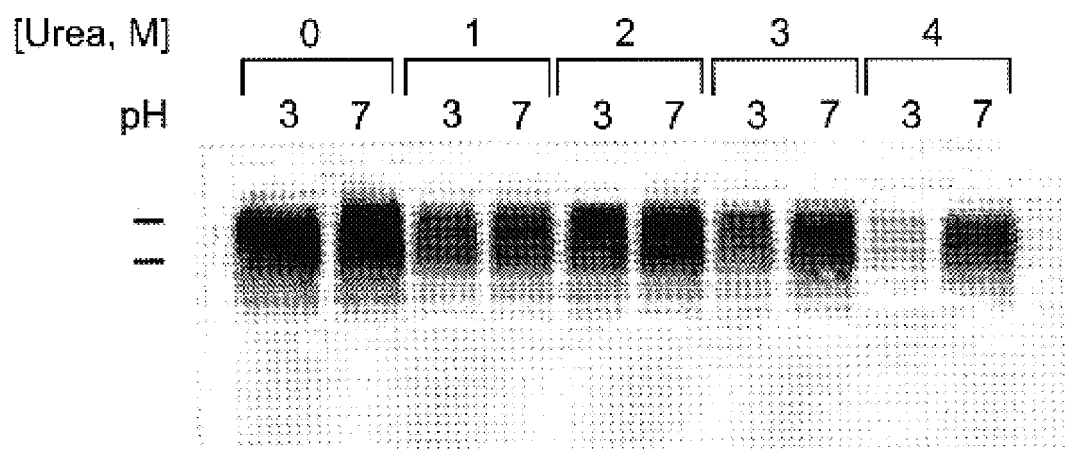
FIG. 10 shows that urea (column 4) is also effective in inactivating prions under acetic conditions.

Branched polyamines apparently require acidic conditions to render PrP$^{Sc}$ protease-sensitive when mixed with brain homogenates or purified prions in vitro, as shown in FIG. 3A. However, these compounds successfully cure living culture media buffered at pH 7.4, as shown in FIG. 2. One possible explanation for this discrepancy is that branched polyamines might co-localize with prions within an acidic intracellular compartment. PrP$^{Sc}$ has previously been shown to accumulate in lysosomes. Therefore, it was investigated whether branched polyamines localize to this same compartment. N2a cells were incubated with fluorescein-labeled PPI and LysoTracker Red, and performed dual channel confocal microscopy to compare the localization of the two compounds. The results indicate that fluorescein-labeled PPI accumulates in the lysosomes of living cells (FIGS. 7A, 7B and 7C).

Polypropyleneimine localizes to lysosomes N2a cells grown to 50% confluence on coverslips were incubated for 4 hrs with 3 FM FITC-PPI and 1 hr with 75 nM LysoTracker Red (Molecular Probes) in supplemented DME. Following incubation, coverslips were washed 3 times with PBS, fixed with 2% paraformaldehyde in PBS, and mounted onto microscope slides with VECTASHIELD. Fluorescence confocal microscopy in green and red channels was performed as described in Methods. Scale bar=5 Fm.

Branched Polyamines as Therapeutic Agents

A major finding of the above Examples is that branched polyamines eliminate prion infectivity in chronically infected living cells. This is believed to be the first class of compounds shown to cure an established prion infection. Polyene antibiotics, anionic dyes, sulphated dextrans, anthracylines, porphyrins, phthalocyanines, dapsone, and a synthetic β-breaker peptide all prolong scrapie incubation times in vivo, but only if administered very early in the course of infection.

The unique ability of branched polyamines to cure an established prion infection in cells indicates that they can be used for a therapy in animals, even when administered after the onset of symptoms. However, two factors could potentially limit the use of these compounds as therapeutic agents against prion diseases. Branched polyamines might not act on all strains of prions, and they might not cross the blood-brain barrier. The first possibility is suggested by our data, which show that some strains and species of prions are more resistant than others to branched polyamine-induced disaggregation in vitro. It remains to be determined whether prion strains resistant to branched polyamine-induced disaggregation in vitro would also be resistant to treatment by these compounds in vivo. Treatment of more resistant strains might require therapy with branched polyamines in combination with another class of prion-directed compounds.

The second potential limitation of branched polyamines is that these highly charged compounds might not cross the blood-brain barrier. If this proves to be the case, branched polyamines could be delivered directly to the CSF through an intraventricular reservoir, or perhaps synthesized as prodrugs capable of crossing the blood-brain barrier. Preliminary studies indicate that continuous intraventricular infusion of PPI generation 4.0 is tolerated by FVB mice up to a total dose of approximately 2 mg/animal (data not shown).

Molecular Target, Mechanism and Site of Action

It is important to characterize the molecular and cellular mechanisms by which branched polyamines eliminate prions for two reasons. First, branched polyamines could potentially be used as research tools to study the cellular and structural biology of prions. Second, identifying the molecular target of branched polyamines would facilitate the design of other compounds more specifically directed against this target.

Figure 3B:
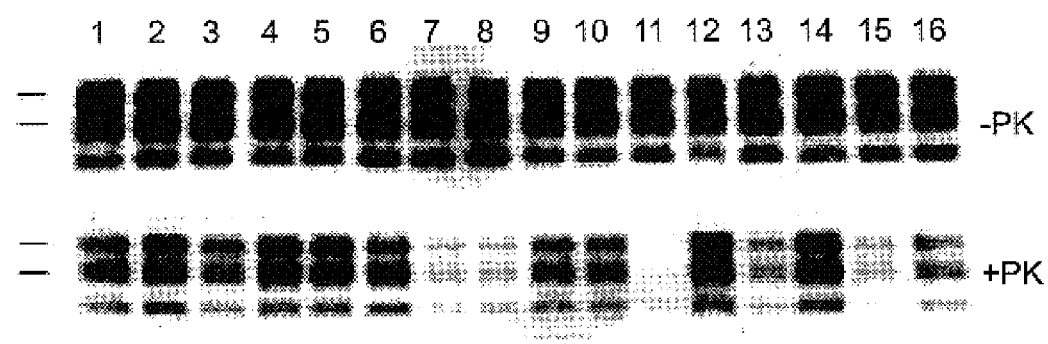

The ability of branched polyamines to render PrP$^{Sc}$ protease-sensitive in purified preparations, as shown in FIGS. 3A and 3B, suggests that the molecular target of these compounds must either be: (1) PrP$^{Sc}$ itself; (2) an acid-induced unfolding intermediate of PrP$^{Sc}$; or (3) a very tightly bound, cryptic molecule which copurifies with PrP$^{Sc}$. If the molecular target is PrP, at least one of the polyamine binding sites must be contained within the amino acid sequence of the PrP106 deletion mutant, since PPI renders PrP$^{Sc}$ 106 protease-sensitive (FIG. 4A, lane 6). The 106 amino acids present in PrP106 are residues 89–140 and 177–231. PPI also renders a spontaneously protease-resistant, 61 amino acid-long PrP deletion mutant, PrP( )23–88, )141–221), susceptible to protease-digestion, further confining the boundaries of at least one putative binding site to residues 89–140 and 222–231.

Several lines of evidence suggest that branched polyamines render PrP$^{Sc}$ molecules protease-sensitive by dissociating PrP$^{Sc}$ aggregates. (1) RML PrP27–30 prion rods treated in vitro with PPI become disaggregated, as judged by electron microscopy (FIGS. 6A and 6B). (2) Prion strains resistant to branched polyamines in vitro appear to be more amyloidogenic than polyamine-susceptible strains, as judged by neuropathology. (3) The ability of branched polyamines to render PrP$^{Sc}$ protease-sensitive in vitro is enhanced by conditions that favor PrP$^{Sc}$ disaggregation. These conditions include lower pH (FIG. 3A), higher temperature (FIG. 5B), and the presence of urea (FIG. 5A).

Theoretically, it is possible that the mechanism by which branched polyamines remove PrP$^{Sc}$ and prion infectivity from ScN2a cells does not relate to the ability of these compounds to disaggregate prions in vitro. However, this is unlikely because the relative potency of 14 different polyamines in eliminating PrP$^{Sc}$ from ScN2a cells exactly matches the relative ability of these same compounds to render PrP$^{Sc}$ protease-sensitive in crude brain homogenates and purified preparations of RML PrP27–30 in vitro (FIG. 3B). The structure-activity profile obtained from these studies indicates that polyamines become more potent at eliminating PrP$^{Sc}$ as they become more branched and possess more surface primary amines. With PPI dendrimers, this effect reaches a plateau at the fourth generation; PPI generation 5.0 is no more potent than PPI generation 4.0 at either removing PrP$^{Sc}$ from cells or rendering PrP$^{Sc}$ protease-sensitive in vitro. Homodisperse, uniform PPI and PAMAM dendrimers were more potent than the heterogeneous preparations of polyethyleneimine (PEI) or SuperFect™, a heat-fractured dendrimer.

The process by which PPI renders PrP$^{Sc}$ protease-sensitive in vitro was not catalytic. Instead, this process appeared to require a fixed stoichiometric ratio of PPI to PrP$^{Sc}$ of approximately 1:5. The question was presented regarding how PPI could disaggregate prion rods stoichiometrically. One possible explanation is that individual amino groups on the surface of PPI might bind to PrP$^{Sc}$ monomers or oligomers that exist in equilibrium with a large aggregate under acidic conditions. The dendrimer might then pry bound PrP$^{Sc}$ molecules apart from the aggregate and/or prevent such molecules from reaggregating.

Several lines of evidence indicate that the cellular site of action of branched polyamines is secondary lysosomes. (1) Fluorescein-tagged PPI and PrP$^{Sc}$ both localize to lysosomes (FIGS. 7A–C). (2) The pH optimum of PrP$^{Sc}$ disaggregation in vitro is <5.0. When cultured cells were studied with fluorescent acidotroptic pH measurement dyes, secondary lysosomes were the most acidic cellular compartment detected, with pH values of ~4.4–4.5. (3) The lysosomotropic agent chloroquine attenuates the ability of branched polyamines to eliminate PrP$^{Sc}$ from ScNa cells. It is thought that lysosomal proteases normally degrade $PrP^{Sc}$ in prion-infected cells at a slow rate, and that polyamines accelerate this process by disaggregating $PrP^{Sc}$.

Other Applications of Branched Polyamines

Beyond their potential use as therapeutic agents and research tools, branched polyamines might also be useful as prion strain typing reagents and/or prion decontaminants. Presently, typing of prion strains is time-consuming and requires the inoculation of samples into several strains of inbred animals to obtain incubation time and neuropathology profiles. In the Examples provided above it was shown that different species and strains of prions displayed varying susceptibilities to branched polyamine-induced disaggregation in vitro (FIG. 4A). These results indicate that a polyamine-based in vitro protease digestion assay could be used as a simple and rapid diagnostic method for prion strain typing. Currently, it is very difficult to remove prions from skin, tissues, organs, blood, clothes, surgical instruments, foodstuffs, and surfaces. Standard prion decontamination requires either prolonged autoclaving or exposure to harsh protein denaturants such as 1N NaOH or 6M guanidine thiocyanate. Branched dendrimers are non-toxic and relatively inexpensive. These compounds are suitable for use as a sterilizing agent to limit the commercial and iatrogenic spread of prion disease.

Example 15

Results provided here show that acidic conditions (<pH 5) enhance the ability of other compounds (e.g., dendrimers, SDS, and urea) to denature $PrP^{Sc}$ and destroy prion infectivity. Specific results demonstrate that acidic conditions can be used to formulate effective prion disinfectants emphasizing the importance of acidic conditions.

The Effectiveness of 1% SDS at pH 3.4 to Eliminate $PrP^{Sc}$ at 5 Minutes or 2 Hours A 2% homogenate of scrapie Sc237 brain in water was prepared by repeated extrusion through a 22 G needle. Nuclei were removed by centrifugation for 5 min at 1000 rpm. The clarified homogenate was diluted 2-fold and incubated for (FIG. 8A) 2 hrs or (FIG. 8B) 5 min at 37° C. under the following conditions:

1. 1% NP40, 50 mM sodium acetate pH 7.0;
2. 1% NP40, 0.5% acetic acid pH 3.4;
3. 1% SDS, 50 mM sodium acetate pH 7.0;
4. 1% SDS, 0.5% acetic acid pH 3.4;
5. 1% Sarkosyl, 50 mM sodium acetate pH 7.0; and
6. 1% Sarkosyl, 0.5% acetic acid pH 3.4.

Plus (+) lanes indicate samples subjected to limited proteolysis with 20 μg/ml proteinase K for 1 hr at 37° C., Minus (−) lanes indicate samples not subjected to proteolysis. All samples were boiled in SDS sample buffer for 5 min prior to SDS polyacrylamide gel electrophoresis. Following transfer to Millipore Immobilon transfer membrane, development of the immunoblot was performed with d13 primary Fab.

The Effect of Temperature on the Ability of 1% SDS at pH 3.4 to Eliminate $PrP^{Sc}$ A 2% homogenate of scrapie Sc237 brain in water was prepared by repeated extrusion through a 22 G needle. Nuclei were removed by centrifugation for 5 min at 1000 rpm. The clarified homogenate was diluted 2-fold and incubated for 5 min under the following conditions:

1. 1% SDS, 0.5% acetic acid pH 3.4 at 4° C.;
2. 1% SDS, 0.5% acetic acid pH 3.4 at 20° C.;
3. 1% SDS, 0.5% acetic acid pH 3.4 at 37° C.; and
4. 1% NP40, 0.5% acetic acid pH 3.4 at 20° C.

Plus (+) lanes of FIG. 9 indicate samples subjected to limited proteolysis with 20 μg/ml proteinase K for 1 hr at 37° C. Minus (−) lanes indicate samples not subjected to proteolysis. All samples were boiled in SDS samples buffer for 5 min prior to SDS polyacrylamide gel electrophoresis. Following transfer to Millipore Immobilon transfer membrane, development of the immunoblot was performed with d13 primary Fab.

The Ability of Acidic Conditions to Enhance Urea-Mediated $PrP^{Sc}$ Denaturation A 2% homogenate of scrapie Sc237 brain in water was prepared by repeated extrusion through a 22 G needle. Nuclei were removed by centrifugation for 5 min at 1000 rpm. The clarified homogenate was diluted 2-fold and incubated for 2 hours with 0.5% NP40 plus urea and 50 mM sodium acetate buffer (urea concentration and pH are indicated above FIG. 10).

All samples were subjected to limited proteolysis with 20 μg/ml proteinase K for 1 hr at 37° C., and boiled in SDS samples buffer for 5 min prior to SDS polyacrylamide gel electrophoresis. Following transfer to Millipore Immobolin transfer membrane, developments of the immunoblot was performed with d13 primary Fab.

Example 16

SDS/Acetic Acid Formulation

Samples of 1% Syrian hamster brain homogenate containing $10^7$ $LD_{50}$ units prion infectivity/ml were incubated with either 50 mM Tris acetate pH 7.0 or 0.5% acetic acid in the presence of either 1% NP-40 or 1% SDS for 2 h at 37° C. Following incubation, each sample was inoculated intracerebrally into 8 separate Syrian hamsters for a scrapie incubation time assay. The results are shown below:

| Sample | $LD_{50}$/ml |
|---|---|
| 1% NP40, 50 mM Tris acetate pH 7.0 | $10^7$ |
| 1% NP40, 5% acetic acid, pH 3.6 | $10^7$ |
| 1% SDS, 50 mM Tris acetate pH 7.0 | $10^5$ |
| 1% SDS, 5% acetic acid, pH 3.6 | $<10^2$ |

The above results clearly demonstrate that a formulation comprised of approximately 1% SDS and approximately 0.5% acetic acid is effective in inactivating prions. Such a formulation could provide for an extremely valuable commercial formulation due to the ready availability of both acetic acid and SDS. However, those skilled in the art will recognize that other effective acids and effective detergents with structure similar to SDS could be formulated to obtain the same or similar results. With respect to the acid component what is important is to create a formulation which keeps the pH of the formulation acidic and preferably below 5.0 and more preferably below 4.0. The detergent composition need not be SDS. For example, the sodium component of the detergent could be any cation such as calcium, lithium, potassium, magnesium etc. Further, the sulfate component could be substituted with chemically equivalent moieties. Sodium dodecyl sulfate includes a hydrocarbon component with eleven $CH_2$ groups terminated by a $CH_3$ group. Various other alkyl groups such as other straight chained, branched or cyclic groups could be utilized. The alkyl moiety could contain from 2 to 40 carbons and more preferably contains approximately 6–12 carbon atoms. The formulation can be added to appropriate solvents, in appropriate concentrations.

Further, the concentration of the formulation can be changed immediately prior to use and thus sold at a highly concentrated formulation or sold in a concentration ready for use without dilution with a solvent such as water or alcohol. Still further, as indicated above the formulations of the invention can be supplemented with appropriate antibacterial and/or antiviral components as well as components which inactivate other pathogens including parasites so that the final formulation is effective in killing or inactivating a wide range of infectious components.

Example 17
Effect of Detergent and pH on Protease-resistant PrP$^{Sc}$

Figure 11:
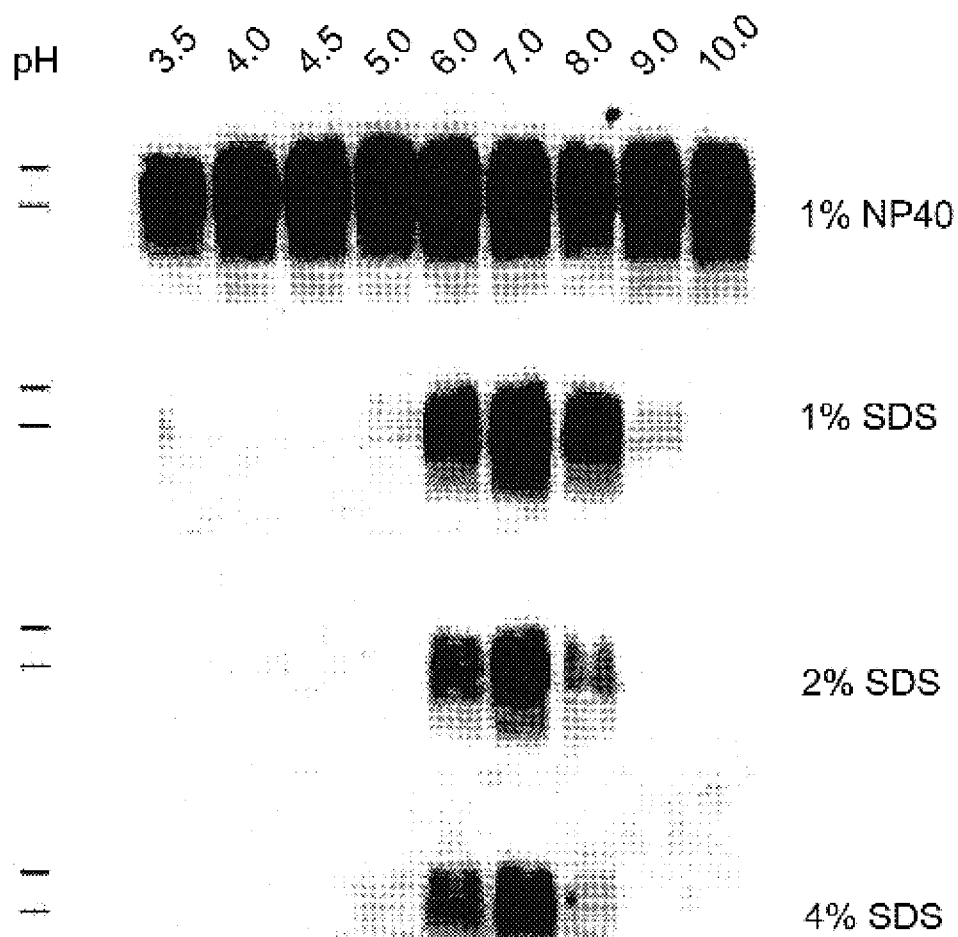
FIG. 11 shows four separate gels with each of the gels run at nine different specific pH levels showing that SDS does denature $PrP^{Sc}$ at low pH and high pH but not at a relatively neutral pH and further showing that increasing the percent concentration of SDS improves the ability of the formulation to denature $PrP^{Sc}$.

Samples of 1% Sc237-infected SHa brain homogenate were incubated for 15 min at 37° C. with detergent at a range pH values as indicated. Fifty millimolar sodium acetate buffers were used to maintain pH values 3–6, and 50 mM Tris acetate buffers were used to maintain pH values 7–10. The final pH value of each sample denoted above the corresponding lanes was measured directly with a calibrated pH electrode (Radiometer, Copenhagen). All samples were neutralized by addition of equal volume 4% Sarkosyl, 100 mM HEPES pH 7.5, 200 mM NaCl and subjected to limited proteolysis with 20 µg/ml proteinase K for 1 h at 37° C. Apparent molecular weights based on migration of protein standards are 30 and 27 kDa. All samples were neutralized by addition of equal volume 4% Sarkosyl, 100 mM HEPES pH 7.5, 200 mM NaCl. Minus (−) symbol denotes undigested, control sample and plus (+) symbol designates sample subjected to limited proteolysis with 20 µg/ml proteinase K for 1 h at 37° C. Apparent molecular weights based on migration of protein standards are 30 and 27 kDa. FIG. 11 shows that SDS denatures PrPSc at pH<5 or pH>10.

Example 18
Characterization of PrP$^{Sc}$ Denaturation Mediated by Acidic SDS

Figure 12:
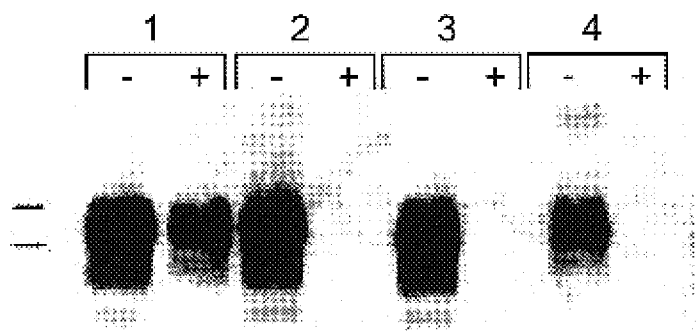
FIG. 12 provides gel panels that show that acetic buffers other than acetic acid and sodium acetate can be used in combination with SDS in order to denature $PrP^{Sc}$.

As shown in FIG. 12, samples of 1% Sc237-infected SHa brain homogenate were incubated for 15 min at 37° C. in 1% SDS plus (lane 1) 50 mM Tris acetate pH 7.0, (lane 2) 50 mM sodium acetate pH 3.6, (lane 3) 50 mM glycine pH 3.7, and (lane 4) 0.2% peracetic acid, pH 3.4. Following incubation, an equal volume of 4% Sarkosyl, 100 mM HEPES pH 7.5, 200 mM NaCl was added to neutralize each sample. Minus (−) symbol denotes undigested, control sample and plus (+) symbol designates sample subjected to limited proteolysis with 20 µg/ml proteinase K for 1 h at 37° C. Apparent molecular weights based on migration of protein standards are 30 and 27 kDa. The results in FIG. 12 show that SDS denatures PrPSc under acidic conditions in different acidic buffers, including peracetic acid (a commonly used hospital disinfectant).

Example 19
PrP$^{Sc}$ Denaturation by 1% Alkyl Sulfates and Sulfonates

Figure 13A:
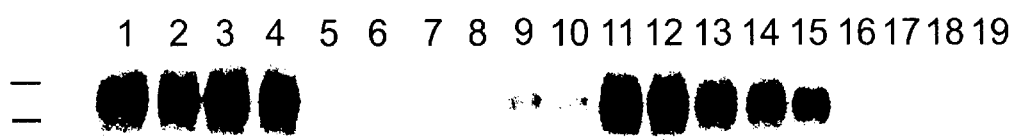
FIG. 13A is a photograph of a gel that shows the denaturation of PrPSc by different alkyl sulfates and alkyl sulfonates.

As shown in FIG. 13A, different alkyl sulfates and alkyl sulfonates were tested to see if they had the ability to denature prions. 1% (w/v) Sc237 scrapie-infected Syrian hamster (SHa) brain homogenate in 0.5% acetic acid, was incubated with 1% of the detergent specified for 2 hours at 37° C. Following incubation, each sample was mixed with equal volumes of 4% Sarkosyl, 100 mM HEPES (pH 8.0), and 200 mM NaCl. The mixture was subjected to SDS-PAGE and immunoblot with d13 chimeric Fab. Apparent molecular weights based on migration of protein standards are 30 and 27 kDa.

The results show that seven of the compounds tested were effective in denaturing prions. Those compounds are: $C_{10}$ alkyl sulfate, sodium salt, $C_{11}$ alkyl sulfate, sodium salt; $C_{12}$ alkyl sulfate, sodium salt (SDS); $C_{10}$ alkyl sulfonate, sodium salt; $C_{11}$ alkyl sulfonate, sodium salt; $C_{12}$ alkyl sulfonate, sodium salt; and $C_{13}$ alkyl sulfonate, sodium salt.

Example 20
PrP$^{Sc}$ Denaturation by Alkyl Sulfates at 4° C. and 37° C.

Figure 13B:
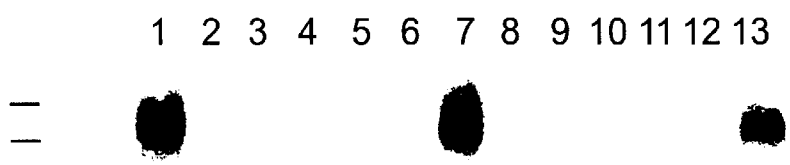
FIG. 13B is a photograph of a gel that shows the denaturation of PrPSc by alkyl sulfates at 4° C. or 37° C.
Figure 14:
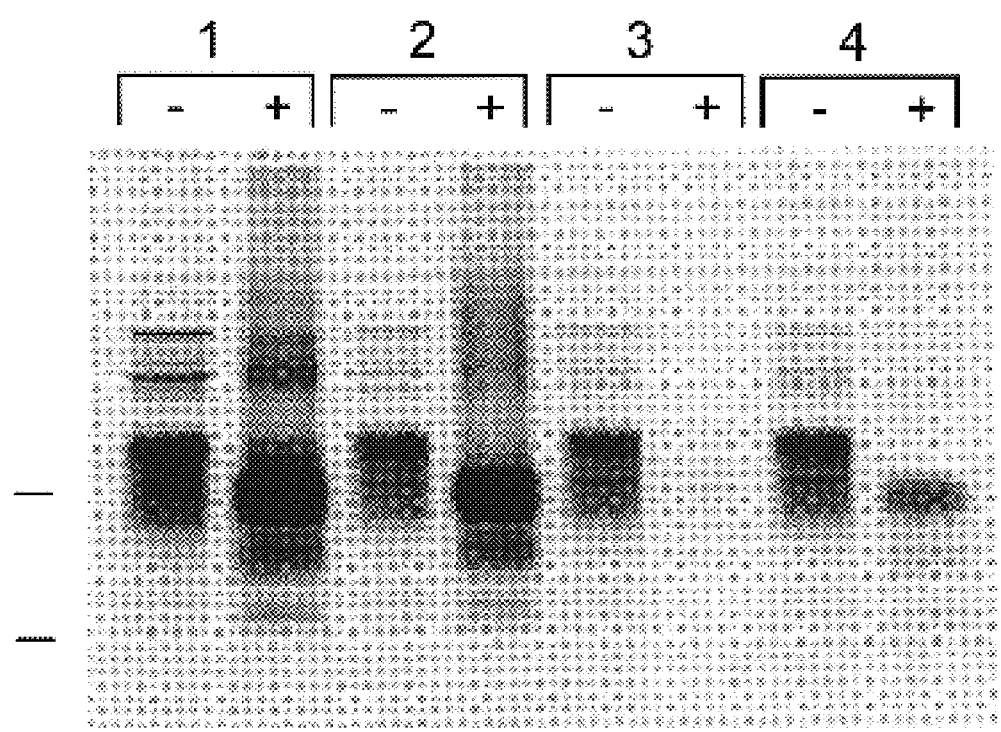
FIG. 14 is a photograph of a Western blot gel. Homogenates of BSE-infected bovine brain were successfully denatured of prions by exposure to acidic SDS, see lane 3.

As shown in FIG. 13B, different alkyl sulfates and alkyl sulfonates were tested to see if they had the ability to denature prions. 1% (w/v) Sc237 scrapie-infected Syrian hamster (SHa) brain homogenate in 0.5% acetic acid, was incubated with 1% of the detergent specified for 2 hours at 37° C. Following incubation, each sample was mixed with equal volumes of 4% Sarkosyl, 100 mM HEPES (pH 8.0), and 200 mM NaCl. The mixture was subjected to limited proteolysis with 20 µg/ml proteinase K for 1 hour at either 4° C. or 37° C., as indicated. Each sample was subjected to SDS-PAGE and immunoblot with d13 chimeric Fab. Apparent molecular weights based on migration of protein standards are 30 and 27 kDa.

Specifically, referring to FIG. 13A, lane 1 is $C_5$ alkyl sulfate, sodium salt, Lane 2 is $C_6$ alkyl sulfate, sodium salt, Lane 3 is $C_7$ alkyl sulfate, sodium salt, Lane 4 is $C_8$ alkyl sulfate, sodium salt, Lane 5 is $C_9$ alkyl sulfate, sodium salt, Lane 6 is $C_{10}$ alkyl sulfate, sodium salt, Lane 7 is $C_{11}$ alkyl sulfate, sodium salt, Lane 8 is $C_{12}$ alkyl sulfate, sodium salt, Lane 9 is $C_{13}$ alkyl sulfate, sodium salt, Lane 10 is $C_{14}$ alkyl sulfate, sodium salt, Lane 11 is an untreated control sample, Lane 12 is an untreated control sample, Lane 13 is $C_6$ alkyl sulfonate, sodium salt, Lane 14 is $C_7$ alkyl sulfonate, sodium salt, Lane 15 is $C_9$ alkyl sulfonate, sodium salt, Lane 16 is $C_{10}$ alkyl sulfonate, sodium salt, Lane 17 is $C_{11}$ alkyl sulfonate, sodium salt, Lane 18 is $C_{12}$ alkyl sulfonate, sodium salt, and Lane 19 is $C_{13}$ alkyl sulfonate, sodium salt.

Specifically, referring to FIG. 13B, lane 1 is an untreated control sample at 4° C., Lane 2 is $C_{10}$ alkyl sulfate, sodium salt at 4° C., Lane 3 is $C_{11}$ alkyl sulfate, sodium salt at 4° C., Lane 4 is $C_{12}$ alkyl sulfate, sodium salt at 4° C., Lane 5 is $C_{12}$ alkyl sulfate, lithium salt at 4° C. Lane 6 is $C_{12}$ alkyl sulfate, Tris salt at 4° C. Lane 7 is an untreated control sample at 37° C. Lane 8 is $C_{10}$ alkyl sulfate, sodium salt at 37° C. Lane 9 is $C_{11}$ alkyl sulfate, sodium salt at 37° C. Lane 10 is $C_{12}$ alkyl sulfate, sodium salt at 37° C. Lane 11 is $C_{12}$ alkyl sulfate, lithium salt at 37° C. Lane 12 is $C_{12}$ alkyl sulfate, Tris salt at 37° C. and Lane 13 is docusate, sodium salt at 37° C.

The results show that ten of the compounds tested were effective in denaturing prions. Those compounds are: $C_{10}$ alkyl sulfate, sodium salt at 4° C.; $C_{11}$ alkyl sulfate, sodium salt at 4° C.; $C_{12}$ alkyl sulfate, sodium salt at 4° C.; $C_{12}$ alkyl sulfate, lithium salt at 4° C.; $C_{12}$ alkyl sulfate, Tris salt at 4° C.; $C_{10}$ alkyl sulfate, sodium salt at 37° C.; $C_{11}$ alkyl sulfate, sodium salt at 37° C.; $C_{12}$ alkyl sulfate, sodium salt at 37° C.; $C_{12}$ alkyl sulfate, lithium salt at 37° C.; and $C_{12}$ alkyl sulfate, Tris salt at 37° C.

Example 21
Acidic SDS Disinfects Stainless Steel Wire Contaminated with Prions

A system was devised to measure disinfection of cylindrical stainless steel suture wire (see Zobeley et al. (1999) Mol. Med. 5:240–243). Zobeley et al. showed that prions bound to stainless steel were resistant to disinfection by formaldehyde.

In the present example, the procedure of Zobeley et al. was modified to test the ability of acidic SDS to disinfect prions attached to a steel surface. Five ml segments of 3–0 stainless steel suture wire (Ethicon) coated with RML (Rocky Mountain Laboratory) murine prions were incubated in PBS or 10% SDS, 5% acetic acid at 65° C. for 16 h. Following incubation, the wire segments were implanted into the parietal lobes of Tg(MoPrP)4053 indicator mice for the purpose of generating a bioassay. The wires remained embedded in the brains of the indicator mice for the duration of the experiment.

Bioassays in Tg(MoPrP)4053 mice are able to detect as few as ten $LD_{50}$ infectious prion units/sample. The results, shown below in Table 3, indicate that incubation with acidic SDS reduces prion infectivity to a level below detection of this sensitive bioassay.

TABLE 3

| Implanted wire | Scrapie incubation time (days ± SEM) | $n/n_0$ | Prion infectivity ($LD_{50}$ units/wire) |
|---|---|---|---|
| Coated with RML prions and incubated with PBS | 74 ± 1 | 20/20 | $10^3$ |
| Coated with RML prions and incubated with acidic SDS | >110 | 0/20 | undetectable |
| Control (no prions) | >110 | 0/15 | undetectable |

Example 22

Acidic SDS Denatures $PrP^{Sc}$ in BSE-infected Bovine Brain

It was investigated whether acidic SDS could denature prion strains other than the Syrian hamster Sc237 strain. Samples were incubated that contained 2.5% BSE-infected bovine brain homogenate with acidic SDS or control buffers for 15 min. at 37° C. In these conditions, $PrP^{Sc}$ in BSE-infected brain tissue was denatured successfully by exposure to acidic SDS, as shown by Western blot in FIG. 14.

The buffers used in lanes 1–4 of FIG. 14 are as follows: lane 1—1% NP40; 50 mM Tris acetate; lane 2—1% NP40; 0.5% acetic acid, pH 3.6; lane 3—1% SDS; 0.5% acetic acid, pH 3.6; and lane 4—1% SDS, 50 mM Tris acetate, pH 7.0. Following incubation, an equal volume of 2% NP40, 100 mM HEPES, pH 7.5, and 200 mM NaCl was added to neutralize each sample, and then the samples were dialyzed (mol. wt. cutoff: 10 kDa) against 1% NP40, 50 mM HEPES, pH 7.5, 100 mM NaCl at 4° C. for 16 h. The minus (−) symbol above the lane indicates undigested, control sample. The plus (+) symbol above the lane indicates the sample was subjected to limited proteolysis with 20 μg/ml proteinase K for 1 h. at 37° C. Protease-digested samples were centrifuged at 100,000×g., supernatant fractions were discarded, and pellets were boiled for 10 min. in SDS sample buffer prior to electrophoresis. Apparent molecular weights based on migration of protein standards are 30 and 17 kDa.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of inactivating the infectivity of a PrP protein, comprising the steps of:

contacting a PrP protein with a composition comprising an acid component and an active component chosen from $C_{10}$ alkyl sulfate, sodium salt; $C_{11}$ alkyl sulfate, sodium salt; $C_{12}$ alkyl sulfate, sodium salt; $C_{12}$ alkyl sulfate, lithium salt; and $C_{12}$ alkyl sulfate, Tris salt;

maintaining the composition in contact with the PrP protein at a pH in a range of from about 2.5 to about 4.5 with an acid chosen from acetic acid, lactic acid and peracetic acid at a temperature in a range of from about 37° C. to about 80° C. thereby rendering the PrP protein completely non-infectious in 2.0 hours or less.

2. The method of claim 1, wherein the composition is further comprised of a solvent.

3. The method of claim 2 wherein the solvent is chosen from an aqueous solvent and an alcohol solvent.

* * * * *